(12) United States Patent
Feldman et al.

(10) Patent No.: US 10,689,669 B1
(45) Date of Patent: **\*Jun. 23, 2020**

(54) AUTOMATED MULTI-MODULE CELL PROCESSING METHODS, INSTRUMENTS, AND SYSTEMS

(71) Applicant: Inscripta, Inc., Boulder, CO (US)

(72) Inventors: Emily Feldman, Boulder, CO (US); Benjamin Mijts, Boulder, CO (US); Aamir Mir, Boulder, CO (US); Erik Zimmerman, Boulder, CO (US); Andrew Garst, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/740,418

(22) Filed: Jan. 11, 2020

(51) Int. Cl.
 *C12M 3/00* (2006.01)
 *C12M 1/00* (2006.01)
 *C12N 15/87* (2006.01)
 *C12M 1/34* (2006.01)

(52) U.S. Cl.
 CPC ............ *C12N 15/87* (2013.01); *C12M 29/26* (2013.01); *C12M 41/36* (2013.01)

(58) Field of Classification Search
 CPC ............ B01L 2200/04; B01L 2200/06; B01L 2200/18; C12M 35/00; C12M 35/04
 See application file for complete search history.

(56) References Cited

U.S. PATENT DOCUMENTS

| | | | |
|---|---|---|---|
| 4,833,080 A | 5/1989 | Brent et al. | |
| 4,959,317 A | 9/1990 | Sauer et al. | |
| 5,464,764 A | 11/1995 | Capecchi et al. | |
| 5,487,992 A | 1/1996 | Capecchi et al. | |
| 5,627,059 A | 5/1997 | Capecchi et al. | |
| 5,631,153 A | 5/1997 | Capecchi et al. | |
| 5,654,182 A | 8/1997 | Wahl et al. | |
| 5,677,177 A | 10/1997 | Wahl et al. | |
| 5,710,381 A | 1/1998 | Atwood et al. | |
| 5,792,943 A | 8/1998 | Craig | |
| 5,885,836 A | 3/1999 | Wahl et al. | |
| 5,888,732 A | 3/1999 | Hartley et al. | |
| 6,074,605 A | 6/2000 | Meserol et al. | |
| 6,127,141 A | 10/2000 | Kopf | |
| 6,143,527 A | 11/2000 | Pachuk et al. | |
| 6,150,148 A | 11/2000 | Nanda et al. | |
| 6,204,061 B1 | 3/2001 | Capecchi et al. | |
| 6,277,608 B1 | 8/2001 | Hartley et al. | |

(Continued)

FOREIGN PATENT DOCUMENTS

| | | |
|---|---|---|
| CN | 2397122 Y | 9/2000 |
| EP | 2135626 A1 | 12/2009 |

(Continued)

OTHER PUBLICATIONS

Yoshioka, et al., "Development for a mono-promoter-driven CRISPR/CAS9 system in mammalian cells", Scientific Reports, Jul. 3, 2015, p. 1-8.

(Continued)

*Primary Examiner* — Nathan A Bowers
(74) *Attorney, Agent, or Firm* — Sarah Brashears; Dianna L. DeVore

(57) ABSTRACT

The present disclosure provides automated multi-module instruments, compositions and methods to increase the percentage of edited mammalian cells in a cell population when employing nucleic-acid guided editing.

20 Claims, 50 Drawing Sheets

(56) References Cited

U.S. PATENT DOCUMENTS

| | | | |
|---|---|---|---|
| 6,482,619 B1 | 11/2002 | Rubinsky et al. |
| 6,509,156 B1 | 1/2003 | Stewart et al. |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,926,977 B2 | 1/2015 | Miller et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,260,505 B2 | 2/2016 | Weir et al. |
| 9,361,427 B2 | 6/2016 | Hillson |
| 9,499,855 B2 | 11/2016 | Hyde et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,017,760 B2 | 7/2018 | Gill et al. |
| 10,266,851 B2 | 4/2019 | Chen |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0110253 A1 | 6/2004 | Kappler et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0224192 A1 | 10/2006 | Dimmer et al. |
| 2007/0042427 A1 | 2/2007 | Gerdes et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0003303 A1 | 1/2011 | Pagano et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0196441 A1 | 8/2013 | Rubinsky et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0273226 A1 | 9/2014 | Wu et al. |
| 2014/0350456 A1 | 11/2014 | Caccia |
| 2015/0072413 A1 | 3/2015 | Zenhausern et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0297887 A1 | 10/2015 | Dhillon et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0272961 A1 | 9/2016 | Lee |
| 2016/0281047 A1 | 9/2016 | Chen et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0367991 A1 | 12/2016 | Petersen et al. |
| 2017/0002339 A1 | 1/2017 | Barrngou et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0218355 A1 | 8/2017 | Buie et al. |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0142196 A1 | 5/2018 | Coppeta et al. |
| 2018/0155665 A1 | 6/2018 | Zenhausern et al. |
| 2018/0169148 A1 | 6/2018 | Adair et al. |
| 2018/0179485 A1 | 6/2018 | Borenstein et al. |
| 2018/0230460 A1 | 8/2018 | Gill et al. |
| 2019/0017072 A1 | 1/2019 | Ditommaso et al. |
| 2019/0169605 A1 | 6/2019 | Masquelier et al. |

FOREIGN PATENT DOCUMENTS

| | | |
|---|---|---|
| EP | 2240238 | 10/2010 |
| EP | 2395087 | 12/2011 |
| EP | 3030652 | 6/2016 |
| EP | 1766004 | 8/2016 |
| EP | 2459696 | 11/2017 |
| WO | WO 2003/057819 | 7/2001 |
| WO | WO 2003/087341 | 10/2003 |
| WO | WO 2009/091578 | 7/2009 |
| WO | WO 2010079430 | 7/2010 |
| WO | WO 2011/072246 | 6/2011 |
| WO | WO2011/143124 | 11/2011 |
| WO | WO2012012779 A3 | 1/2012 |
| WO | WO2013/142578 | 9/2013 |
| WO | WO 2013/176772 | 11/2013 |
| WO | WO2014/018423 | 1/2014 |
| WO | WO2014/144495 A1 | 9/2014 |
| WO | WO 201/5021270 | 2/2015 |
| WO | WO 2016/003485 | 1/2016 |
| WO | WO 2016/054939 | 4/2016 |
| WO | WO 2016/145290 | 9/2016 |
| WO | WO2017/053902 A1 | 3/2017 |
| WO | WO 2017/078631 | 5/2017 |
| WO | WO2017/083722 | 5/2017 |
| WO | WO2017/161371 | 9/2017 |
| WO | WO2017/174329 A1 | 10/2017 |
| WO | WO2017/186718 | 11/2017 |
| WO | WO 2018/015544 | 1/2018 |
| WO | WO2018/031950 A1 | 2/2018 |
| WO | WO2018/083339 A1 | 5/2018 |
| WO | WO 2018/191715 | 10/2018 |

(56) References Cited

OTHER PUBLICATIONS

Remaut, et al., "Plasmid vectors for high-efficiency expression controlled by the PL promoter of coliphage lambda", Laboratory of Molecular Biology, Apr. 15, 1981, p. 81-93.
International Search Report and Written Opinion for International Application No. PCT/US19/46515, dated Oct. 28, 2019, p. 1-11.
International Search Report and Written Opinion for International Application No. PCT/US19/49735, dated Nov. 18, 2019, p. 1-13.
International Search Report and Written Opinion for International Application No. PCT/US19/46526, dated Dec. 18, 2019, p. 1-17.
International Search Report and Written Opinion for International Application No. PCT/US18/34779, dated Nov. 26, 2018, p. 1-39.
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Eklund, et al., "Altered target site specificity variants of the I-Ppol His-Cys bis homing endonuclease" Nucleic Acids Research, 35(17):5839-50 (2007).
Garst, et al., "Genome-wide mapping of mutations at single-nucleotide resolution for protein, metabolic and genome engineering", Nature Biotechnology, 35(1):48-59 (2017).
Boles, et al., "Digital-to-biological converter for on-demand production of biologics", Nature Biotechnology, doi:10.1038/nbt.3859 (May 29, 2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Pines, et al., "Codon Compression Algorithms for Saturation Mutagenesis", ACS Synthetic Biology, 4:604-14 (2015).
Verwaal, et al., "CRISPR/Cpfl enables fast and simple genome editing of *Saccaramyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).
Dong, "Establishment of a highly efficient virus-inducible CRISPR/Cas9 system in insect cells," Antiviral Res., 130:50-7(2016).
Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(11):e3647 (2008).
Epinat et al., "A novel engineered meganuclease induces homologous recombination in eukaryotic cells, e.g., yeast and mammalian cells", Nucleic Acids Research, 31(11): 2952-2962.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):e1004724 (2016).
Adamo, et al., "Flow-through comb electroporation device for delivery of macromolecules", Analytical Chemistry, 85(3):1637-41 (2015).
Greger et al., "Balancing transcriptional interference and initiation on the GAL7 promoter of *Saccharomyces cerevisiae*," PNAS, 97(15):8415-20 (2000).
Juan et al., "Histone deacetylases specifically down-regulate p53-dependent gene activation," Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Lefevre et al., "Alanine-stretch scanning mutagenesis: a simple and efficient method to probe protein structure and function," Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2):143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
International Search Report and Written Opinion for International Application No. PCT/US2018/040519, dated Sep. 26, 2018, p. 1-8.
International Search Report and Written Opinion for International Application No. PCT/US2018/053608, dated Dec. 13, 2018, p. 1-9.

(56) References Cited

OTHER PUBLICATIONS

International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.
International Search Report and Written Opinion for International Application No. PCT/US2019/023342 dated Jun. 6, 2019, p. 1-12.
International Search Report and Written Opinion for International Application No. PCT/US2019/026836 dated Jul. 2, 2019, p. 1-10.
International Search Report and Written Opinion for International Application No. PCT/US2019/028821 dated Aug. 2, 2019, p. 1-14.
International Search Report and Written Opinion for Interational Application No. PCT/US2019/028883 dated Aug. 16, 2019, p. 1-12.
International Search Report and Written Opinion for International Application No. PCT/US2019/030085 dated Jul. 23, 2019, p. 1-14.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication for U.S. Appl. No. 16/024,831, dated Feb. 12, 2019, p. 1-37.
First Office Action Interview Pilot Program Pre-Interview Communication for U.S. Appl. No. 16/360,404 dated Jul. 1, 2019, p. 1-27.
First Office Action Interview Pilot Program Pre-Interview Communication for U.S. Appl. No. 16/360,423 dated Jul. 1, 2019, p. 1-27.
Non Final Office Action for U.S. Appl. No. 16/399,988 dated Jul. 31, 2019, p. 1-20.
First Office Action Interview Pilot Program Pre-Interview Communication for U.S. Appl. No. 16/454,865 dated Aug. 16, 2019, p. 1-36.

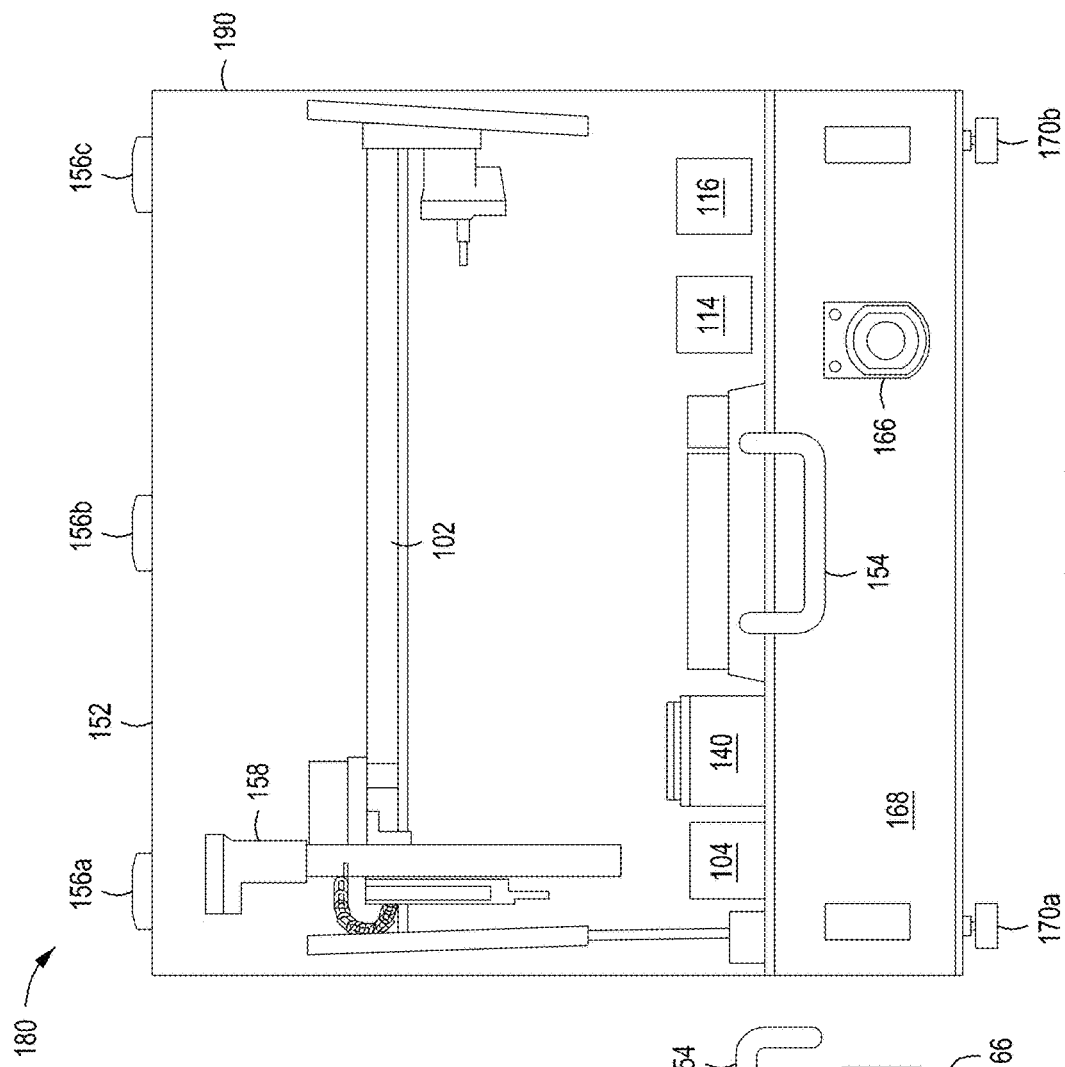
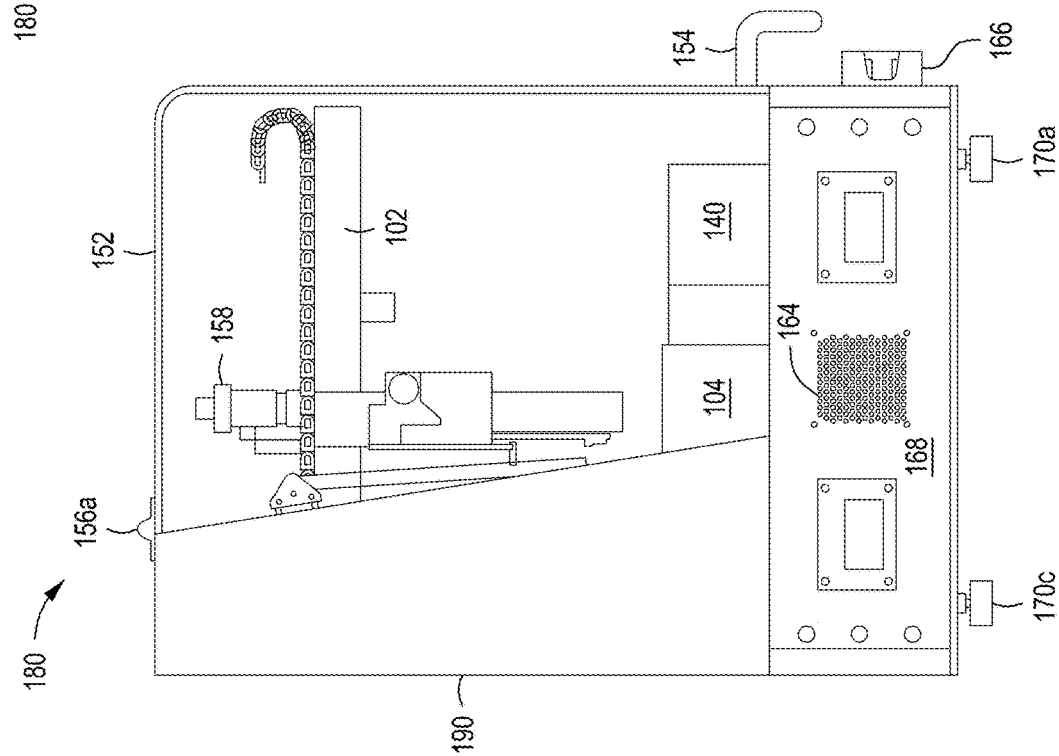
FIG. 1D
FIG. 1C

| 542 → | A | B | C | D |
|---|---|---|---|---|
| 1 | 510 | 514 | 518 | 522 |
| 2 | 511 | 515 | 519 | 523 |
| 3 | 512 | 516 | 520 | 524 |
| 4 | 513 | 517 | 521 | 525 |

| | Sample Name | Mean: PE (YG)-A | cv: PE (YG)-A |
|---|---|---|---|
| ☐ | 1907 30 Thy1.2 MACS bead titration_Input.fcs | 1162 | 630 |
| ☐ | 1907 30 Thy1.2 MACS bead titration_1_Elution.fcs | 1235 | 586 |
| ☐ | 1907 30 Thy1.2 MACS bead titration_2_Elution.fcs | 30426 | 143 |
| ☐ | 1907 30 Thy1.2 MACS bead titration_3_Elution.fcs | 19414 | 145 |
| ☐ | 1907 30 Thy1.2 MACS bead titration_4_Elution.fcs | 22693 | 148 |
| ☐ | 1907 30 Thy1.2 MACS bead titration_5_Elution.fcs | 17320 | 166 |
| ☐ | 1907 30 Thy1.2 MACS bead titration_6_Elution.fcs | 10369 | 196 |

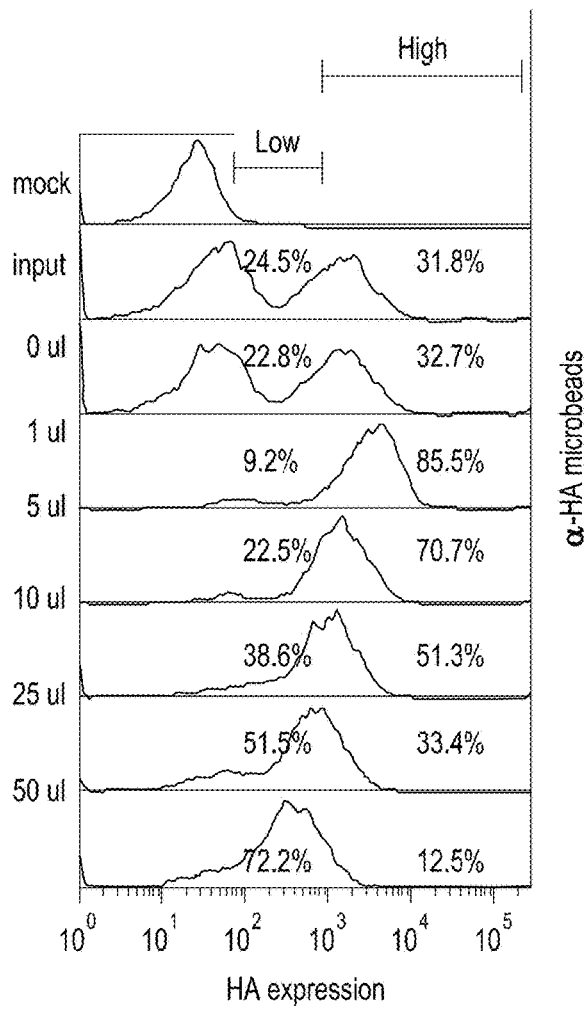

FIG. 20A

| | Sample Name | Mean: PE (YG)-W | cv: PE (YG)-W |
|---|---|---|---|
| ☐ | anti-H4 microbead titration H4P1GFPdTethenin-HA_HAP1-GFP mock.fcs | 49167 | 45.0 |
| ☐ | anti-H4 microbead titration H4P1GFPdTethenin-HA_HAP1-GFP5 ul beads input.fcs | 76647 | 43.7 |
| ☐ | anti-H4 microbead titration H4P1GFPdTethenin-HA_HAP1-GFP50 beads elution.fcs | 72186 | 46.6 |
| ☐ | anti-H4 microbead titration H4P1GFPdTethenin-HA_HAP1-GFP1 ul beads elution.fcs | 101495 | 18.4 |
| ☐ | anti-H4 microbead titration H4P1GFPdTethenin-HA_HAP1-GFP5 ul beads elution.fcs | 101730 | 17.6 |
| ☐ | anti-H4 microbead titration H4P1GFPdTethenin-HA_HAP1-GFP10 ul beads elution.fcs | 96764 | 26.2 |
| ☐ | anti-H4 microbead titration H4P1GFPdTethenin-HA_HAP1-GFP25 ul beads elution.fcs | 94078 | 25.2 |
| ☐ | anti-H4 microbead titration H4P1GFPdTethenin-HA_HAP1-GFP50 ul beads elution.fcs | 89095 | 29.5 |

FIG. 20B

AUTOMATED MULTI-MODULE CELL PROCESSING METHODS, INSTRUMENTS, AND SYSTEMS

FIELD OF THE INVENTION

The present disclosure relates to methods and compositions to increase the percentage of edited mammalian cells in a cell population when using nucleic-acid guided editing, as well as automated multi-module instruments for performing these methods using the disclosed compositions.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences, and hence gene function. The nucleases include nucleic acid-guided nucleases, which enable researchers to generate permanent edits in live cells. Of course, it is desirable to attain the highest editing rates possible in a cell population; however, in many instances the percentage of edited cells resulting from nucleic acid-guided nuclease editing can be in the single digits.

There is thus a need in the art of nucleic acid-guided nuclease editing for improved methods, compositions, modules and instruments for increasing the efficiency of editing. The present disclosure addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

In certain aspects, the present disclosure relates to methods, compositions, modules and automated multi-module cell processing instruments that increase the efficiency of nucleic-acid guided editing in a cell population, e.g., a mammalian cell population. Thus, methods presented herein include methods for increasing the rate of targeted editing using non-homologous end joining (NHEJ) repair, base editing, microhomology-directed repair (MMEJ) and/or homology-directed repair (HDR).

In some aspects, the disclosure provides methods for improving nuclease-directed editing of cells using enrichment means to identify cells that have received the editing components needed to perform the intended editing operation. Enrichment can be performed directly or using surrogates, e.g., cell surface handles co-introduced with one or more components of the editing components.

In specific aspects, the disclosure provides methods for improving nuclease-directed editing of cells using enrichment means to identify cells that have received the editing components needed to perform the intended editing operation.

In some aspects, the enrichment handle and method can be based on a positive versus negative signal of the surrogate. In other aspects, the enrichment method can be based on a threshold level of a surrogate, e.g., a high level of an enrichment handle versus a low or absent level of an enrichment handle.

In some aspects, the disclosure provides methods for improving nuclease-directed editing rates by enriching for mammalian cells that have received an HDR donor, e.g., identifying cells that are more likely to have received the editing apparatus along with the designs encoding the enrichment handle.

In specific aspects, the disclosure provides methods for improving nuclease-directed editing of mammalian cells using enrichment means to identifying mammalian cells that have received the HDR donor, the guide nucleic acid, and/or the nuclease. Such enrichment may involve a single enrichment method for HDR donor, the guide nucleic acid, and the nuclease, or two or more separate enrichment events for one or more of these elements. The HDR donor and guide nucleic acid may be introduced separately or covalently linked, as disclosed in, e.g., U.S. Pat. No. 9,982,278.

In some aspects, the disclosure provides methods of enriching for the editing efficiency of a target region in a cell population, the method comprising contacting a population of two or more cells with editing machinery comprising (a) one or more editing cassettes comprising a nucleic acid encoding a gRNA sequence targeting a first target region, wherein the gRNA is covalently attached to a region homologous to said first target region comprising an intended change in sequence relative to said target region, (b) one or more editing cassettes comprising a nucleic acid encoding a gRNA sequence targeting a second target region, wherein the gRNA is covalently attached to a region encoding a selectable marker and (c) a nuclease compatible with said gRNA sequence, exposing the population of cells to conditions to allow the cells to edit at the first and second target regions; and enriching for the cells from the population that express the selectable marker, wherein the selectable marker serves as a surrogate for editing of the first target region in the enriched cells of the cell population; and wherein the cells expressing the selectable marker are enriched for editing of the first target regions as compared to the cells of the population that do not express the selectable marker.

In some aspects, the disclosure provides a method of increasing the editing efficiency of a cell population, the method comprising contacting a population of two or more cells with editing machinery comprising (a) one or more editing cassettes comprising a nucleic acid encoding a gRNA sequence targeting a first target region, wherein the gRNA is covalently attached to a region homologous to said first target region comprising an intended change in sequence relative to said target region, (b) one or more editing cassettes comprising a nucleic acid encoding a gRNA sequence targeting a second target region, wherein the gRNA is covalently attached to a region encoding a selectable marker, and (c) nucleic acids encoding a nuclease compatible with said gRNA sequence, exposing the population of cells to conditions to allow the cells to edit at the first and second target regions, and enriching for the cells from the population that express the selectable marker, wherein the selectable marker serves as a surrogate for editing of the first target region in the enriched cells of the cell population.

In certain aspects, the cell enrichment uses a physical enrichment of the cells expressing the selectable marker. Examples of this include fluorescent-activated cell sorting selection, magnetic-activated cell sorting selection, antibiotic selection, and the like.

In certain aspects, the cell enrichment uses a computational enrichment based on the presence of a selectable marker.

In some aspects, the editing cassette targeting the first target region further comprises a barcode. In a specific aspect, the method further comprises incorporation of site-specific genomic barcodes that enable tracking of individual edited cells within a population.

In specific aspects of the invention, the HDR is improved using fusion proteins that retain certain characteristics of RNA-directed nucleases (e.g., the binding specificity and ability to cleave one or more DNA strands) and also utilize other enzymatic activities, e.g., replication inhibition, reverse transcriptase activity, transcription enhancement activity, and the like. These nuclease fusion proteins can be used in nuclease-directed editing using the disclosed methods, with or without the enrichment methods as disclosed herein. The HDR donor and guide nucleic acid may be introduced separately or covalently linked, as disclosed in, e.g., U.S. Pat. No. 9,982,278.

In specific aspects of the invention, the HDR is improved using fusion proteins that retain the binding function and nickase activity of an RNA-directed nuclease and also utilize other enzymatic activities, e.g., replication inhibition, reverse transcriptase activity, transcription enhancement activity, and the like. These nickase fusion proteins can be used in RNA-directed nickase editing using the disclosed methods, with or without the enrichment methods as disclosed herein. The HDR donor and guide nucleic acid may be introduced separately or covalently linked, as disclosed in, e.g., U.S. Pat. No. 9,982,278. In addition, nickase can be introduced using DNA coding for the nickase introduced separately or covalently linked to the donor and guide DNA, or introduced separately in protein form.

In specific aspects, the editing methods include the use of a fusion protein with nucleic acids having a guide RNA covalently attached to a region homologous to a target region that contains one or more changes from the native target sequence, and preferably at least one enrichment mechanism, physical or computational. Such methods can use a single guide RNA construct, or use two or more guide RNA constructs to target different genomic locations. In some aspects, the nucleic acids contain multiple guide RNAs covalently attached to different target regions within the genome.

In specific aspects, the editing methods include the use of a nickase fusion protein with nucleic acids having a guide RNA covalently attached to a region homologous to a target region that contains one or more changes from the native target sequence, and at least one enrichment mechanism, physical or computational.

Use of fusion proteins and enrichment for editing methods may involve a single enrichment method for HDR donor, the guide nucleic acid, and the nuclease, or two or more separate enrichment events for one or more of these editing machinery elements.

In specific aspects, the cells receiving the HDR donor can be enriched using an initial enrichment step, e.g., using an antibiotic selection or fluorescent detection, following by an enrichment step using an enrichment of the cells receiving and expressing the co-introduced cell surface antigen.

Numerous enrichment handles may be used in the methods and instruments of the disclosure, including but not limited to various cell surface molecules linked to tag, e.g., a hemagglutinin (HA) tag, a FLAG tag, an SBP tag, and the like. In certain aspects, the tagged cell surface marker is modified to alter its activity, including but not limited to ΔTetherin-HA, ΔTetherin-FLAG, ΔTetherin-SBP and the like.

In some aspects, the enrichment handle can bind affinity ligands (e.g., engineered to contain an HA tag, a FLAG tag, an SBP tag, and the like). In some aspects, the enrichment handle can be a heterologous cell surface receptor (a cell surface receptor not generally present in the cell type to be edited) or autologous cell surface antigen with an engineered epitope tag. In specific aspects the methods use an editing selection cassette, e.g., a GFP-to-BFP editing cassette.

The disclosure also includes automated multi-module cell editing instruments with an enrichment module that performs enrichment methods including those described herein to increase the overall editing efficiency in a population of cells, e.g., mammalian cells.

One exemplary automated multi-module cell editing instrument of the disclosure includes a housing configured to house all or some of the modules, a receptacle configured to receive cells, one or more receptacles configured to receive nucleic acids, an editing machinery introduction module configured to introduce the nucleic acids and/or proteins into the cells, a recovery module configured to allow the cells to recover after introduction of the editing machinery, an enrichment module for enrichment of cells that have received the editing nucleic acids and/or nuclease, an editing module configured to allow the introduced nucleic acids to edit nucleic acids in the cells, and a processor configured to operate the automated multi-module cell editing instrument based on user input and/or selection of a pre-programmed script.

One exemplary automated multi-module cell editing instrument of the disclosure includes a housing configured to house all or some of the modules, a receptacle configured to receive cells and editing nucleic acids, an editing machinery introduction module configured to introduce the nucleic acids into the cells, a recovery module configured to allow the cells to recover after introduction of the editing machinery, an enrichment module for enrichment of cells that have received the editing nucleic acids and/or nuclease, an editing module configured to allow the introduced nucleic acids to edit nucleic acids in the cells, and a processor configured to operate the automated multi-module cell editing instrument based on user input and/or selection of a pre-programmed script.

One exemplary automated multi-module cell editing instrument of the disclosure includes a housing configured to house some or all of the modules, a receptacle configured to receive cells, at least one receptacle configured to receive nucleic acids for editing, a growth module configured to grow the cells, an editing machinery introduction module comprising a flow-through electroporator to introduce editing nucleic acids into the cells, an enrichment module for enrichment of cells that have received the editing nucleic acids and/or nuclease, an editing module configured to allow the editing nucleic acids to edit nucleic acids in the cells, and a processor configured to operate the automated multi-module cell editing instrument based on user input and/or selection of a pre-programmed script.

One exemplary automated multi-module cell editing instrument of the disclosure includes a housing configured to house some or all of the modules, a receptacle configured to receive cells and editing nucleic acids, a growth module configured to grow the cells, a filtration module configured to concentrate the cells and render the cells electrocompetent, an editing machinery introduction module comprising a flow-through electroporator to introduce editing nucleic acids into the cells, an enrichment module for enrichment of cells that have received the editing nucleic acids, an editing module configured to allow the cells to recover after electroporation and to allow the nucleic acids to edit the cells, and a processor configured to operate the automated multi-module cell editing instrument based on user input.

Optionally, the nucleic acids and/or cells are contained within a reagent cartridge, which is introduced into a receptacle of the instrument. Such cartridges for use with the present disclosure are described, e.g., in U.S. Pat. Nos. 10,376,889, 10,478,822, and 10,406,525, which are incorporated by reference herein for all purposes.

The methods described herein enable the user to obtain a population of cells with a much higher proportion of cells with precise, intended edits and fewer unedited and/or imprecisely edited cells. The present methods can result in 20%, 25%, 30%, 35%, 40%, 45%, 50%, 55%, 60%, 65%, 70%, 75%, 80%, 85%, 90% or more intended edits within a cell population.

Accordingly, in some aspects, the disclosure provides cell libraries created using the editing methods described herein in the disclosure.

In some aspects, the disclosure provides cell libraries created using an automated editing system for nickase-directed genome editing, wherein the system comprises a housing, a receptacle configured to receive cells and one or more rationally designed nucleic acids comprising sequences to facilitate nickase-directed genome editing events in the cells, a transformation unit for introduction of the nucleic acid(s) into the cells, an editing unit for allowing the nickase-directed genome editing events to occur in the cells, an enrichment module, and a processor-based system configured to operate the instrument based on user input, where the nickase-directed genome editing events created by the automated system result in a cell library comprising individual cells with rationally designed edits.

In some aspects, the disclosure provides cell libraries created using an automated editing system for nickase-directed genome editing, wherein the system comprises a housing, a cell receptacle configured to receive cells, a nucleic acid receptacle configured to receive one or more rationally designed nucleic acids comprising sequences to facilitate nickase-directed genome editing events in the cells, a transformation unit for introduction of the nucleic acid(s) into the cells, an editing unit for allowing the nickase-directed genome editing events to occur in the cells, and a processor based system configured to operate the instrument based on user input, where the nickase-directed genome editing events created by the automated system result in a cell library comprising individual cells with rationally designed edits.

These aspects and other features and advantages of the invention are described below in more detail.

DETAILED DESCRIPTION

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes. Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for all purposes, including but not limited to describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus (e.g., a target genomic DNA sequence or cellular target sequence) by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the genomic target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the genomic target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "nickase" as used herein refers to a nuclease that cuts one strand of a double-stranded DNA at a specific recognition nucleotide sequence.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible.

As used herein the term "selectable marker" refers to a gene introduced into a cell, which confers a trait suitable for artificial selection. General use selectable markers are well-known to those of ordinary skill in the art. For examples, selectable markers can use means that deplete a cell population to enrich for editing, and include ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 or other selectable markers may be employed. In addition, selectable markers include physical markers that confer a phenotype that can be utilized for physical or computations cell enrichment, e.g., optical selectable markers such as fluorescent proteins (e.g., green fluorescent protein, blue fluorescent protein) and cell surface handles.

The term "specifically binds" as used herein includes an interaction between two molecules, e.g., an engineered peptide antigen and a binding target, with a binding affinity represented by a dissociation constant of about $10^{-7}$M, about $10^{-8}$M, about $10^{-9}$ M, about $10^{-10}$ M, about $10^{-11}$M, about $10^{-12}$M, about $10^{-13}$M, about $10^{-14}$M or about $10^{-15}$M.

The terms "target genomic DNA sequence", "cellular target sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. In the present disclosure, the term "editing vector" includes a coding sequence for a nuclease, a gRNA sequence to be transcribed, and a donor DNA sequence. In other embodiments, however, two vectors—an engine vector comprising the coding sequence for a nuclease, and an editing vector, comprising the gRNA sequence to be transcribed and the donor DNA sequence—may be used.

BRIEF DESCRIPTION OF THE DRAWINGS

The foregoing and other features and advantages of the present invention will be more fully understood from the following detailed description of illustrative embodiments taken in conjunction with the accompanying drawings in which:

FIGS. 1A-1D depict an automated multi-module instrument and components thereof with which to practice the recursive editing methods as taught herein.

FIGS. 20A and 20B are a graph and table showing how MACS bead concentrations during enrichment affect the relative proportions of ΔTetherin-HA enriched cells.

THE INVENTION IN GENERAL

Figure 1A:
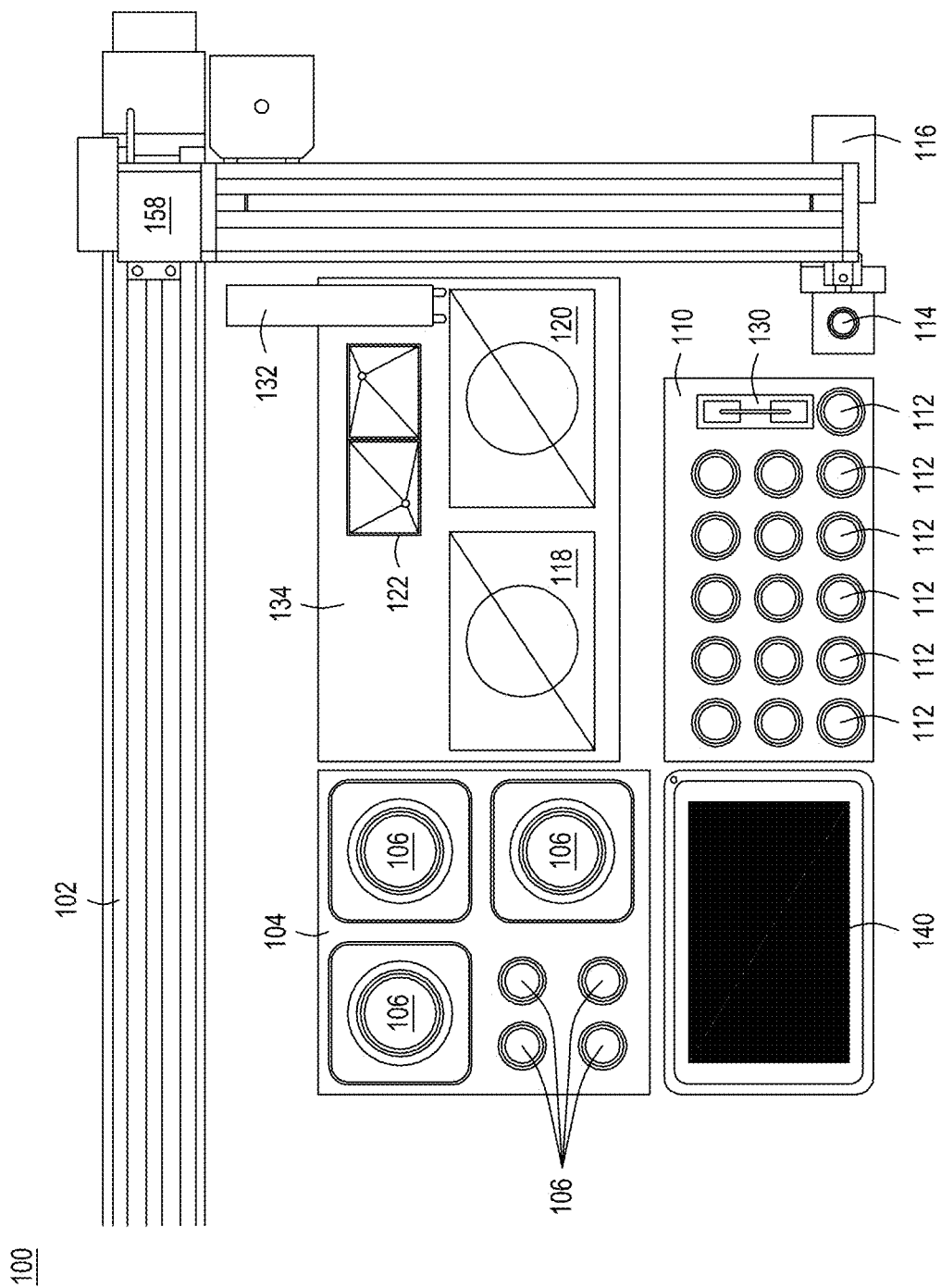

This disclosure is directed to methods and instruments for improving precise editing in a population of cells. Various cellular mechanisms may be used in the editing process, including non-homologous end joining (NHEJ) repair, base editing, microhomology-directed repair (MMEJ) and/or homology-directed repair (HDR).

In specific aspects, the methods and instruments improve editing via homology-directed repair (HDR); accordingly, in specific aspects, the disclosure provides methods of improving HDR in mammalian cells. In more specific aspects, the disclosure provides methods of improving HDR in human cells. In certain specific aspects, the disclosure provides methods of improving HDR in human pluripotent cells, e.g., induced pluripotent stem cells.

In certain aspects, the disclosure provides enrichment of co-introduced nucleic acids for the enrichment of cells that have received the editing components necessary for nucleic acid-directed editing, e.g., using specific selection of cells that have been transfected with a plasmid containing a nucleic acid encoding a donor nucleic acid and/or a guide nucleic acid, and optionally a nuclease.

More specifically, enrichment of a subpopulation of cells with the highest amount of reporter expression enriches for a population of cells that undergo gene editing at higher rates than unenriched populations or subpopulations with relatively lower levels of reporter expression.

In specific aspects, the disclosure is directed to automated methods of increasing editing efficiencies using co-introduction of nucleic acids encoding editing machinery and a cell surface selection handle. In specific aspects, the co-introduction of nucleic acids occurs in a multi-module automated instrument, as described in more detail herein.

In certain aspects, the disclosure provides methods of improving homology-directed repair (HDR) using proteins that are a combination of an RNA-directed nuclease and an enzymatic activity from a different protein, e.g., replication inhibition, reverse transcriptase activity, transcription enhancement activity, and the like. In preferred aspects, these nuclease fusion proteins have a nickase function, and thus result in a nick on a single strand of the DNA to be edited instead of a double stranded break.

The editing nuclease fusion proteins can be used with editing nucleic acids such as those found, e.g., in U.S. Pat. No. 9,982,278 and related patents. Such nucleic acids encoding a gRNA comprising a region complementary to a target region of a nucleic acid in one or more cells covalently linked to an editing cassette comprising a region homologous to the target region in the one or more cells with a mutation of at least one nucleotide relative to the target region in the one or more cells. These nucleic acids can optionally include a protospacer and/or a barcode. The editing methods can involve one or more sets of these nucleic acids, and result in two or more nicks in the target region for the intended edit. Examples of such methods include, but are not limited to, those described in Liu et al (Nature, 2019 December; 576(7785):149-157).

In certain preferred embodiments, the methods employ a novel method termed "CREATE Fusion Editing". "CREATE Fusion Editing" is a novel technique that uses a nuclease editing enzyme having nickase activity in conjunction with one or more nucleic acids to facilitate editing. In specific aspects, CREATE Fusion Editing methods utilize an editing fusion protein (e.g., a protein having CRISPR targeting activity and reverse transcriptase activity) and a nucleic acid encoding one or more gRNAs comprising a region complementary to a target region of a nucleic acid. The one or more gRNAs are covalently linked to an editing cassette comprising a region homologous to the target region having a mutation of at least one nucleotide relative to the target region for the intended edit in the one or more cells. Optionally, the nucleic acid may further comprise a protospacer adjacent motif (PAM) mutation and/or a barcode indicative of the intended mutation in the target region. Further description of the use of such CREATE nucleic acids can be found, e.g., in U.S. Pat. No. 9,982,278, which is incorporated by reference herein for all purposes.

The use of a single gRNA to achieve editing rates of 30% or greater has numerous benefits over the dual nick system described in Liu et al. supra, that they taught was needed to achieve such editing rates in mammalian cells. For example, eliminating the need for a second nick allows much greater scalability for multiplexed genome editing, as each cell requires only one editing construct to target the site of the intended edit. This also increases the number of sites in the genome of cells that are available for editing, enhancing the potential design and coverage of a library of editing vectors to be introduced to a cell population. The use of a single gRNA as described herein will also decrease indel formation as compared to a dual nick system, and is predicted to reduce off target effects, e.g., due to specificity issued from the nickase activity.

In some aspects, an edit in the nuclease binding seed region can be utilized to render a site nuclease resistant, preventing additional cutting using the nuclease (e.g., a nuclease fusion protein containing nicking activity)

In specific aspects, the CREATE Fusion methods can utilize a fusion protein having nickase activity and a single gRNA to achieve high efficiency editing, two-fold or more over the techniques taught in Liu et al, supra. By creating a single nick in the target region the methods of the present disclosure were able to achieve editing efficiencies of over 20%, including precise editing rates of up to 45%, in mammalian cells without enrichment. Thus, the single nick system disclosed herein which was able to achieve the high levels of editing efficiency previously described only utilizing a dual nick system.

Figure 7:
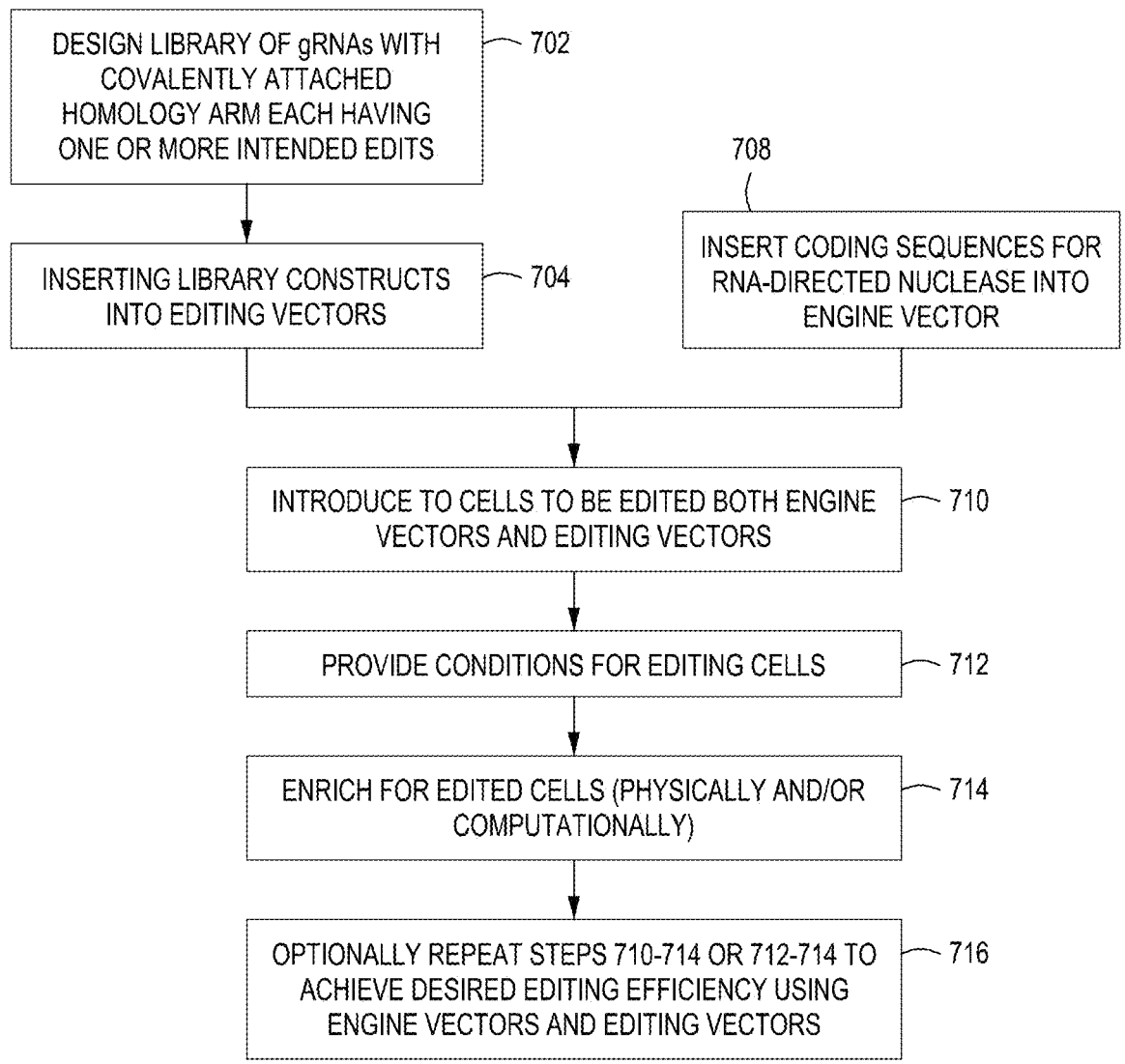
FIG. 7 is a diagram showing a first set of exemplary workflows for carrying out editing and selection protocols of the disclosure.
Figure 8:
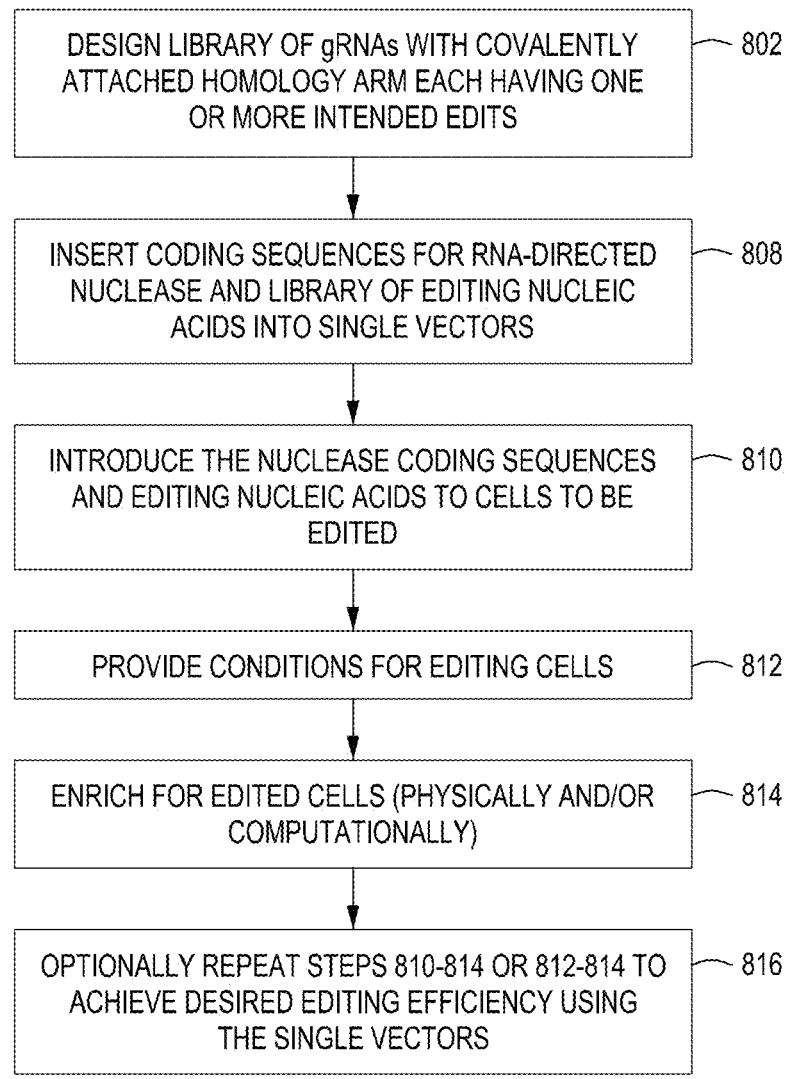
FIG. 8 is a diagram showing a second set of exemplary workflows for carrying out editing and selection protocols of the disclosure.

Certain workflows for carrying out CREATE Fusion Editing are summarized in FIGS. 7 and 8. In certain preferred embodiments, these workflows are carried out using an automated system or instrument, e.g., a multi-module instrument and set forth in the disclosure.

Figure 9:
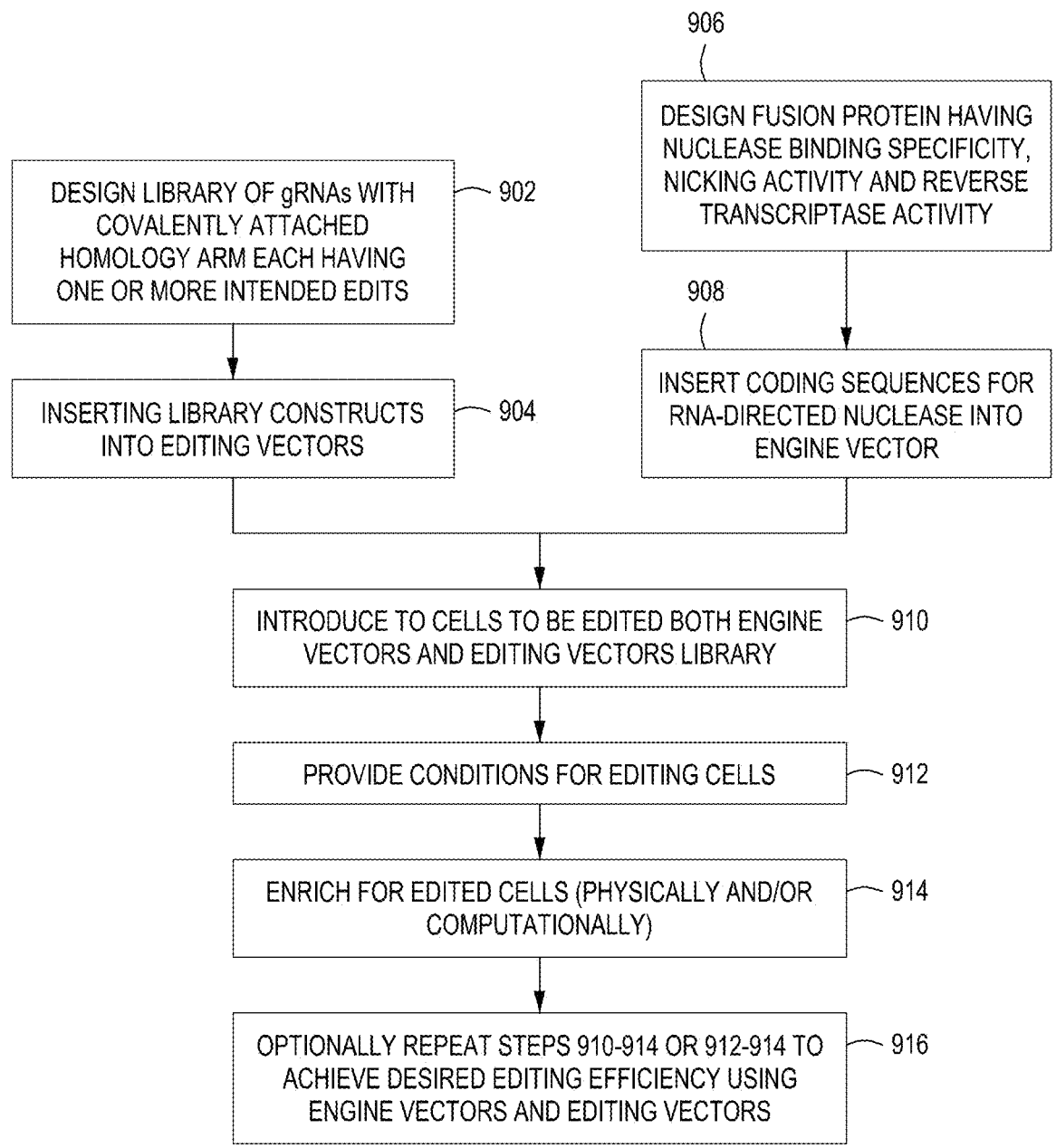
FIG. 9 is a diagram showing a first set of exemplary workflows for carrying out CREATE Fusion Editing protocols of the disclosure.

Without being bound by a particular mechanism, the editing machinery can be allowed to persist for several cell divisions. As shown in FIG. 9, this editing cycle in the cell population allows a higher percentage of the cells to be edited using the introduced CREATE Fusion Editing machinery.

Nuclease-Directed Genome Editing Generally

The compositions and methods described herein are employed to perform nuclease-directed genome editing to introduce desired edits to a population of mammalian cells. In some embodiments, a single edit is introduced in a single round of editing. In some embodiments, multiple edits are introduced in a single round of editing using simultaneous editing, e.g., the introduction of two or more edits on a single vector. In some embodiments, recursive cell editing is performed where edits are introduced in successive rounds of editing.

A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette. For additional information regarding editing cassettes, see, e.g., U.S. Pat. Nos. 10,240,167; 10,266,849; 9,982,278; 10,351,877; 10,364,442; and 10,435,715; and U.S. Ser. No. 16/275,465, filed 14 Feb. 2019, all of which are incorporated by reference herein for all purposes.

A guide nucleic acid comprises a guide sequence, where the guide sequence is a polynucleotide sequence having sufficient complementarity (i.e homology) with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to the mammalian cell, or in vitro. For example, the target sequence can be a polynucleotide residing in the nucleus of the mammalian cell. A target sequence can be a sequence encoding a gene product (e.g., a protein) or a non-coding sequence (e.g., a regulatory polynucleotide, an intron, a PAM, a control sequence, or "junk" DNA).

The guide nucleic acid may be and preferably is part of an editing cassette that encodes the donor nucleic acid that targets a cellular target sequence. Alternatively, the guide nucleic acid may not be part of the editing cassette and instead may be encoded on the editing vector backbone. For example, a sequence coding for a guide nucleic acid can be assembled or inserted into a vector backbone first, followed by insertion of the donor nucleic acid in, e.g., an editing cassette. In other cases, the donor nucleic acid in, e.g., an editing cassette can be inserted or assembled into a vector backbone first, followed by insertion of the sequence coding for the guide nucleic acid. Preferably, the sequence encoding the guide nucleic acid and the donor nucleic acid are located together in a rationally-designed editing cassette and are simultaneously inserted or assembled via gap repair into a linear plasmid or vector backbone to create an editing vector. In some aspects, a PCR amplicon of the editing cassette can be used for editing.

The target sequence is associated with a proto-spacer mutation (PAM), which is a short nucleotide sequence recognized by the gRNA/nuclease complex. The precise preferred PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease.

In certain embodiments, the genome editing of a cellular target sequence both introduces a desired DNA change to a cellular target sequence, e.g., the genomic DNA of a cell, and removes, mutates, or renders inactive a proto-spacer mutation (PAM) region in the cellular target sequence. Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

As for the nuclease component of the nucleic acid-guided nuclease editing system, a polynucleotide sequence encoding the nucleic acid-guided nuclease can be codon optimized for expression in particular mammalian cell types, such as stem cells. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/Cpf1, MAD2, or MAD7 or other MADzymes. As with the guide nucleic acid, the nuclease is encoded by a DNA sequence on a vector and optionally is under the control of an inducible promoter. In some embodiments, the promoter may be separate from but the same as the promoter controlling transcription of the guide nucleic acid; that is, a separate promoter drives the transcription of the nuclease and guide nucleic acid sequences but the two promoters may be the same type of promoter. Alternatively, the promoter controlling expression of the nuclease may be different from the promoter controlling transcription of the guide nucleic acid; that is, e.g., the nuclease may be under the control of, e.g., the pTEF promoter, and the guide nucleic acid may be under the control of the, e.g., pCYC1 promoter.

Another component of the nucleic acid-guided nuclease system is the donor nucleic acid comprising homology to the cellular target sequence. The donor nucleic acid is on the same vector and even in the same editing cassette as the guide nucleic acid and preferably is (but not necessarily is) under the control of the same promoter as the editing gRNA (that is, a single promoter driving the transcription of both the editing gRNA and the donor nucleic acid). The donor nucleic acid is designed to serve as a template for homologous recombination with a cellular target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length, and up to 2, 3, 4, 5, 6, 7, 8, 9, 10, 11, 12, 13 and up to 20 kb in length if combined with a dual gRNA architecture as described in U.S. Ser. No. 62/869,240, filed 1 Jul. 2019. In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm). When optimally aligned, the donor nucleic acid overlaps with (is complementary to) the cellular target sequence by, e.g., about 20, 25, 30, 35, 40, 50, 60, 70, 80, 90 or more nucleotides. In many embodiments, the donor nucleic acid comprises two homology arms (regions complementary to the cellular target sequence) flanking the mutation or difference between the donor nucleic acid and the cellular target sequence. The donor nucleic acid comprises at least one mutation or alteration compared to the cellular target sequence, such as an insertion, deletion, modification, or any combination thereof compared to the cellular target sequence.

As described in relation to the gRNA, the donor nucleic acid can be provided as part of a rationally-designed editing cassette, which is inserted into an editing plasmid backbone where the editing plasmid backbone may comprise a promoter to drive transcription of the editing gRNA and the donor DNA when the editing cassette is inserted into the editing plasmid backbone. Moreover, there may be more than one, e.g., two, three, four, or more editing gRNA/donor nucleic acid rationally-designed editing cassettes inserted into an editing vector; alternatively, a single rationally-designed editing cassette may comprise two to several editing gRNA/donor DNA pairs, where each editing gRNA is under the control of separate different promoters, separate like promoters, or where all gRNAs/donor nucleic acid pairs are under the control of a single promoter. In some embodiments the promoter driving transcription of the editing gRNA and the donor nucleic acid (or driving more than one editing gRNA/donor nucleic acid pair) is optionally an inducible promoter.

In addition to the donor nucleic acid, an editing cassette may comprise one or more primer sites. The primer sites can be used to amplify the editing cassette by using oligonucleotide primers; for example, if the primer sites flank one or more of the other components of the editing cassette. In addition, the editing cassette may comprise a barcode. A barcode is a unique DNA sequence that corresponds to the donor DNA sequence such that the barcode can identify the edit made to the corresponding cellular target sequence. The barcode typically comprises four or more nucleotides. In some embodiments, the editing cassettes comprise a collection or library editing gRNAs and of donor nucleic acids representing, e.g., gene-wide or genome-wide libraries of editing gRNAs and donor nucleic acids. The library of editing cassettes is cloned into vector backbones where, e.g., each different donor nucleic acid is associated with a different barcode. Also, in preferred embodiments, an editing vector or plasmid encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs, particularly as an element of the nuclease sequence. In some embodiments, the engineered nuclease comprises NLSs at or near the amino-terminus, NLSs at or near the carboxy-terminus, or a combination.

Cells with a stably integrated genomic copy of the GFP gene can enable phenotypic detection of genomic edits of different classes (NHEJ, HDR, no edit) by flow cytometry, fluorescent cell imaging, or genotypic detection by sequencing of the genome-integrated GFP gene. Lack of editing, or perfect repair of cut events in the GFP gene result in cells that remain GFP-positive. Cut events that are repaired by the Non-Homologous End-Joining (NHEJ) pathway often result in nucleotide insertion or deletion events (Indel). These Indel edits often result in frame-shift mutations in the coding sequence that cause loss of GFP gene expression and fluorescence. Cut events that are repaired by the Homology-Directed Repair (HDR) pathway, using the GFP to BFP HDR donor as a repair template result in conversion of the cell fluorescence profile from that of GFP to that of BFP.

Editing Cassette

The editing cassette used was a plasmid that mediates expression of a gRNA that targets the nuclease to a specific DNA sequence. The editing cassette plasmid can also have a DNA sequence (e.g., HDR donor) to provide a template for targeted insertions, deletions, or nucleotide swaps proximal to the nuclease-targeted cut site. In one example, the editing cassette plasmid expresses a gRNA targeting a stably integrated genomic copy of the GFP gene and provides an HDR donor that mediates nucleotide swaps which convert the amino acid coding sequence of GFP to that of BFP.

An RNA-guided nuclease (e.g., Cas9, Cpf1, MAD7) can be delivered to the cell by means of a nuclease-encoding expression plasmid, nuclease-encoding mRNA, recombinant nuclease protein, or by generation of a nuclease-expressing stable cell line. In this specific example, the MAD7 nuclease was delivered by means of a nuclease-encoding expression plasmid.

Editing cassette plasmid and nuclease can be delivered to the target cell by traditional mammalian cell transfection techniques.

Figure 4A:
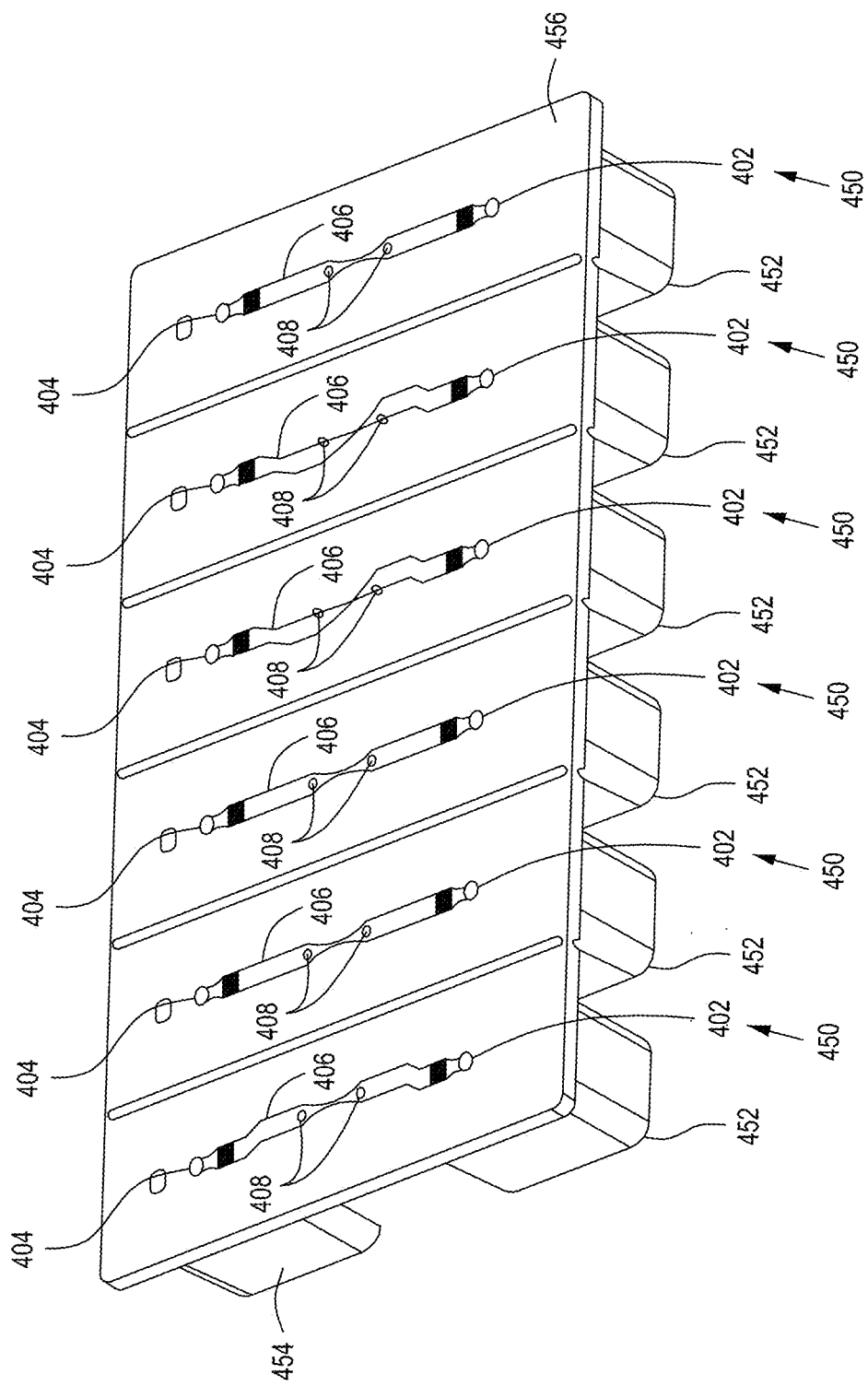
FIG. 4A shows a flow-through electroporation device exemplary (here, there are six such devices co-joined).

Automated Cell Editing Instruments and Modules to Perform Nucleic Acid-Guided Nuclease Editing Automated Cell Editing Instruments FIG. 1A depicts an exemplary automated multi-module cell processing instrument 100 to, e.g., perform one of the exemplary workflows comprising a split protein reporter system as described herein. The instrument 100, for example, may be and preferably is designed as a stand-alone desktop instrument for use within a laboratory environment. The instrument 100 may incorporate a mixture of reusable and disposable components for performing the various integrated processes in conducting automated genome cleavage and/or editing in cells without human intervention. Illustrated is a gantry 102, providing an automated mechanical motion system (actuator) (not shown) that supplies XYZ axis motion control to, e.g., an automated (i.e., robotic) liquid handling system 158 including, e.g., an air displacement pipettor 132 which allows for cell processing among multiple modules without human intervention. In some automated multi-module cell processing instruments, the air displacement pipettor 132 is moved by gantry 102 and the various modules and reagent cartridges remain stationary; however, in other embodiments, the liquid handling system 158 may stay stationary while the various modules and reagent cartridges are moved. Also included in the automated multi-module cell processing instrument 100 are reagent cartridges 110 comprising reservoirs 112 and editing machinery introduction module 130 (e.g., a flow-through electroporation device as described in detail in relation to FIGS. 4A-4D), as well as wash reservoirs 106, cell input reservoir 151 and cell output reservoir 153. The wash reservoirs 106 may be configured to accommodate large tubes, for example, wash solutions, or solutions that are used often throughout an iterative process. Although two of the reagent cartridges 110 comprise a wash reservoir 106 in FIG. 1A, the wash reservoirs instead could be included in a wash cartridge where the reagent and wash cartridges are separate cartridges. In such a case, the reagent cartridge 110 and wash cartridge 104 may be identical except for the consumables (reagents or other components contained within the various inserts) inserted therein. Note that an exemplary reagent cartridge is illustrated in FIGS. 5A and 5B.

In some implementations, the reagent cartridges 110 are disposable kits comprising reagents and cells for use in the automated multi-module cell processing/editing instrument 100. For example, a user may open and position each of the reagent cartridges 110 comprising various desired inserts and reagents within the chassis of the automated multi-module cell editing instrument 100 prior to activating cell processing. Further, each of the reagent cartridges 110 may be inserted into receptacles in the chassis having different temperature zones appropriate for the reagents contained therein.

Also illustrated in FIG. 1A is the robotic liquid handling system 158 including the gantry 102 and air displacement pipettor 132. In some examples, the robotic handling system 158 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips may be provided in a pipette transfer tip supply (not shown) for use with the air displacement pipettor 132.

Inserts or components of the reagent cartridges 110, in some implementations, are marked with machine-readable indicia (not shown), such as bar codes, for recognition by the robotic handling system 158. For example, the robotic liquid handling system 158 may scan one or more inserts within each of the reagent cartridges 110 to confirm contents. In other implementations, machine-readable indicia may be marked upon each reagent cartridge 110, and a processing system (not shown, but see element 137 of FIG. 1B) of the automated multi-module cell editing instrument 100 may identify a stored materials map based upon the machine-readable indicia. In the embodiment illustrated in FIG. 1A, a cell growth module comprises two cell growth vials 118, 120 (described in greater detail below in relation to FIGS. 2A-2D). Additionally seen is the TFF module 122 (described above in detail in relation to FIGS. 3A-3L). Additionally seen is an enrichment module 140. Also note the placement of three heatsinks 155.

Figure 1B:
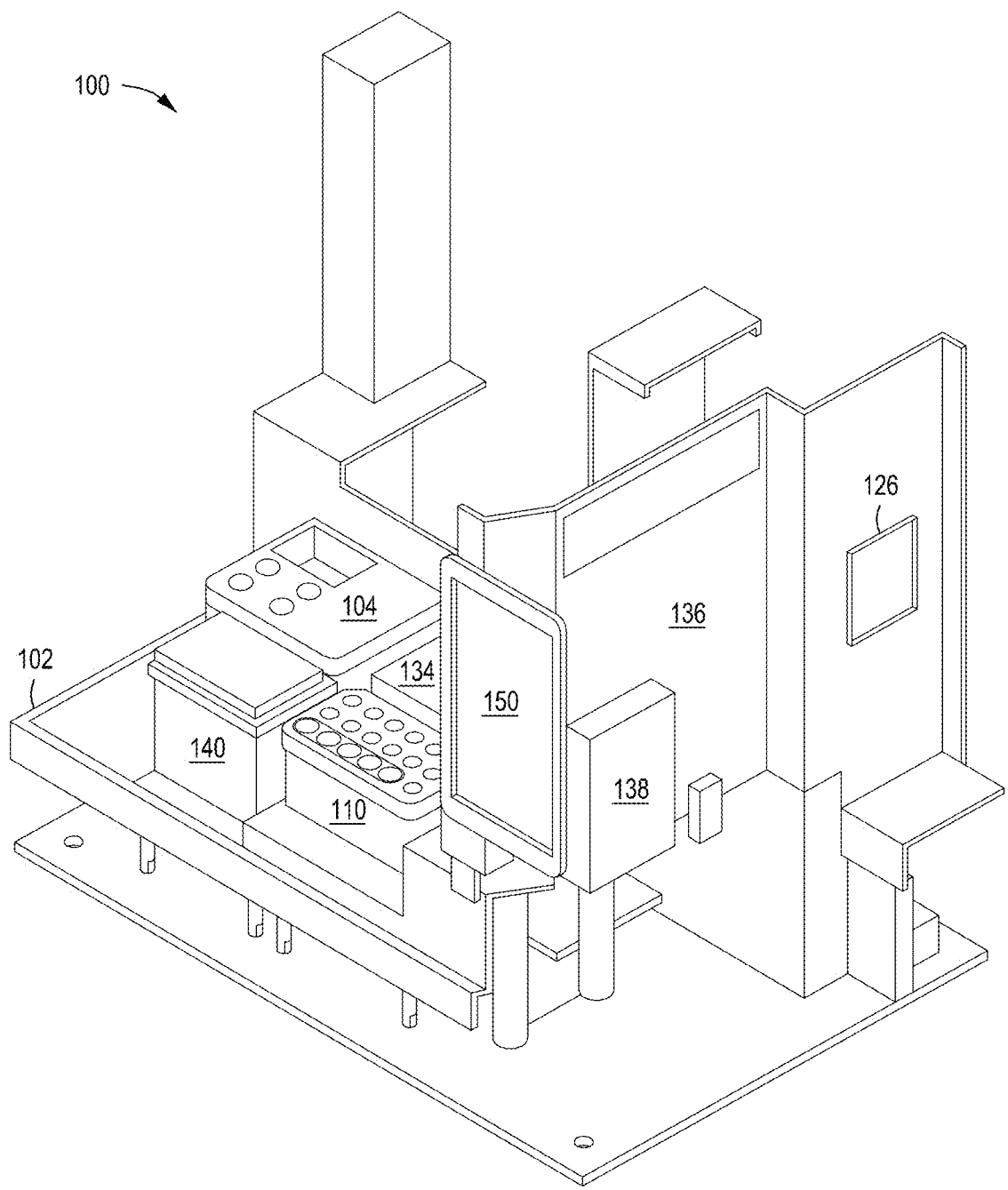

FIG. 1B is a simplified representation of the contents of the exemplary multi-module cell processing instrument 100 depicted in FIG. 1A. Cartridge-based source materials (such as in reagent cartridges 110), for example, may be positioned in designated areas on a deck of the instrument 100 for access by an air displacement pipettor 132. The deck of the multi-module cell processing instrument 100 may include a protection sink such that contaminants spilling, dripping, or overflowing from any of the modules of the instrument 100 are contained within a lip of the protection sink. Also seen are reagent cartridges 110, which are shown disposed with thermal assemblies 111 which can create temperature zones appropriate for different regions. Note that one of the reagent cartridges also comprises a flow-through electroporation device 130 (FTEP), served by FTEP interface (e.g., manifold arm) and actuator 131. Also seen is TFF module 122 with adjacent thermal assembly 125, where the TFF module is served by TFF interface (e.g., manifold arm) and actuator 133. Thermal assemblies 125, 135, and 145 encompass thermal electric devices such as Peltier devices, as well as heatsinks, fans and coolers. The rotating growth vials 118, 120 are within a growth module 134, where the growth module is served by two thermal assemblies 135. An enrichment module is seen at 140, where the enrichment module is served by selection interface (e.g., manifold arm) and actuator 147. Also seen in this view is touch screen display 101, display actuator 103, illumination 105 (one on either side of multi-module cell processing instrument 100), and cameras 139 (one illumination device on either side of multi-module cell processing instrument 100). Finally, element 137 comprises electronics, such as circuit control boards, high-voltage amplifiers, power supplies, and power entry; as well as pneumatics, such as pumps, valves and sensors.

FIG. 1C illustrates a front perspective (door open) view of multi-module cell processing instrument 100 for use in as a desktop version of the automated multi-module cell editing instrument 100. For example, a chassis 190 may have a width of about 24-48 inches, a height of about 24-48 inches and a depth of about 24-48 inches. Chassis 190 may be and preferably is designed to hold all modules and disposable supplies used in automated cell processing and to perform all processes required without human intervention; that is, chassis 190 is configured to provide an integrated, standalone automated multi-module cell processing instrument. As illustrated in FIG. 1C, chassis 190 includes touch screen display 101, cooling grate 164, which allows for air flow via an internal fan (not shown). The touch screen display provides information to a user regarding the processing status of the automated multi-module cell editing instrument 100 and accepts inputs from the user for conducting the cell processing. In this embodiment, the chassis 190 is lifted by adjustable feet 170a, 170b, 170c and 170d (feet 170a-170c are shown in this FIG. 1C). Adjustable feet 170a-170d, for example, allow for additional air flow beneath the chassis 290.

Inside the chassis 190, in some implementations, will be most or all of the components described in relation to FIGS. 1A and 1B, including the robotic liquid handling system disposed along a gantry, reagent cartridges 110 including a flow-through electroporation device, rotating growth vials 118, 120 in a cell growth module 134, a tangential flow filtration module 122, an enrichment module 140 as well as interfaces and actuators for the various modules. In addition, chassis 190 houses control circuitry, liquid handling tubes, air pump controls, valves, sensors, thermal assemblies (e.g., heating and cooling units) and other control mechanisms. For examples of multi-module cell editing instruments, see U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; and U.S. Ser. No. 16/412,195, filed 14 May 2019; Ser. No. 16/571,091, filed 14 Sep. 2019; and Ser. No. 16/666,964, filed 29 Oct. 2019, all of which are herein incorporated by reference in their entirety for all purposes.

The Rotating Cell Growth Module

Figure 2A:
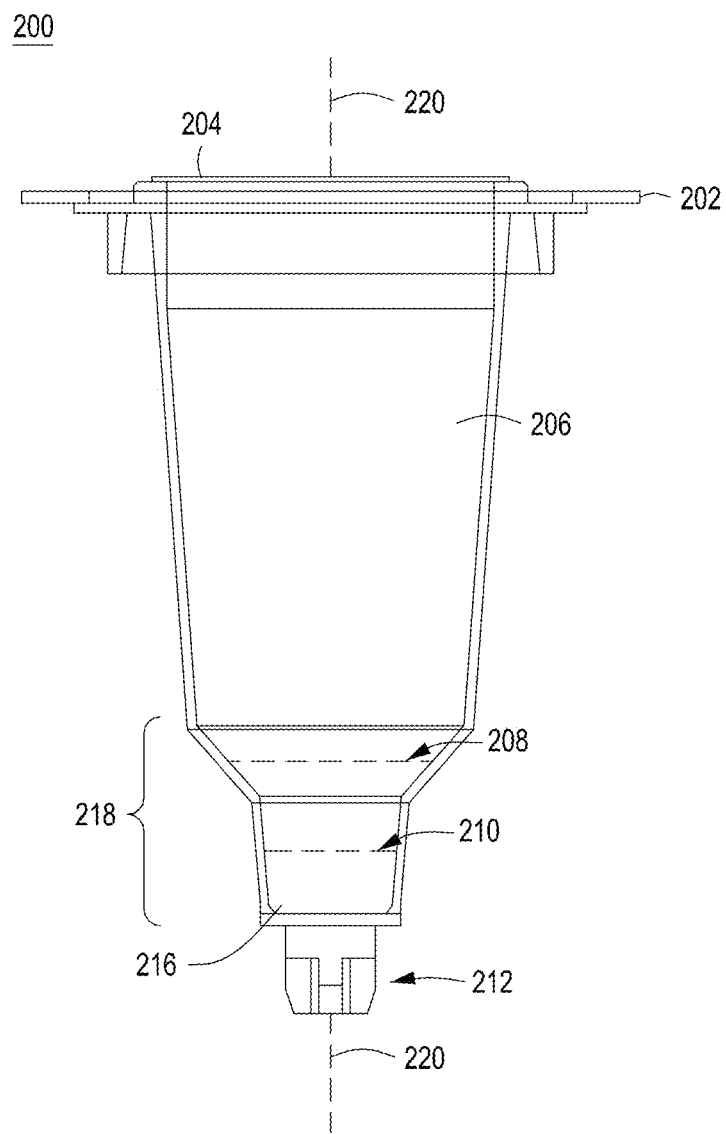
FIG. 2A depicts one embodiment of a rotating growth vial for use with the cell growth module described herein.

FIG. 2A shows one embodiment of a rotating growth vial 200 for use with the cell growth device described herein configured to grow various cell types including microbial and mammalian cells lines and primary or generated stem cells (e.g., induced pluripotent stem cells, hematopoietic stem cells, embryonic stem cells and the like). The rotating growth vial is an optically-transparent container having an open end 204 for receiving liquid media and cells, a central vial region 206 that defines the primary container for growing cells, a tapered-to-constricted region 218 defining at least one light path 210, a closed end 216, and a drive engagement mechanism 212. The rotating growth vial has a central longitudinal axis 220 around which the vial rotates, and the light path 210 is generally perpendicular to the longitudinal axis of the vial. The first light path 210 is positioned in the lower constricted portion of the tapered-to-constricted region 218. Optionally, some embodiments of the rotating growth vial 200 have a second light path 208 in the tapered region of the tapered-to-constricted region 218. Both light paths in this embodiment are positioned in a region of the rotating growth vial that is constantly filled with the cell culture (cells+growth media) and is not affected by the rotational speed of the growth vial. The first light path 210 is shorter than the second light path 208 allowing for sensitive measurement of OD values when the OD values of the cell culture in the vial are at a high level (e.g., later in the cell growth process), whereas the second light path 208 allows for sensitive measurement of OD values when the OD values of the cell culture in the vial are at a lower level (e.g., earlier in the cell growth process). Also shown is lip 202, which allows the rotating growth vial to be seated in a growth module (not shown) and further allows for easy handling for the user.

In some configurations of the rotating growth vial, the rotating growth vial has two or more "paddles" or interior features disposed within the rotating growth vial, extending from the inner wall of the rotating growth vial toward the center of the central vial region. In some aspects, the width of the paddles or features varies with the size or volume of the rotating growth vial, and may range from $\frac{1}{20}$ to just over $\frac{1}{3}$ the diameter of the rotating growth vial, or from $\frac{1}{15}$ to $\frac{1}{4}$ the diameter of the rotating growth vial, or from $\frac{1}{10}$ to $\frac{1}{5}$ the diameter of the rotating growth vial. In some aspects, the length of the paddles varies with the size or volume of the rotating growth vial, and may range from $\frac{4}{5}$ to $\frac{1}{4}$ the length of the main body of the rotating growth vial, or from $\frac{3}{4}$ to $\frac{1}{3}$ the length of the main body of the rotating growth vial, or from $\frac{1}{2}$ to $\frac{1}{3}$ the length of the main body of the rotating growth vial. In other aspects, there may be concentric rows of raised features disposed on the inner surface of the main body of the rotating growth vial arranged horizontally or vertically; and in other aspects, there may be a spiral configuration of raised features disposed on the inner surface of the main body of the rotating growth vial. In alternative aspects, the concentric rows of raised features or spiral configuration may be disposed upon a post or center structure of the rotating growth vial. Though described above as having two paddles, the rotating growth vial may comprise 3, 4, 5, 6 or more paddles, and up to 20 paddles. The number of paddles will depend upon, e.g., the size or volume of the rotating growth vial. The paddles may be arranged symmetrically as single paddles extending from the inner wall of the vial into the interior of the vial, or the paddles may be symmetrically arranged in groups of 2, 3, 4 or more paddles in a group (for example, a pair of paddles opposite another pair of paddles) extending from the inner wall of the vial into the interior of the vial. In another embodiment, the paddles may extend from the middle of the rotating growth vial out toward the wall of the rotating growth vial, from, e.g., a post or other support structure in the interior of the rotating growth vial.

The drive engagement mechanism 212 engages with a motor (not shown) to rotate the vial. In some embodiments, the motor drives the drive engagement mechanism 212 such that the rotating growth vial is rotated in one direction only, and in other embodiments, the rotating growth vial is rotated in a first direction for a first amount of time or periodicity, rotated in a second direction (i.e., the opposite direction) for a second amount of time or periodicity, and this process may be repeated so that the rotating growth vial (and the cell culture contents) are subjected to an oscillating motion. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial may be oscillated at a first periodicity (e.g., every 60 seconds), and then a later stage of cell growth the rotating growth vial may be oscillated at a second periodicity (e.g., every one second) different from the first periodicity.

The rotating growth vial 200 may be specifically tailored for the growth of particular cell types. For example, $O_2$ and/or $CO_2$ can be specifically monitored or controlled, and the rotating growth vial may be designed and OD measurement modified to be compatible with use of specific carrier substrates for growth of adherent cells.

The rotating growth vial 200 may be reusable or, preferably, the rotating growth vial is consumable. In some embodiments, the rotating growth vial is consumable and is presented to the user pre-filled with growth medium, where the vial is hermetically sealed at the open end 204 with a foil seal. A medium-filled rotating growth vial packaged in such a manner may be part of a kit for use with a stand-alone cell growth device or with a cell growth module that is part of an automated multi-module cell processing instrument. To introduce cells into the vial, a user need only pipette up a desired volume of cells and use the pipette tip to punch through the foil seal of the vial. Open end 204 may optionally include an extended lip 202 to overlap and engage with the cell growth device (not shown). In automated systems, the rotating growth vial 200 may be tagged with a barcode or other identifying means that can be read by a scanner or camera that is part of the automated system (not shown).

The volume of the rotating growth vial 200 and the volume of the cell culture (including growth medium) may vary greatly, but the volume of the rotating growth vial 200 must be large enough for the cell culture in the growth vial to get proper aeration while the vial is rotating. In practice, the volume of the rotating growth vial 200 may range from 1-250 ml, 2-100 ml, from 5-80 ml, 10-50 ml, or from 12-35 ml. Likewise, the volume of the cell culture (cells+growth media) should be appropriate to allow proper aeration in the rotating growth vial. Thus, the volume of the cell culture should be approximately 10-85% of the volume of the growth vial or from 20-60% of the volume of the growth vial. For example, for a 35 ml growth vial, the volume of the cell culture would be from about 4 ml to about 27 ml, or from 7 ml to about 21 ml.

The rotating growth vial 200 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include glass, polyvinyl chloride, polyethylene, polyamide, polyethylene, polypropylene, polycarbonate, poly(methyl methacrylate) (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 2B:
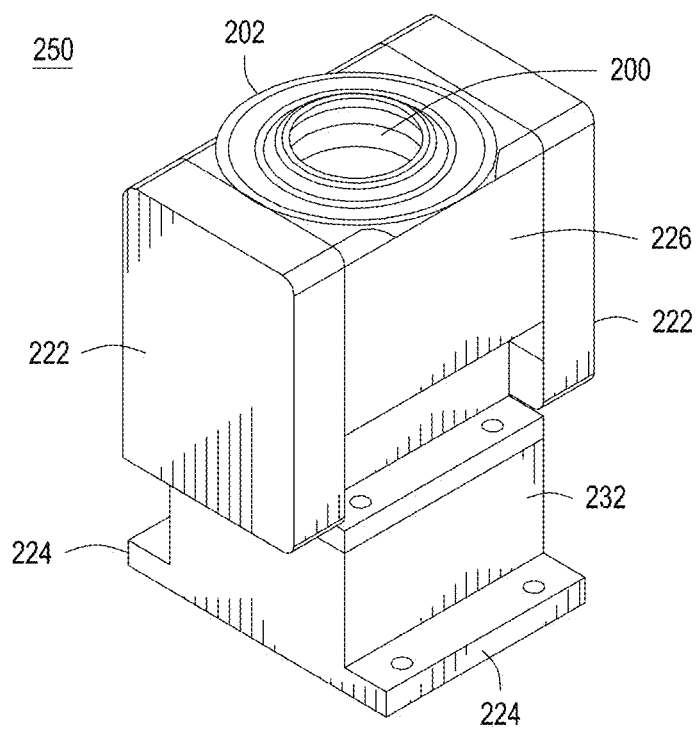
FIG. 2B illustrates a perspective view of one embodiment of a rotating growth vial in a cell growth module.
Figure 2C:
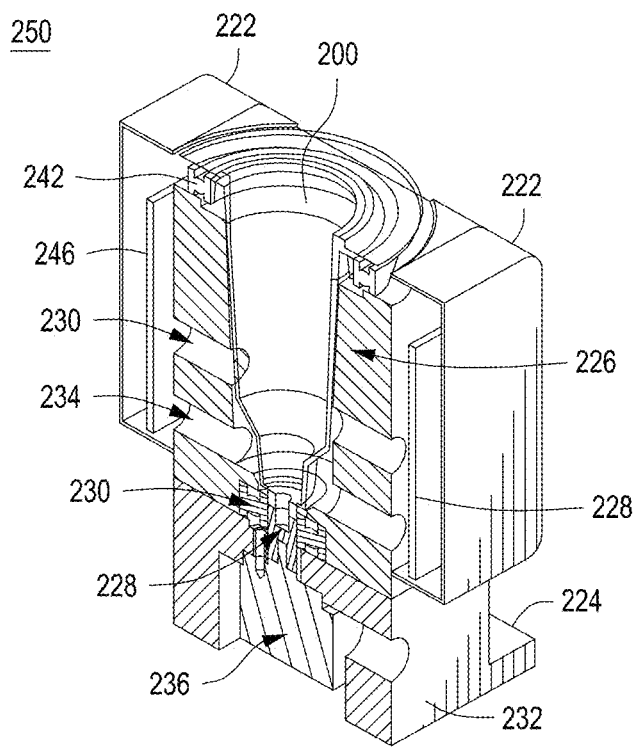
FIG. 2C depicts a cut-away view of the cell growth module from FIG. 2B.
Figure 2D:
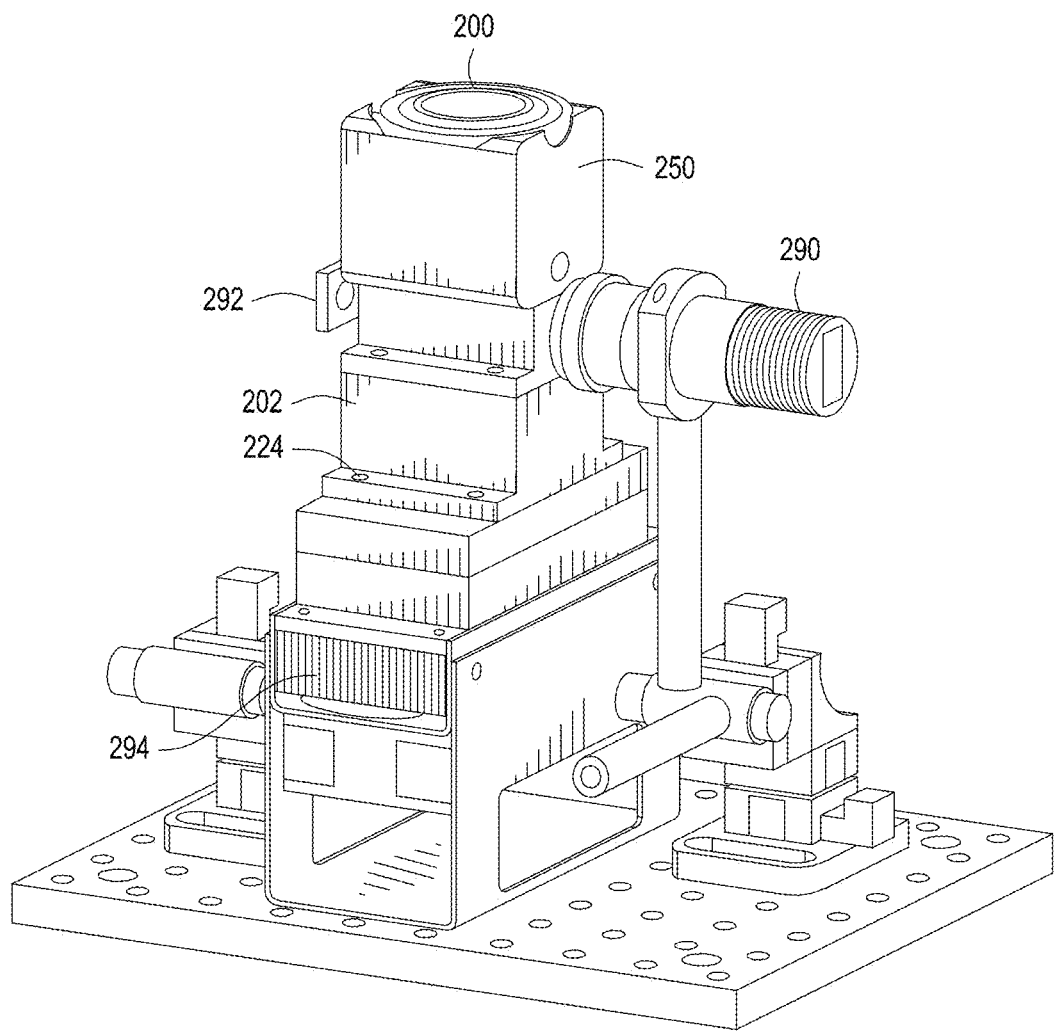
FIG. 2D illustrates the cell growth module of FIG. 2B coupled to LED, detector, and temperature regulating components.

FIGS. 2B-2D show an embodiment of a cell growth module 250 comprising a rotating growth vial 200. FIG. 2B is a perspective view of one embodiment of a cell growth device 250. FIG. 2C depicts a cut-away view of the cell growth device 250 from FIG. 2B. In both figures, the rotating growth vial 200 is seen positioned inside a main housing 226 with the extended lip 202 of the rotating growth vial 200 extending above the main housing 226. Additionally, end housings 222, a lower housing 232, and flanges 224 are indicated in both figures. Flanges 224 are used to attach the cell growth device to heating/cooling means or other structure (not shown). FIG. 2C depicts additional detail. In FIG. 2C, upper bearing 242 and lower bearing 230 are shown positioned in main housing 226. Upper bearing 242 and lower bearing 230 support the vertical load of rotating growth vial 200. Lower housing 232 contains the drive motor 236. The cell growth device of FIG. 2C comprises two light paths: a primary light path 234, and a secondary light path 230. Light path 234 corresponds to light path 210 positioned in the constricted portion of the tapered-to-constricted portion of the rotating growth vial, and light path 230 corresponds to light path 208 in the tapered portion of the tapered-to-constricted portion of the rotating growth vial. Light paths 210 and 208 are not shown in FIG. 2C but may be seen in, e.g., FIG. 2A. In addition to light paths 234 and 230, there is an emission board 228 to illuminate the light path(s), and detector board 246 to detect the light after the light travels through the cell culture liquid in the rotating growth vial.

The motor 236 used to rotate the rotating growth vial 200 in some embodiments is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 206 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 226, end housings 222 and lower housing 232 of the cell growth device 250 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial is envisioned in some embodiments to be reusable but preferably is consumable, the other components of the cell growth device 250 are preferably reusable and can function as a stand-alone benchtop device or, as here, as a module in a multi-module cell processing system.

The processor (not shown) of the cell growth system may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor of the cell growth system may be programmed to use wavelength values for blanks commensurate with the growth media typically used in mammalian cell culture. Alternatively, a second spectrophotometer and vessel may be included in the cell growth system, where the second spectrophotometer is used to read a blank at designated intervals.

FIG. 2D illustrates a cell growth device as part of an assembly comprising the cell growth device of FIG. 2B coupled to light source 290, detector 292, and thermal components 294. The rotating growth vial 200 is inserted into the cell growth device. Components of the light source 290 and detector 292 (e.g., such as a photodiode with gain control to cover 5-log) are coupled to the main housing of the cell growth device. The lower housing 232 that houses the motor that rotates the rotating growth vial is illustrated, as is one of the flanges 224 that secures the cell growth device to the assembly. Also illustrated is a Peltier device or thermoelectric cooler 294. In this embodiment, thermal control is accomplished by attachment and electrical integration of the cell growth device 200 to the thermal device 294 via the flange 204 on the base of the lower housing 232. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 200 is controlled to approximately +/−0.5° C.

In certain embodiments, a rear-mounted power entry module contains the safety fuses and the on-off switch, which when switched on powers the internal AC and DC power supplies (not shown) activating the processor. Measurements of optical densities (OD) at programmed time intervals are accomplished using a 600 nm Light Emitting Diode (LED) (not shown) that has been columnated through an optic into the lower constricted portion of the rotating growth vial which contains the cells of interest. The light continues through a collection optic to the detection system which consists of a (digital) gain-controlled silicone photodiode. Generally, optical density is normally shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the cell growth device OD measurement records the overall power transmission, so as the cells grow and become denser in population the OD (the loss of signal) increases. The OD system is pre-calibrated against OD standards with these values stored in an on-board memory accessible by the measurement program.

In use, cells are inoculated (cells can be pipetted, e.g., from an automated liquid handling system or by a user) into pre-filled growth media of a rotating growth vial by piercing though the foil seal. The programmed software of the cell growth device sets the control temperature for growth, typically 30° C., then slowly starts the rotation of the rotating growth vial. The cell/growth media mixture slowly moves vertically up the wall due to centrifugal force allowing the rotating growth vial to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 250 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 on minutes. While the cell growth device has been described in the context of measuring the optical density (OD) of a growing cell culture, it should, however, be understood by a skilled artisan given the teachings of the present specification that other cell growth parameters can be measured in addition to or instead of cell culture OD. For example, spectroscopy using visible, UV, or near infrared (NIR) light allows monitoring the concentration of nutrients and/or wastes in the cell culture. Additionally, spectroscopic measurements may be used to quantify multiple chemical species simultaneously. Nonsymmetric chemical species may be quantified by identification of characteristic absorbance features in the NIR. Conversely, symmetric chemical species can be readily quantified using Raman spectroscopy. Many critical metabolites, such as glucose, glutamine, ammonia, and lactate have distinct spectral features in the IR, such that they may be easily quantified. The amount and frequencies of light absorbed by the sample can be correlated to the type and concentration of chemical species present in the sample. Each of these measurement types provides specific advantages. FT-NIR provides the greatest light penetration depth and can be used for thicker sample. FT-mid-IR (MIR) provides information that is more easily discernible as being specific for certain analytes as these wavelengths are closer to the fundamental IR absorptions. FT-Raman is advantageous when interference due to water is to be minimized. Other spectral properties can be measured via, e.g., dielectric impedance spectroscopy, visible fluorescence, fluorescence polarization, or luminescence. Additionally, the cell growth device may include additional sensors for measuring, e.g., dissolved oxygen, carbon dioxide, pH, conductivity, and the like.

The Cell Concentration Module

FIGS. 3A-3K depict variations on one embodiment of a cell concentration/buffer exchange cassette and module that utilizes tangential flow filtration and is configured for use with all cell types, including immortalized cell lines, primary cells and/or stem cells. One embodiment of a cell concentration device described herein operates using tangential flow filtration (TFF), also known as crossflow filtration, in which the majority of the feed flows tangentially over the surface of the filter thereby reducing cake (retentate) formation as compared to dead-end filtration, in which the feed flows into the filter. Secondary flows relative to the main feed are also exploited to generate shear forces that prevent filter cake formation and membrane fouling thus maximizing particle recovery, as described below.

Figure 3A:
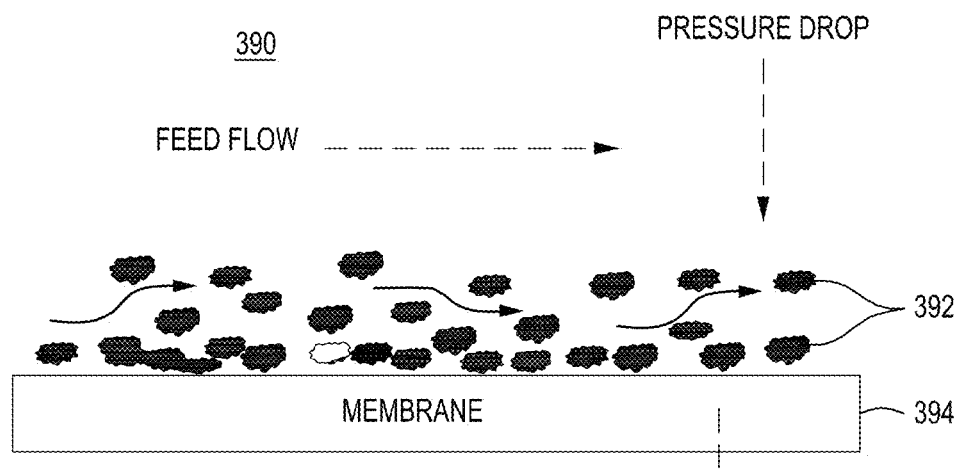
FIG. 3A is a model of tangential flow filtration used in the TFF device presented herein.

The TFF device described herein was designed to take into account two primary design considerations. First, the geometry of the TFF device leads to filtering the cell culture over a large surface area so as to minimize processing time. Second, the design of the TFF device is configured to minimize filter fouling. FIG. 3A is a general model of tangential flow filtration. The TFF device operates using tangential flow filtration, also known as cross-flow filtration. FIG. 3A shows a system 390 with cells flowing over a membrane 394, where the feed flow of the cells 392 in medium or buffer is parallel to the membrane 394. TFF is different from dead-end filtration where both the feed flow and the pressure drop are perpendicular to a membrane or filter.

Figure 3B:
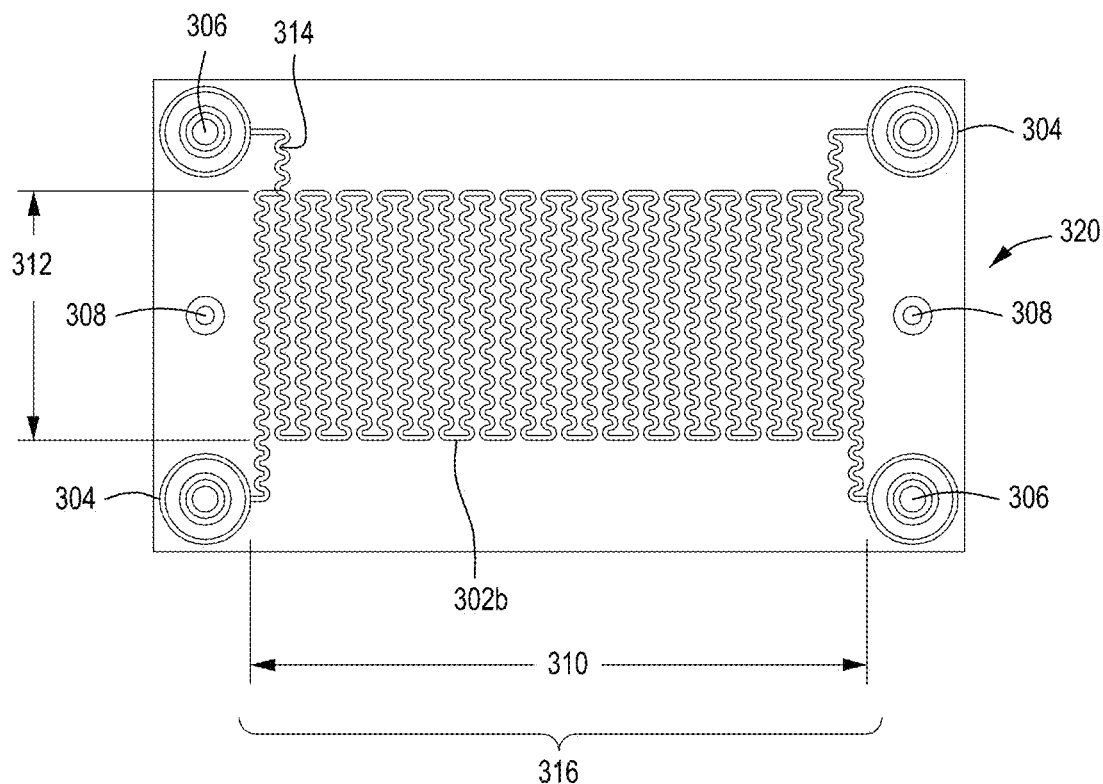
FIG. 3B depicts a top view of a lower member of one embodiment of an exemplary TFF device.

FIG. 3B depicts a top view of the lower member of one embodiment of a TFF device/module providing tangential flow filtration. As can be seen in the embodiment of the TFF device of FIG. 3B, TFF device 300 comprises a channel structure 316 comprising a flow channel 302b through which a cell culture is flowed. The channel structure 316 comprises a single flow channel 302b that is horizontally bifurcated by a membrane (not shown) through which buffer or medium may flow, but cells cannot. This particular embodiment comprises an undulating serpentine geometry 314 (i.e., the small "wiggles" in the flow channel 302) and a serpentine "zig-zag" pattern where the flow channel 302 crisscrosses the device from one end at the left of the device to the other end at the right of the device. The serpentine pattern allows for filtration over a high surface area relative to the device size and total channel volume, while the undulating contribution creates a secondary inertial flow to enable effective membrane regeneration preventing membrane fouling. Although an undulating geometry and serpentine pattern are exemplified here, other channel configurations may be used as long as the channel can be bifurcated by a membrane, and as long as the channel configuration provides for flow through the TFF module in alternating directions. In addition to the flow channel 302b, portals 304 and 306 as part of the channel structure 316 can be seen, as well as recesses 308. Portals 304 collect cells passing through the channel on one side of a membrane (not shown) (the "retentate"), and portals 306 collect the medium ("filtrate" or "permeate") passing through the channel on the opposite side of the membrane (not shown). In this embodiment, recesses 308 accommodate screws or other fasteners (not shown) that allow the components of the TFF device to be secured to one another.

The length 310 and width 312 of the channel structure 316 may vary depending on the volume of the cell culture to be grown and the optical density of the cell culture to be concentrated. The length 310 of the channel structure 316 typically is from 1 mm to 300 mm, or from 50 mm to 250 mm, or from 60 mm to 200 mm, or from 70 mm to 150 mm, or from 80 mm to 100 mm. The width of the channel structure 316 typically is from 1 mm to 120 mm, or from 20 mm to 100 mm, or from 30 mm to 80 mm, or from 40 mm to 70 mm, or from 50 mm to 60 mm. The cross-section configuration of the flow channel 102 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 302 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius.

When looking at the top view of the TFF device/module of FIG. 3B, note that there are two retentate portals 304 and two filtrate portals 306, where there is one of each type portal at both ends (e.g., the narrow edge) of the device 300. In other embodiments, retentate and filtrate portals can on the same surface of the same member (e.g., upper or lower member), or they can be arranged on the side surfaces of the assembly. Unlike other TFF devices that operate continuously, the TFF device/module described herein uses an alternating method for concentrating cells. The overall workflow for cell concentration using the TFF device/module involves flowing a cell culture or cell sample tangentially through the channel structure. The membrane bifurcating the flow channels retains the cells on one side of the membrane and allows unwanted medium or buffer to flow across the membrane into a filtrate side (e.g., lower member 320) of the device. In this process, a fixed volume of cells in medium or buffer is driven through the device until the cell sample is collected into one of the retentate portals 304, and the medium/buffer that has passed through the membrane is collected through one or both of the filtrate portals 306. All types of prokaryotic and eukaryotic cells—both adherent and non-adherent cells—can be grown in the TFF device. Adherent cells may be grown on beads or other cell scaffolds suspended in medium that flow through the TFF device.

In the cell concentration process, passing the cell sample through the TFF device and collecting the cells in one of the retentate portals 304 while collecting the medium in one of the filtrate portals 306 is considered "one pass" of the cell sample. The transfer between retentate reservoirs "flips" the culture. The retentate and filtrate portals collecting the cells and medium, respectively, for a given pass reside on the same end of TFF device/module 300 with fluidic connections arranged so that there are two distinct flow layers for the retentate and filtrate sides, but if the retentate portal 304 resides on the upper member of device/module 300 (that is, the cells are driven through the channel above the membrane and the filtrate (medium) passes to the portion of the channel below the membrane), the filtrate portal 306 will reside on the lower member of device/module 100 and vice versa (that is, if the cell sample is driven through the channel below the membrane, the filtrate (medium) passes to the portion of the channel above the membrane). This configuration can be seen more clearly in FIGS. 3C-3D, where the retentate flows 360 from the retentate portals 304 and the filtrate flows 370 from the filtrate portals 306.

At the conclusion of a "pass" in the growth concentration process, the cell sample is collected by passing through the retentate portal 304 and into the retentate reservoir (not shown). To initiate another "pass", the cell sample is passed again through the TFF device, this time in a flow direction that is reversed from the first pass. The cell sample is collected by passing through the retentate portal 304 and into retentate reservoir (not shown) on the opposite end of the device/module from the retentate portal 304 that was used to collect cells during the first pass. Likewise, the medium/buffer that passes through the membrane on the second pass is collected through the filtrate portal 306 on the opposite end of the device/module from the filtrate portal 306 that was used to collect the filtrate during the first pass, or through both portals. This alternating process of passing the retentate (the concentrated cell sample) through the device/module is repeated until the cells have been concentrated to a desired volume, and both filtrate portals can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell concentration may (and typically do) take place simultaneously.

Figure 3C:
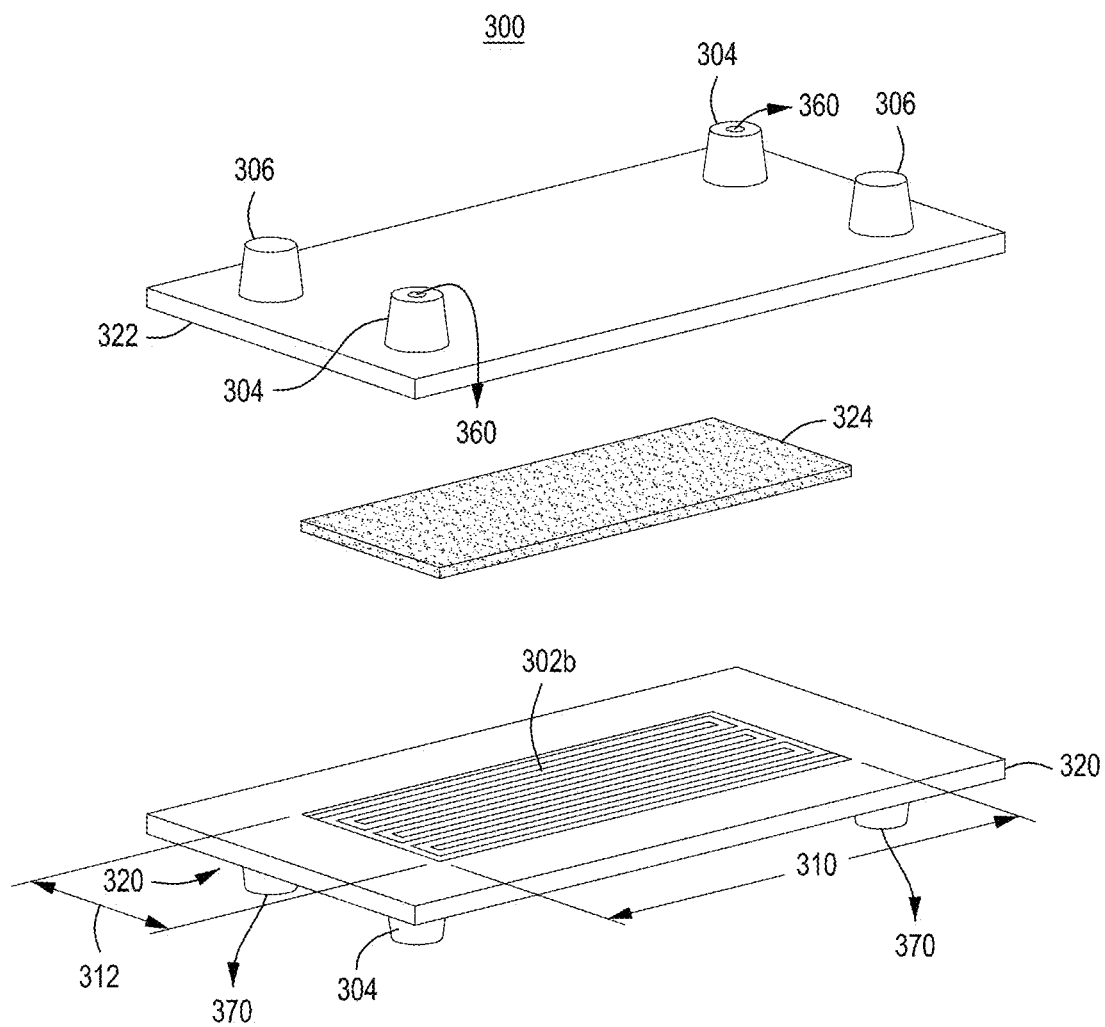
FIG. 3C depicts a top view of upper and lower members and a membrane of an exemplary TFF device.

FIG. 3C depicts a top view of upper (322) and lower (320) members of an exemplary TFF module. Again, portals 304 and 306 are seen. As noted above, recesses—such as the recesses 308 seen in FIG. 3B—provide a means to secure the components (upper member 322, lower member 320, and membrane 324) of the TFF device/membrane to one another during operation via, e.g., screws or other like fasteners. However, in alternative embodiments an adhesive, such as a pressure sensitive adhesive, or ultrasonic welding, or solvent bonding, may be used to couple the upper member 322, lower member 320, and membrane 324 together. Indeed, one of ordinary skill in the art given the guidance of the present disclosure can find yet other configurations for coupling the components of the TFF device, such as e.g., clamps; mated fittings disposed on the upper and lower members; combination of adhesives, welding, solvent bonding, and mated fittings; and other such fasteners and couplings.

Note that there is one retentate portal and one filtrate portal on each "end" (e.g., the narrow edges) of the TFF device/module. The retentate and filtrate portals on the left side of the device/module will collect cells (flow path at 360) and medium (flow path at 370), respectively, for the same pass. Likewise, the retentate and filtrate portals on the right side of the device/module will collect cells (flow path at 360) and medium (flow path at 370), respectively, for the same pass. In this embodiment, the retentate is collected from portals 304 on the top surface of the TFF device, and filtrate is collected from portals 306 on the bottom surface of the device. The cells are maintained in the TFF flow channel above the membrane 324, while the filtrate (medium) flows through membrane 324 and then through portals 306; thus, the top/retentate portals and bottom/filtrate portals configuration is practical. It should be recognized, however, that other configurations of retentate and filtrate portals may be implemented such as positioning both the retentate and filtrate portals on the side (as opposed to the top and bottom surfaces) of the TFF device. In FIG. 3C, the channel structure 302*b* can be seen on the bottom member 320 of the TFF device 300. However, in other embodiments, retentate and filtrate portals can reside on the same of the TFF device.

Also seen in FIG. 3C is membrane or filter 324. Filters or membranes appropriate for use in the TFF device/module are those that are solvent resistant, are contamination free during filtration, and are able to retain the types and sizes of cells of interest. For example, pore sizes can be as low as 0.2 µm, however for other cell types, the pore sizes can be as high as 5 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching. The TFF device shown in FIGS. 3C and 3D do not show a seat in the upper 312 and lower 320 members where the filter 324 can be seated or secured (for example, a seat half the thickness of the filter in each of upper 312 and lower 320 members); however, such a seat is contemplated in some embodiments.

Figure 3D:
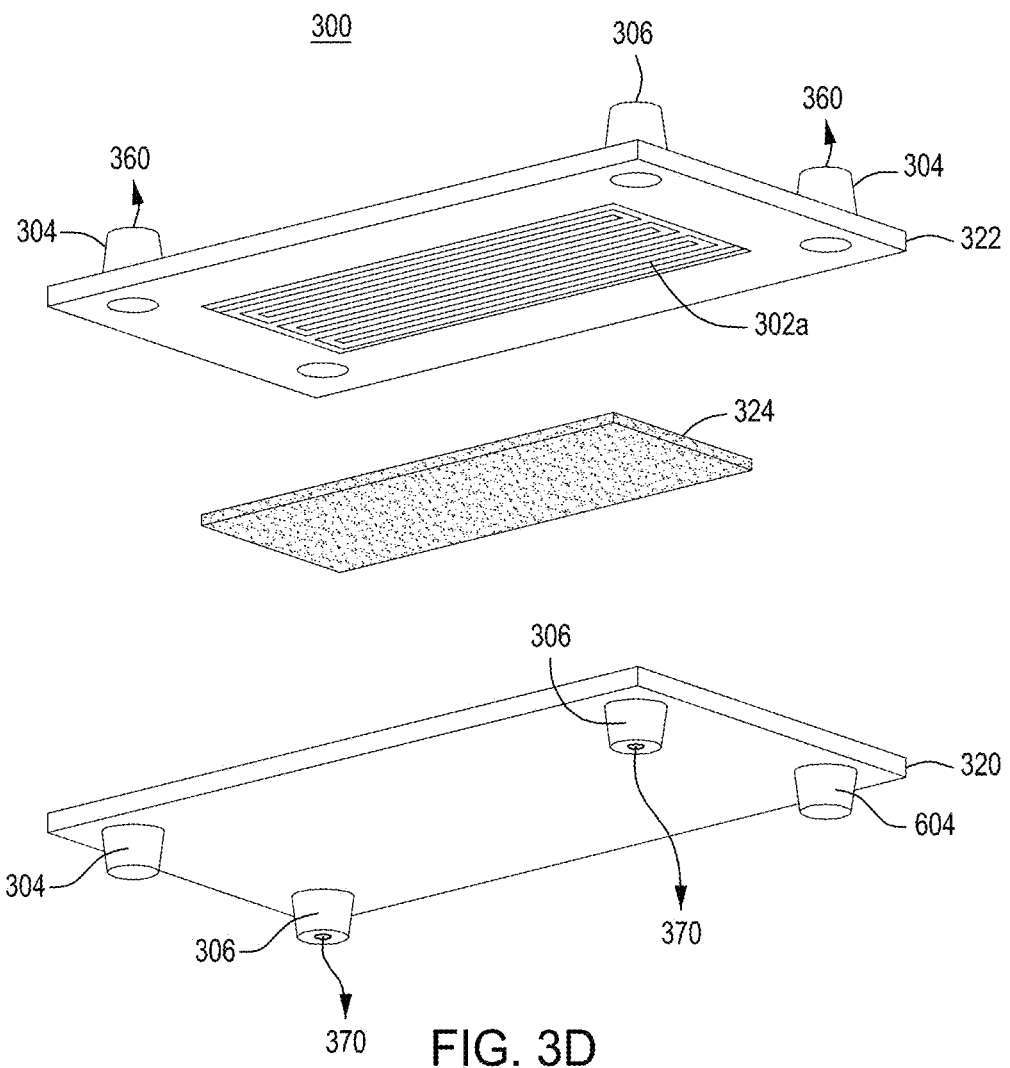
FIG. 3D depicts a bottom view of upper and lower members and a membrane of an exemplary TFF device.

FIG. 3D depicts a bottom view of upper and lower components of the exemplary TFF module shown in FIG. 3C. FIG. 3D depicts a bottom view of upper (322) and lower (320) components of an exemplary TFF module. Again portals 304 and 306 are seen. Note again that there is one retentate portal and one filtrate portal on each end of the device/module. The retentate and filtrate portals on the left side of the device/module will collect cells (flow path at 360) and medium (flow path at 370), respectively, for the same pass. Likewise, the retentate and filtrate portals on the right side of the device/module will collect cells (flow path at 360) and medium (flow path at 370), respectively, for the same pass. In FIG. 3D, the channel structure 302*a* can be seen on the upper member 322 of the TFF device 300. Thus, looking at FIGS. 3C and 3D, note that there is a channel structure 302 (302*a* and 302*b*) in both the upper and lower members, with a membrane 324 between the upper and lower portions of the channel structure. The channel structure 302 of the upper 322 and lower 320 members (302*a* and 302*b*, respectively) mate to create the flow channel with the membrane 324 positioned horizontally between the upper and lower members of the flow channel thereby bifurcating the flow channel.

Medium exchange (during cell growth) or buffer exchange (during cell concentration or rendering the cells competent) is performed on the TFF device/module by adding fresh medium to growing cells or a desired buffer to the cells concentrated to a desired volume; for example, after the cells have been concentrated at least 20-fold, 30-fold, 40-fold, 50-fold, 60-fold, 70-fold, 80-fold, 90-fold, 100-fold, 150-fold, 200-fold or more. A desired exchange medium or exchange buffer is added to the cells either by addition to the retentate reservoir or thorough the membrane from the filtrate side and the process of passing the cells through the TFF device 300 is repeated until the cells have been grown to a desired optical density or concentrated to a desired volume in the exchange medium or buffer. This process can be repeated any number of desired times so as to achieve a desired level of exchange of the buffer and a desired volume of cells. The exchange buffer may comprise, e.g., glycerol or sorbitol thereby rendering the cells competent for transformation in addition to decreasing the overall volume of the cell sample.

The TFF device 300 may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 3E:
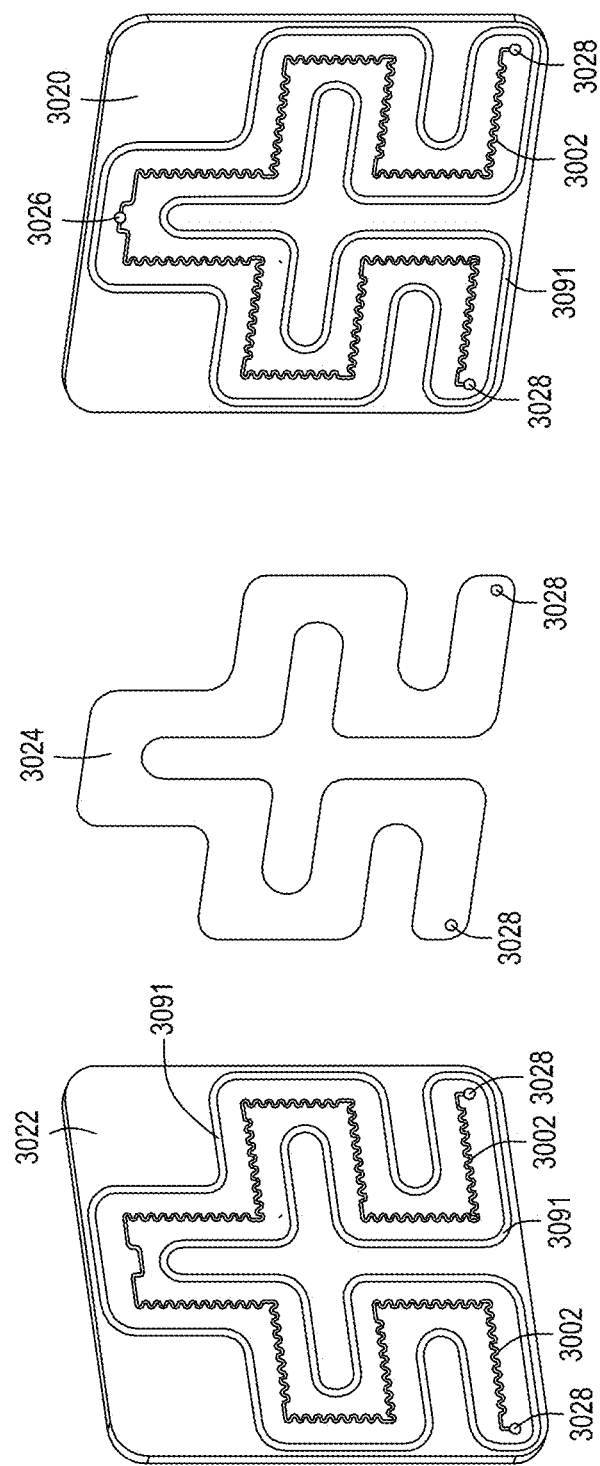
FIGS. 3E-3K depict various views of yet another embodiment of a TFF module having fluidically coupled reservoirs.
Figure 3F:
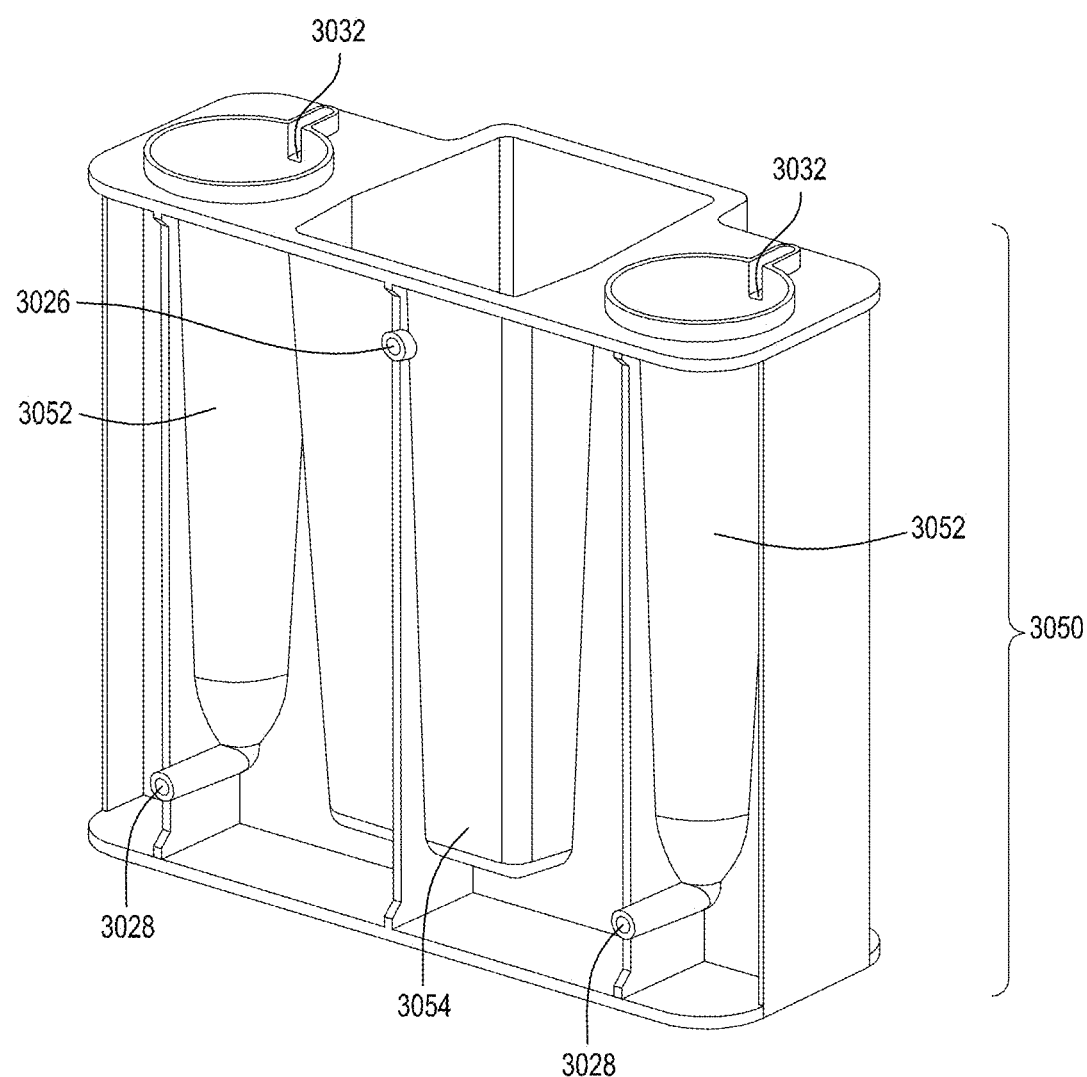
Figure 3G:
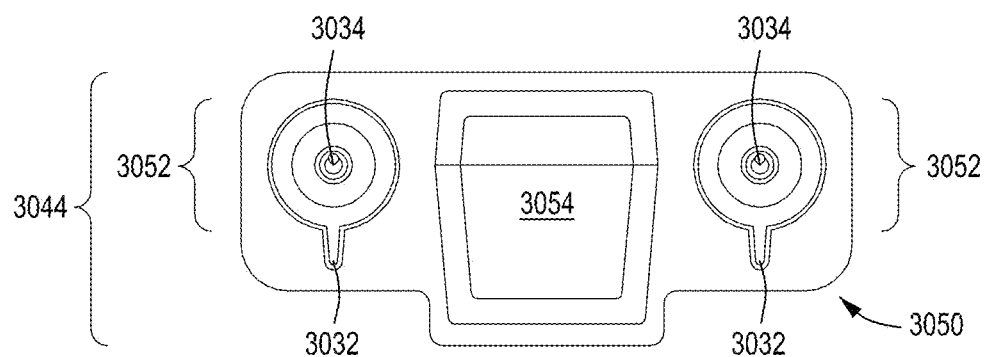
Figure 3H:
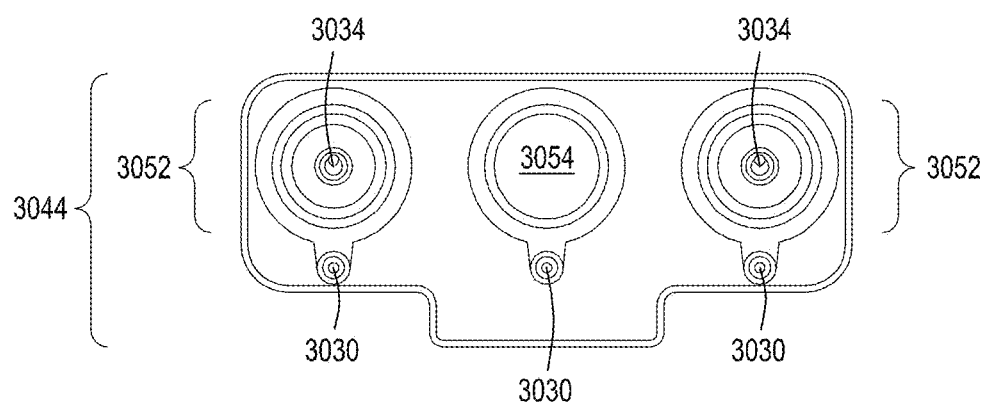
Figure 3I:
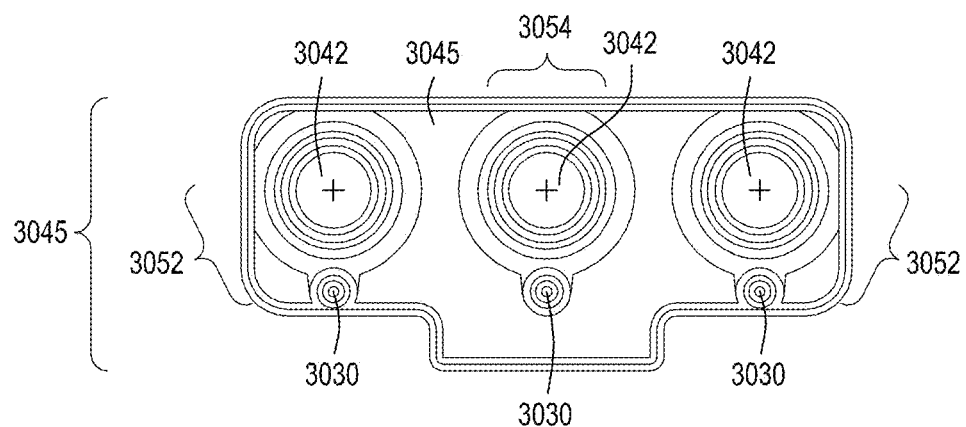
Figure 3J:
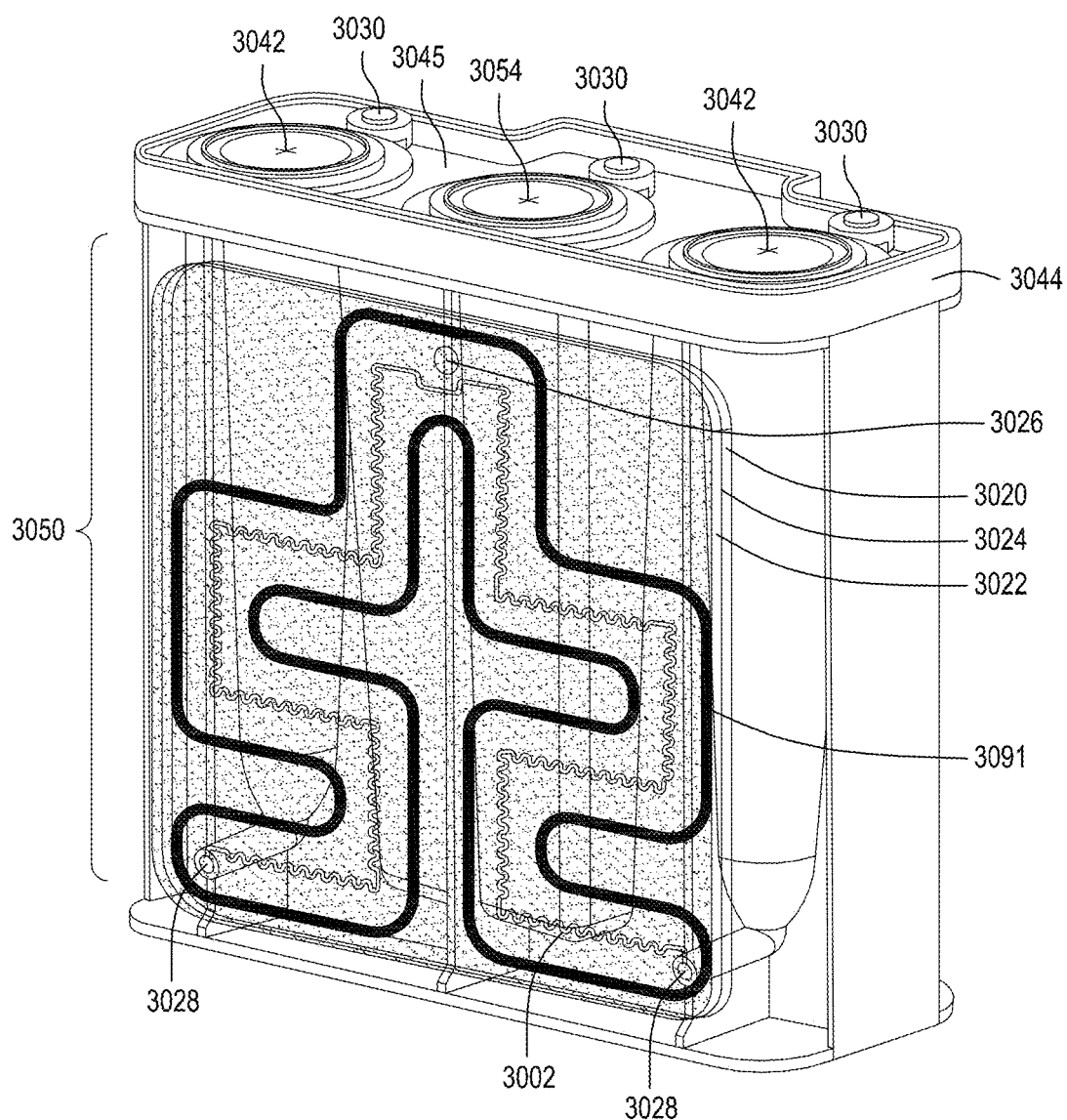
Figure 3K:
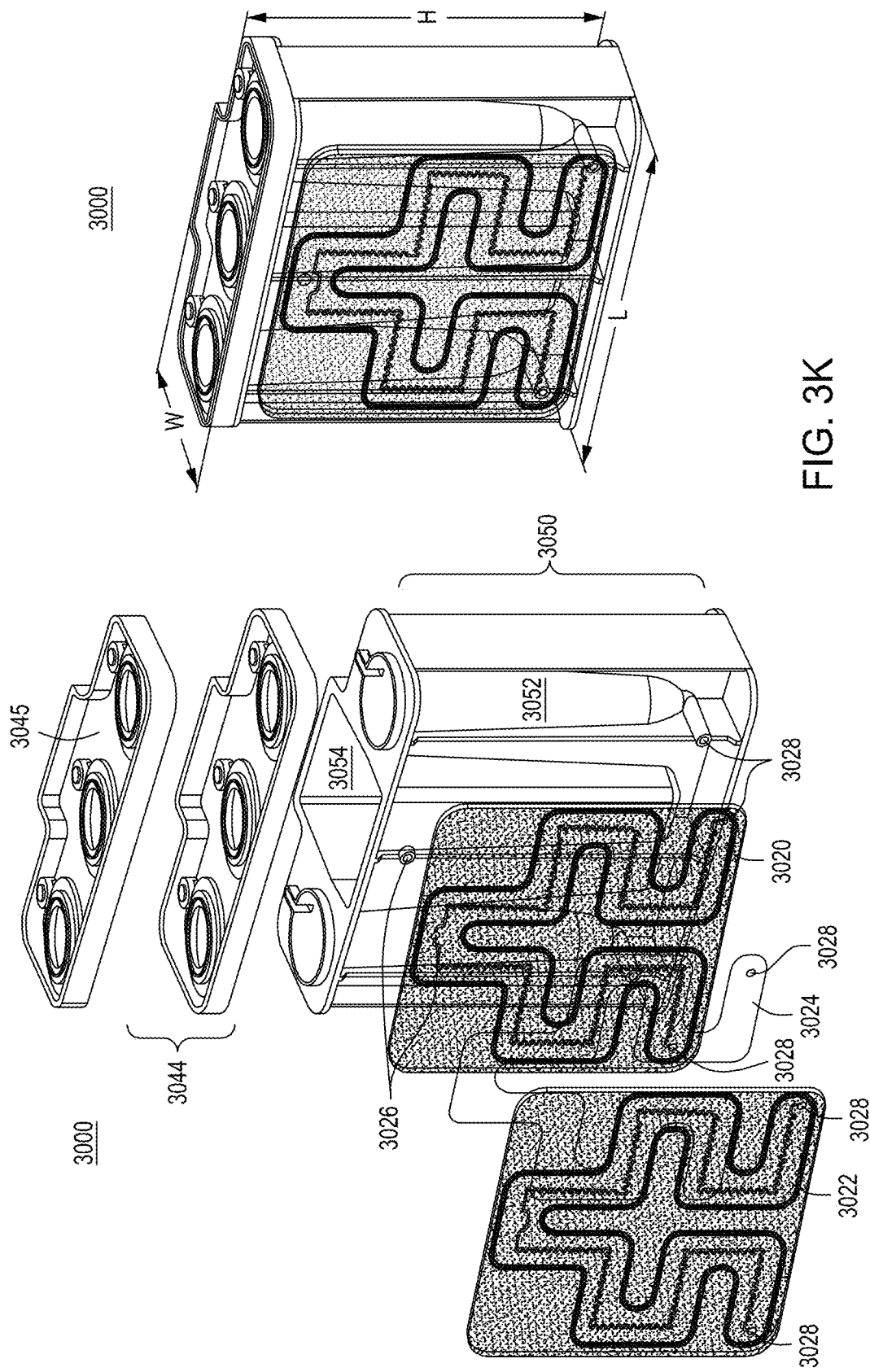

FIGS. 3E-3K depict an alternative embodiment of a tangential flow filtration (TFF) device/module. FIG. 3E depicts a configuration of an upper (retentate) member 3022 (on left), a membrane or filter 3024 (middle), and a lower (permeate/filtrate) member 3020 (on the right). In the configuration shown in FIGS. 3E-3, the retentate member 3022 is no longer "upper" and the permeate/filtrate member 3020 is no longer "lower", as the retentate member 3022 and permeate/filtrate member 3020 are coupled side-to-side as seen in FIGS. 3J and 3K. In FIG. 3E, retentate member 3022 comprises a tangential flow channel 3002, which has a serpentine configuration that initiates at one lower corner of retentate member 3022—specifically at retentate port 3028—traverses across and up then down and across retentate member 3022, ending in the other lower corner of retentate member 3022 at a second retentate port 3028. Also seen on retentate member 3022 is energy director 3091, which circumscribes the region where membrane or filter 3024 is seated. Energy director 3091 in this embodiment mates with and serves to facilitate ultrasonic wending or bonding of retentate member 3022 with permeate/filtrate member 3020 via the energy director component on permeate/filtrate member 3020. Also seen is membrane or filter 3024 has through-holes for retentate ports 3028, which is configured to seat within the circumference of energy directors 3091 between the retentate member 3022 and the permeate/filtrate member 3020. Permeate/filtrate member 3020 comprises, in addition to energy director 3091, through-holes for retentate port 3028 at each bottom corner (which mate with the through-holes for retentate ports 3028 at the bottom corners of membrane 3024 and retentate ports 3028 in retentate member 3022), as well as a tangential flow channel 3002 and a single permeate/filtrate port 3026 positioned at the top and center of permeate/filtrate member 3020. The tangential flow channel 3002 structure in this embodiment has a serpentine configuration and an undulating geometry, although other geometries may be used. In some aspects, the length of the tangential flow channel is from 10 mm to 1000 mm, from 60 mm to 200 mm, or from 80 mm to 100 mm. In some aspects, the width of the channel structure is from 10 mm to 120 mm, from 40 mm to 70 mm, or from 50 mm to 60 mm. In some aspects, the cross section of the tangential flow channel 1202 is rectangular. In some aspects, the cross section of the tangential flow channel 1202 is 5 µm to 1000 µm wide and 5 µm to 1000 µm high, 300 µm to 700 µm wide and 300 µm to 700 µm high, or 400 µm to 600 µm wide and 400 µm to 600 µm high. In other aspects, the cross section of the tangential flow channel 1202 is circular, elliptical, trapezoidal, or oblong, and is 100 µm to 1000 µm in hydraulic radius, 300 µm to 700 µm in hydraulic radius, or 400 µm to 600 µm in hydraulic radius.

FIG. 3F is a side perspective view of a reservoir assembly 3050. The embodiment of FIG. 3F, the retentate member is separate from the reservoir assembly. Reservoir assembly 3050 comprises retentate reservoirs 3052 on either side of a single permeate reservoir 3054. Retentate reservoirs 3052 are used to contain the cells and medium as the cells are transferred through the cell concentration/growth device or module and into the retentate reservoirs during cell concentration and/or growth. Permeate/filtrate reservoir 3054 is used to collect the filtrate fluids removed from the cell culture during cell concentration, or old buffer or medium during cell growth. In the embodiment depicted in FIGS. 3E-3L, buffer or medium is supplied to the permeate/filtrate member from a reagent reservoir separate from the device module. Additionally seen in FIG. 3F are grooves 3032 to accommodate pneumatic ports (not seen), permeate/filtrate port 3026, and retentate port through-holes 3028. The retentate reservoirs are fluidically coupled to the retentate ports 3028, which in turn are fluidically coupled to the portion of the tangential flow channel disposed in the retentate member (not shown). The permeate/filtrate reservoir is fluidically coupled to the permeate/filtrate port 3026 which in turn are fluidically coupled to the portion of the tangential flow channel disposed in permeate/filtrate member (not shown), where the portions of the tangential flow channels are bifurcated by membrane (not shown). In embodiments including the present embodiment, up to 120 mL of cell culture can be grown and/or filtered, or up to 100 mL, 90 mL, 80 mL, 70 mL, 60 mL, 50 mL, 40 mL, 30 mL or 20 mL of cell culture can be grown and/or concentrated.

FIG. 3G depicts a top-down view of the reservoir assembly 3050 shown in FIG. 3F, FIG. 3H depicts a cover 3044 for reservoir assembly 3050 shown in FIGS. 3F, and 3I depicts a gasket 3045 that in operation is disposed on cover 3044 of reservoir assembly 3050 shown in FIG. 3F. FIG. 3G is a top-down view of reservoir assembly 3050, showing two retentate reservoirs 3052, one on either side of permeate reservoir 3054. Also seen are grooves 3032 that will mate with a pneumatic port (not shown), and fluid channels 3034 that reside at the bottom of retentate reservoirs 3052, which fluidically couple the retentate reservoirs 3052 with the retentate ports 3028 (not shown), via the through-holes for the retentate ports in permeate/filtrate member 3024 and membrane 3024 (also not shown). FIG. 3H depicts a cover 3044 that is configured to be disposed upon the top of reservoir assembly 3050. Cover 3044 has round cut-outs at the top of retentate reservoirs 3052 and permeate/filtrate reservoir 3054. Again, at the bottom of retentate reservoirs 3052 fluid channels 3034 can be seen, where fluid channels 3034 fluidically couple retentate reservoirs 3052 with the retentate ports 3028 (not shown). Also shown are three pneumatic ports 3030 for each retentate reservoir 3052 and permeate/filtrate reservoir 3054. FIG. 3I depicts a gasket 3045 that is configured to be disposed upon the cover 3044 of reservoir assembly 3050. Seen are three fluid transfer ports 3042 for each retentate reservoir 3052 and for permeate/filtrate reservoir 3054. Again, three pneumatic ports 3030, for each retentate reservoir 3052 and for permeate/filtrate reservoir 3054, are shown.

FIG. 3J depicts an embodiment of assembled TFF module 3000. Note that in this embodiment of a TFF module the retentate member 3022 is no longer "upper", and the permeate/filtrate member 3020 is no longer "lower", as the retentate member 3022 and permeate/filtrate member 3020 are coupled side-to-side with membrane 3024 sandwiched between retentate member 3022 and permeate/filtrate member 3020. Also, retentate member 3022, membrane member 3024, and permeate/filtrate member 3020 are coupled side-to-side with reservoir assembly 3050. Seen are two retentate ports 3028 (which couple the tangential flow channel 3002 in retentate member 3022 to the two retentate reservoirs (not shown), and one permeate/filtrate port 3026, which couples the tangential flow channel 3002 in permeate/filtrate member 3020 to the permeate/filtrate reservoir (not shown). Also seen is tangential flow channel 3002, which is formed by the mating of retentate member 3022 and permeate/filtrate member 3020, with membrane 3024 sandwiched between and bifurcating tangential flow channel 3002. Also seen is energy director 3091, which in this FIG. 3J has been used to ultrasonically weld or couple retentate member 3022 and permeate/filtrate member 3020, surrounding membrane 3024. Cover 3044 can be seen on top of reservoir assembly 3050, and gasket 3045 is disposed upon cover 3044. Gasket 3045 engages with and provides a fluid-tight seal and pneumatic connections with fluid transfer ports 3042 and pneumatic ports 3030, respectively.

FIG. 3K depicts, on the left, an exploded view of the TFF module 3000 shown in FIG. 3J. Seen are components reservoir assembly 3050, a cover 3044 to be disposed on reservoir assembly 3050, a gasket 3045 to be disposed on cover 3044, retentate member 3022, membrane or filter 3024, and permeate/filtrate member 3020. Also seen is permeate/filtrate port 3026, which mates with permeate/filtrate port 3026 on permeate/filtrate reservoir 3054, as well as two retentate ports 3028, which mate with retentate ports 3028 on retentate reservoirs 3052 (where only one retentate reservoir 3052 can be seen clearly in this FIG. 3K). Also seen are through-holes for retentate ports 3028 in membrane 3024 and permeate/filtrate member 3020. FIG. 3K depicts on the left the assembled TFF module 3000 showing length, height, and width dimensions. The assembled TFF device 3000 typically is from 50 to 175 mm in height, or from 75 to 150 mm in height, or from 90 to 120 mm in height; from 50 to 175 mm in length, or from 75 to 150 mm in length, or from 90 to 120 mm in length; and is from 30 to 90 mm in depth, or from 40 to 75 mm in depth, or from about 50 to 60 mm in depth. An exemplary TFF device is 110 mm in height, 120 mm in length, and 55 mm in depth.

Like in other embodiments described herein, the TFF device or module depicted in FIGS. 3E-3K can constantly measure cell culture growth, and in some aspects, cell culture growth is measured via optical density (OD) of the cell culture in one or both of the retentate reservoirs and/or in the flow channel of the TFF device. Optical density may be measured continuously (kinetic monitoring) or at specific time intervals; e.g., every 5, 10, 15, 20, 30 45, or 60 seconds, or every 1, 2, 3, 4, 5, 6, 7, 8, 9, or 10 or so on minutes. Further, the TFF module can adjust growth parameters (temperature, aeration) to have the cells at a desired optical density at a desired time.

Figure 3L:
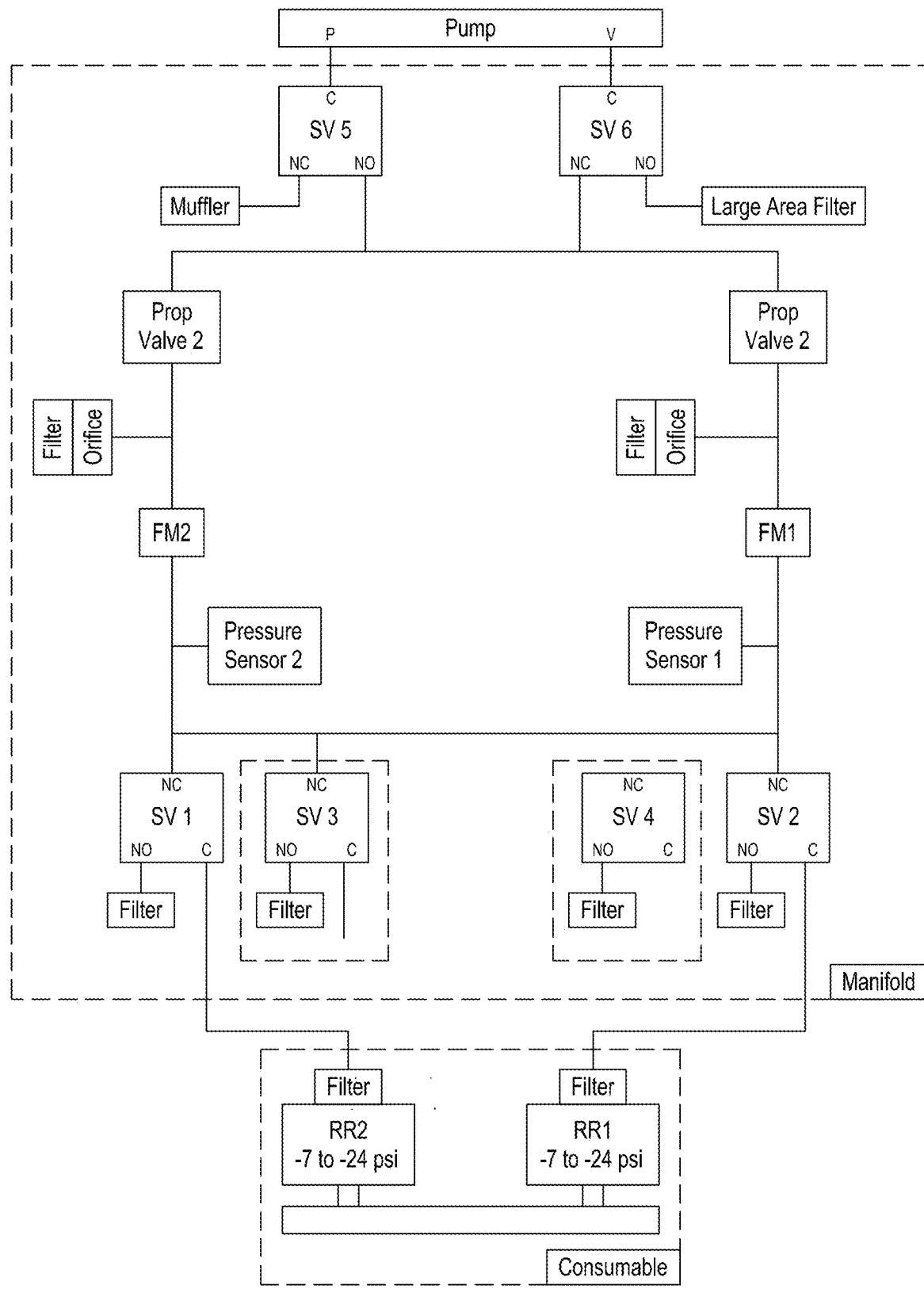
FIG. 3L is an exemplary pneumatic architecture diagram for the TFF module described in relation to FIGS. 3E-3K.

FIG. 3L is an exemplary pneumatic block diagram suitable for the TFF module depicted in FIGS. 3E-3K. The pump is connected to two solenoid valves (SV5 and SV6) delivering positive pressure (P) or negative pressure (V). The two solenoid valves SV5 and SV6 couple the pump to the manifold, and two solenoid valves, SV1 and SV2, are connected to the reservoirs (RR1 and RR2). There are also two solenoid valves in reserve (SV3 and SV4). There is a proportional valve (PV2 and PV2), a flow meter (FM1 and FM2), and a pressure sensor (Pressure Sensors 1 and 2) positioned in between each of solenoid valves SV1 and SV2 connecting the pump to the system and the solenoid valves SV1 And SV2 to the reservoirs. The pressure sensors and prop valves work in concert in a feedback loop to maintain the required pressure.

As an alternative to the TFF module described above, a cell concentration module comprising a hollow filter may be employed. Examples of filters suitable for use in the present invention include membrane filters, ceramic filters and metal filters. The filter may be used in any shape; the filter may for example be cylindrical or essentially flat. Preferably, the filter used is a membrane filter, preferably a hollow fiber filter. The term "hollow fiber" is meant a tubular membrane. The internal diameter of the tube is at least 0.1 mm, more preferably at least 0.5 mm, most preferably at least 0.75 mm and preferably the internal diameter of the tube is at most 10 mm, more preferably at most 6 mm, most preferably at most 1 mm. Filter modules comprising hollow fibers are commercially available from various companies, including G.E. Life Sciences (Marlborough, Mass.) and InnovaPrep (Drexel, Mo.). Specific examples of hollow fiber filter systems that can be used, modified or adapted for use in the present methods and systems include, but are not limited to, U.S. Pat. Nos. 9,738,918; 9,593,359; 9,574,977; 9,534,989; 9,446,354; 9,295,824; 8,956,880; 8,758,623; 8,726,744; 8,677,839; 8,677,840; 8,584,536; 8,584,535; and 8,110,112.

The Editing Machinery Introduction Module

In addition to the modules for cell growth, and cell concentration FIGS. 4A-4E depict variations on one embodiment of a module for introduction of editing machinery into cells. The introduction methods can be tailored depending on the cell type and nature of the machinery to be introduced (e.g., nucleic acids or proteins).

In some aspects, the module is configured to transform mammalian cells. In some aspects, an editing cassette plasmid and nuclease can be delivered to the target cell by traditional mammalian cell transfection techniques. Examples include lipid-mediated transfection, Calcium Phosphate-mediated transfection, electroporation, cationic peptides, cationic polymers, or nucleofection. Proteins such as an RNA-directed nuclease can also be delivered to the cells using various mechanisms. For example, an RNA-directed nuclease can be introduced to mammalian cells using shuttle vectors such as those described in U.S. Pat. Nos. 9,982,267 and 9,738,687, which are incorporated herein by reference for all purposes.

In certain embodiments, some or all of the machinery necessary for editing are introduced using transformation. FIG. 4A is a perspective view of six co-joined flow-through electroporation devices 450. FIG. 4A depicts six flow-through electroporation units 450 arranged on a single substrate 456. Each of the six flow-through electroporation units 450 have wells 452 that define cell sample inlets and wells 454 that define cell sample outlets. Once the six flow-through electroporation units 450 are fabricated, they can be separated from one another (e.g., "snapped apart") and used one at a time, or alternatively in embodiments two or more flow-through electroporation units 450 can be used in parallel without separation.

The flow-through electroporation devices achieve high efficiency cell electroporation with low toxicity. The flow-through electroporation devices of the disclosure allow for particularly easy integration with robotic liquid handling instrumentation that is typically used in automated systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

Generally speaking, microfluidic electroporation—using cell suspension volumes of less than approximately 10 ml and as low as 1 µl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit electroporation device configurations; and integrated, automatic, multi-module cell processing and analysis.

In specific embodiments of the flow-through electroporation devices of the disclosure the toxicity level of the transformation results in greater than 10% viable cells after electroporation, preferably greater than 15%, 20%, 25%, 30%, 35%, 40%, 45%, 50%, 55%, 60%, 70%, 75%, 80%, 85%, 90%, or even 95% viable cells following transformation, depending on the cell type and the nucleic acids being introduced into the cells.

The flow-through electroporation device described in relation to FIGS. 4A-4D comprises a housing with an electroporation chamber, a first electrode and a second electrode configured to engage with an electric pulse generator, by which electrical contacts engage with the electrodes of the electroporation device. In certain embodiments, the electroporation devices are autoclavable and/or disposable, and may be packaged with reagents in a reagent cartridge. The electroporation device may be configured to electroporate cell sample volumes between 1 µl to 2 ml, 10 µl to 1 ml, 25 µl to 750 µl, or 50 µl to 500 µl.

Figure 4B:
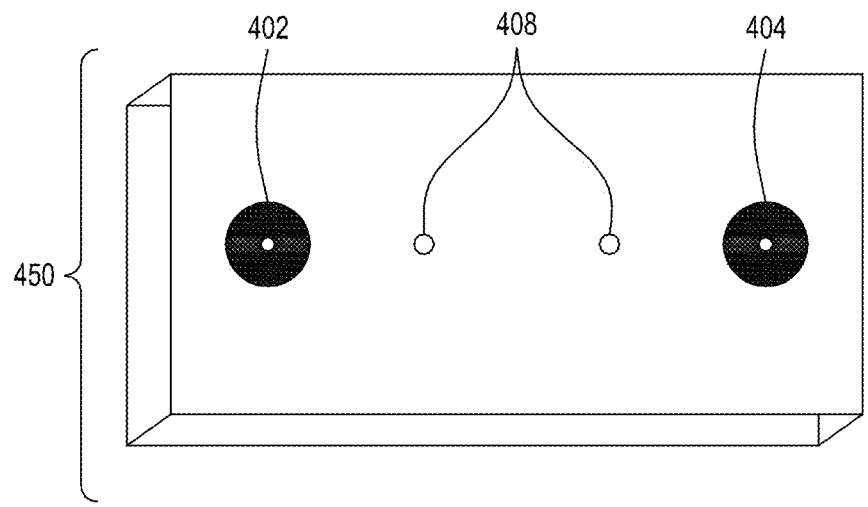
FIG. 4B is a top view of one embodiment of an exemplary flow-through electroporation device.
Figure 4C:
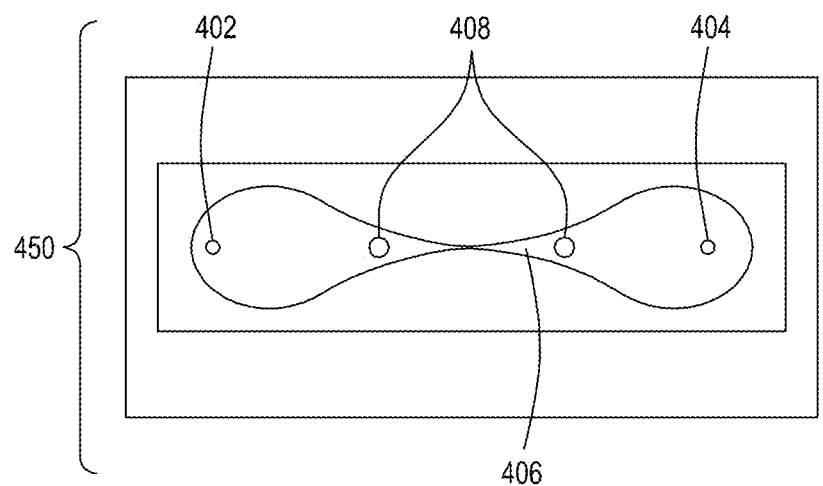
FIG. 4C depicts a top view of a cross section of the electroporation device of FIG. 4C.
Figure 4D:
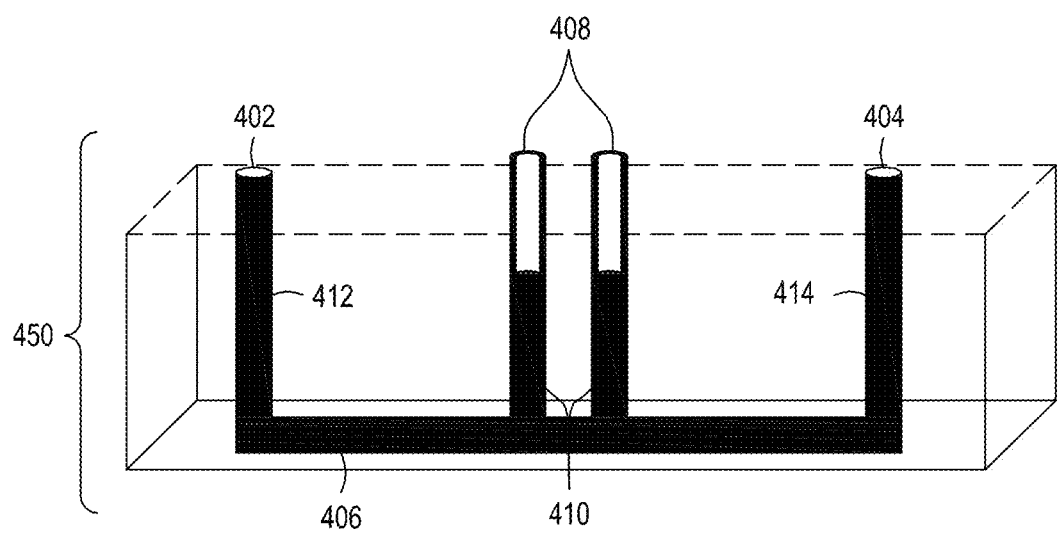
FIG. 4D is a side view cross section of a lower portion of the electroporation devices of FIGS. 4C and 4D.
Figures 5A, 5B:
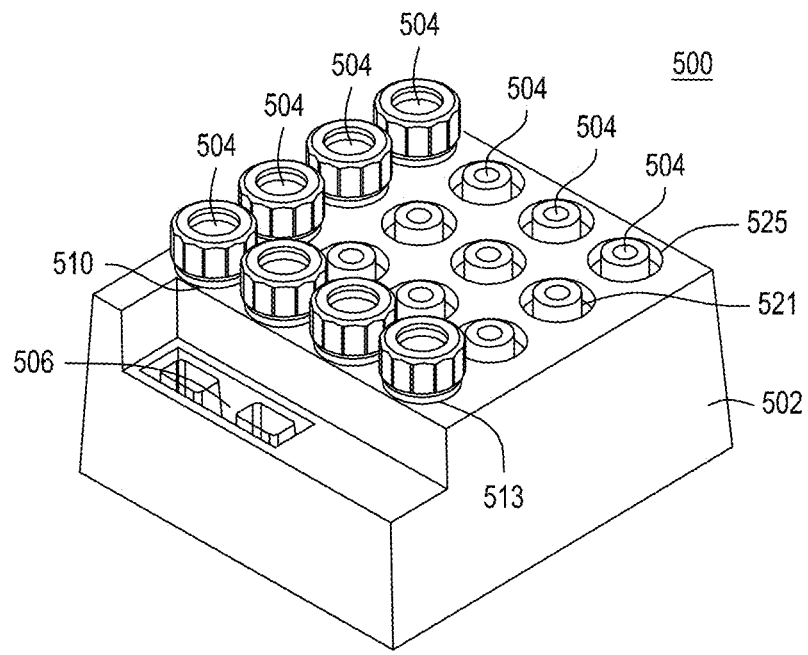
FIGS. 5A and 5B depict the structure and components of one embodiment of a reagent cartridge.

In one exemplary embodiment, FIG. 4B depicts a top view of a flow-through electroporation device 450 having an inlet 402 for introduction of cells and an exogenous reagent to be electroporated into the cells ("cell sample") and an outlet 404 for the cell sample following electroporation. Electrodes 408 are introduced through electrode channels (not shown) in the device. FIG. 4C shows a cutaway view from the top of flow-through electroporation device 450, with the inlet 402, outlet 404, and electrodes 408 positioned with respect to a constriction in flow channel 406. A side cutaway view of the bottom portion of flow-through electroporation device 450 in FIG. 4D illustrates that electrodes 408 in this embodiment are positioned in electrode channels 410 and perpendicular to flow channel 406 such that the cell sample flows from the inlet channel 412 through the flow channel 406 to the outlet channel 414, and in the process the cell sample flows into the electrode channels 410 to be in contact with electrodes 408. In this aspect, the inlet channel, outlet channel and electrode channels all originate from the top planar side of the device; however, the flow-through electroporation architecture depicted in FIGS. 4B-4D is but one architecture useful with the reagent cartridges described herein. Additional electrode architectures are described, e.g., in U.S. Ser. No. 16/147,120, filed 24 Sep. 2018; Ser. No. 16/147,865, filed 30 Sep. 2018; and Ser. No. 16/147,871, filed 30 Sep. 2018.

The Reagent Cartridge

FIG. 5A depicts an exemplary combination reagent cartridge and electroporation device 500 ("cartridge") that may be used in an automated multi-module cell processing instrument. Cartridge 500 comprises a body 502, and reagent receptacles or reservoirs 504. Additionally, cartridge 500 comprises a device for introduction of nucleic acids and/or proteins into the cells, e.g. an electroporation device 506 (an exemplary embodiment of which is described in detail in relation to FIGS. 4A-4D. Cartridge 500 may be disposable, or may be configured to be reused. Preferably, cartridge 500 is disposable. Cartridge 500 may be made from any suitable material, including stainless steel, aluminum, or plastics including polyvinyl chloride, cyclic olefin copolymer (COC), polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the cartridge is disposable, preferably it is made of plastic. Preferably the material used to fabricate the cartridge is thermally-conductive, as in certain embodiments the cartridge 500 contacts a thermal device (not shown) that heats or cools reagents in the reagent receptacles or reservoirs 504. In some embodiments, the thermal device is a Peltier device or thermoelectric cooler. Reagent receptacles or reservoirs 504 may be receptacles into which individual tubes of reagents are inserted as shown in FIG. 5A, receptacles into which one or more multiple co-joined tubes are inserted, or the reagent receptacles may hold the reagents without inserted tubes with the reagents dispensed directly into the receptacles or reservoirs. Additionally, the receptacles in a reagent cartridge may be configured for any combination of tubes, co-joined tubes, and direct-fill of reagents.

In one embodiment, the reagent receptacles or reservoirs 504 of reagent cartridge 500 are configured to hold various size tubes, including, e.g., 250 ml tubes, 25 ml tubes, 10 ml tubes, 5 ml tubes, and Eppendorf or microcentrifuge tubes. In yet another embodiment, all receptacles may be configured to hold the same size tube, e.g., 5 ml tubes, and reservoir inserts may be used to accommodate smaller tubes in the reagent reservoir. In yet another embodiment—particularly in an embodiment where the reagent cartridge is disposable—the reagent reservoirs hold reagents without inserted tubes. In this disposable embodiment, the reagent cartridge may be part of a kit, where the reagent cartridge is pre-filled with reagents and the receptacles or reservoirs sealed with, e.g., foil, heat seal acrylic or the like and presented to a consumer where the reagent cartridge can then be used in an automated multi-module cell processing instrument. The reagents contained in the reagent cartridge will vary depending on work flow; that is, the reagents will vary depending on the processes to which the cells are subjected in the automated multi-module cell processing instrument.

FIG. 5B depicts an exemplary matrix configuration 140 for the reagents contained in the reagent cartridges of FIG. 5A; where this matrix embodiment is a 4×4 reagent matrix. Through a matrix configuration, a user (or programmed processor) can locate the proper reagent for a given process. That is, reagents such as cell samples, enzymes, buffers, nucleic acid vectors, expression cassettes, reaction components (such as, e.g., $MgCl_2$, dNTPs, isothermal nucleic acid assembly reagents, Gap Repair reagents, and the like), wash solutions, ethanol, and magnetic beads for nucleic acid purification and isolation, etc. are positioned in the matrix 540 at a known position. For example, reagents are located at positions A1 (510), A2 (511), A3 (512), A4 (513), B1 (514), B2 (515) and so on through, in this embodiment, position D4 (525). FIG. 5A is labeled to show where several reservoirs 504 correspond to matrix 540: See receptacles 510, 513, 521 and 525. Although the reagent cartridge 500 of FIG. 5A and the matrix configuration 540 of FIG. 5B shows a 4×4 matrix, matrices of the reagent cartridge and electroporation devices can be any configuration, such as, e.g., 2×2, 2×3, 2×4, 2×5, 2×6, 3×3, 3×5, 4×6, 6×7, or any other configuration, including asymmetric configurations, or two or more different matrices depending on the reagents needed for the intended workflow. Note in FIG. 4A the matrix configuration is a 5×3+1 matrix.

In preferred embodiments of reagent cartridge 500 shown in FIG. 5A, the reagent cartridge comprises a script (not shown) readable by a processor (not shown) for dispensing the reagents via a liquid handling device (not shown) and controlling the electroporation device contained within reagent cartridge 500. Also, the reagent cartridge 500 as one component in an automated multi-module cell processing instrument may comprise a script specifying two, three, four, five, ten or more processes performed by the automated multi-module cell processing instrument, or even specify all processes performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components of the automated multi-module cell processing instrument may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing instrument such as described in relation to FIGS. 1A-1D. For example, the reagent cartridge may comprise a script to pipette electrocompetent cells from reservoir A2 (511), transfer the cells to the electroporation device 506, pipette a nucleic acid solution comprising an editing vector from reservoir C3 (520), transfer the nucleic acid solution to the electroporation device, initiate the electroporation process for a specified time, then move the porated cells to a reservoir D4 (525) in the reagent cassette or to another module such as the rotating growth vial (118 or 120 of FIG. 1A) in the automated multi-module cell processing instrument in FIG. 1A. In another example, the reagent cartridge may comprise a script to pipette transfer of a nucleic acid solution comprising a vector from reservoir C3 (520), nucleic acid solution comprising editing oligonucleotide cassettes in reservoir C4 (521), and isothermal nucleic acid assembly reaction mix from A1 (510) to the isothermal nucleic acid assembly/desalting reservoir (414 of FIG. 4A). The script may also specify process steps performed by other modules in the automated multi-module cell processing instrument. For example, the script may specify that the isothermal nucleic acid assembly/desalting module be heated to 50° C. for 30 min to generate an assembled isothermal nucleic acid product; and desalting of the assembled isothermal nucleic acid product via magnetic bead-based nucleic acid purification involving a series of pipette transfers and mixing of magnetic beads in reservoir B2 (515), ethanol wash in reservoir B3 (516), and water in reservoir C1 (518) to the isothermal nucleic acid assembly/desalting reservoir (114 of FIG. 1A).

The Enrichment Module

The disclosure also includes automated multi-module cell editing instruments with an enrichment module that performs enrichment methods including those described herein to increase the overall editing efficiency in a population of cells, e.g., mammalian cells.

As will be apparent to one skilled in the art upon reading the disclosure, the enrichment module can be designed to accommodate the particular enrichment method, and is preferably (but not required to be) connected to the remaining modules of the multi-module instrument, e.g. via an automated liquid handling system or other cell transfer device.

In certain embodiments, the enrichment module can be a module used off-instrument, with the resulting enriched cell populations introduced back to the integrated instrument, or alternatively to a companion instrument that completes the editing and recovery cycle. In such cases, the enrichment module acts independent from the automated multi-module instrument, but is included into the overall workflow. Thus, the work flow may require coordination of two or more processors responsible for different parts of the work flow.

In some embodiments, the enrichment module is in fluid communication with the automated multi-module instruments and integrated with a liquid handling system and controlled by a single processor.

In some modules, the enrichment is a positive enrichment module that enriches for cells that contain an introduced selection marker. In some aspects, the enrichment is a negative selection that depletes cells based on the lack of a selection marker or a characteristic that is absent due to the specific enrichment method used, e.g., antibiotic selection.

In some aspects of the disclosure, the selection process can be performed computationally, and the expression of the selection marker monitored and used in future data analysis to determine the editing rate of a cell population.

Certain selection methods that can be used with the methods of the present disclosure provides fluorescent or bioluminescent selection as a read out for properly-edited cells. The properly-edited cells can be sorted from non-edited or improperly-edited cells via methods such as fluorescence-activated cell sorting (FACS) and magnetic-activated cell sorting (MACS), and modules for performing such selections can be incorporated into the automated multi-module cell processing instrument (see, e.g., 140 of FIG. 1A). Using FACS or MACS, a heterogenous mixture of live cells can be sorted into different populations based upon expression markers that have been expressed due to the presence of editing machinery for introduction of the selection methods and intended edits of the target region.

FACS can isolate cells based on internal staining or intracellular protein expression, and allows for the purification of individual cells based on size, granularity and fluorescence. Cells in suspension are passed as a stream in droplets with each droplet containing a single cell of interest. The droplets are passed in front of a laser. An optical detection system detects cells of interest based on predetermined optical parameters (e.g., fluorescent or bioluminescent parameters). The instrument applies a charge to a droplet containing a cell of interest and an electrostatic deflection system facilitates collection of the charged droplets into appropriate tubes or wells. Sorting parameters may be adjusted depending on the requirement of purity and yield.

MACS™ (Miltenvi Biotec) is a method for separation f various cell populations depending on their surface antigens. This selection process relies on the co-introduction of cell-surface markers that are not otherwise present on the surface of cells to be edited.

Use of the Automated Multi-Module Mammalian Cell Processing Instrument

Figure 6:
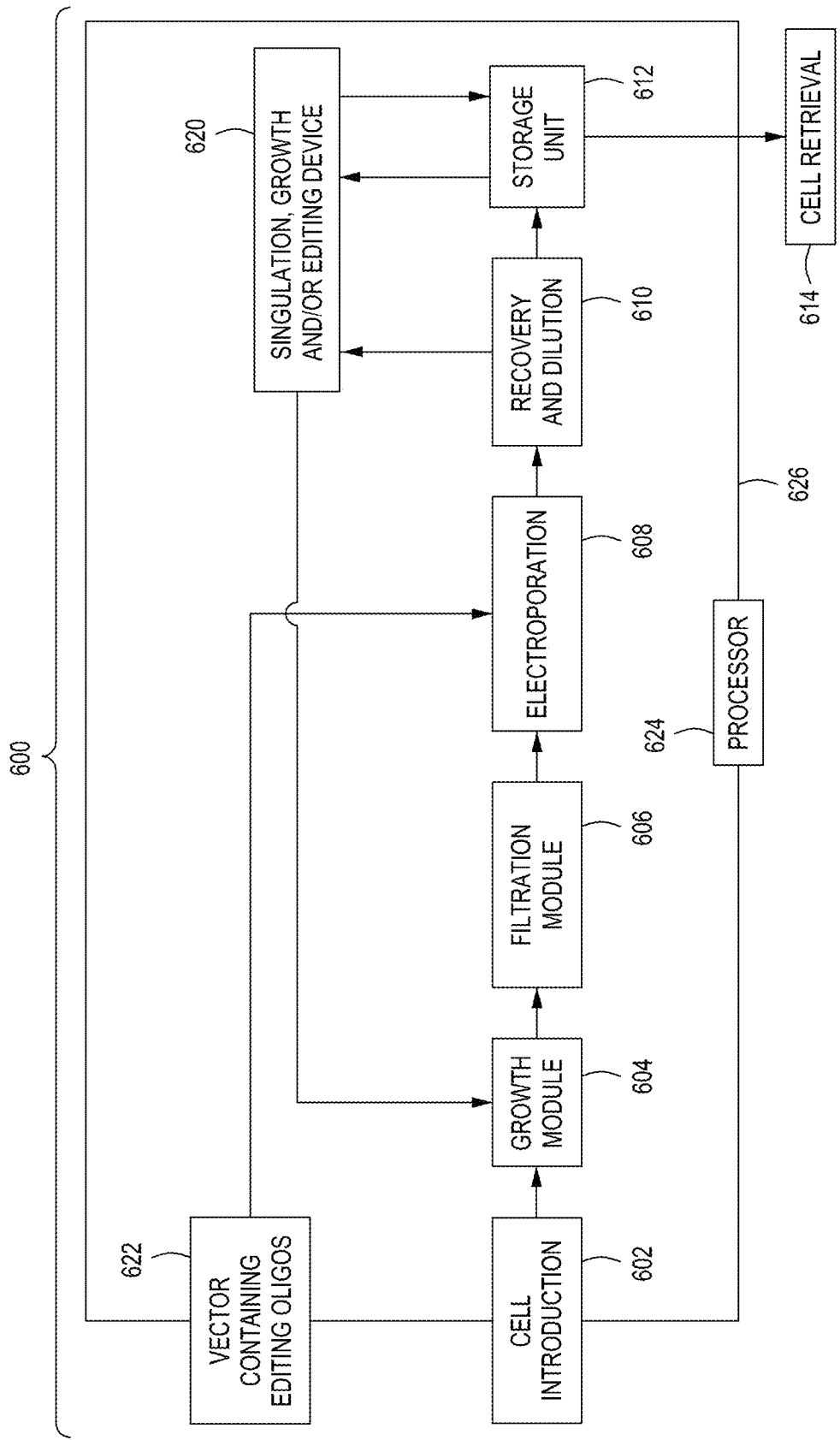
FIG. 6 is a simplified block diagram of an embodiment of an exemplary automated multi-module cell processing instrument.

FIG. 6 illustrates an embodiment of a multi-module cell processing instrument. This embodiment depicts an exemplary system that performs recursive gene editing on a mammalian cell population. The cell processing instrument 600 may include a housing, a reservoir for storing cells to be transformed or transfected 604, and a cell growth and/or concentration module (comprising, e.g., a rotating growth vial) 608. The cells to be transformed are transferred from a reservoir to the cell growth module to be cultured until the cells hit a target OD. Once the cells hit the target OD, the growth module may cool or freeze the cells for later processing proceed to perform cell concentration where the cells are subjected to buffer exchange and rendered electrocompetent, and the volume of the cells may be reduced substantially. Once the cells have been concentrated to an appropriate volume, the cells are transferred to editing machinery introduction module 610, such as a flow-through electroporation device as described above. In addition to the reservoir for storing cells 604, the multi-module cell processing instrument includes a reservoir for storing an editing vector pre-assembled with editing oligonucleotide cassettes 606. The pre-assembled editing vectors are transferred to the editing machinery introduction module 610, which already contains the cell culture grown to a target OD. Additionally, the instrument may comprise a reservoir 602 for storing an engine vector comprising the coding sequence for the nucleic acid-guided nuclease. The engine vectors may be transferred to the editing machinery introduction module 610 and transformed at the same time the editing vectors are transformed, or the engine vectors may be transformed into the cells before or after the editing vectors have been transformed into the cells. In the editing machinery introduction module 610, the nucleic acids are, e.g., electroporated into the cells. Following transformation, the cells are transferred into an optional recovery module (not shown), where the cells recover briefly post-transformation.

After an optional recovery, the cells may be transferred to a storage module (also not shown), where the cells can be stored at, e.g., 4° C. for later processing. In addition, selection may be optionally performed in a separate module between the editing machinery introduction module and the editing module, or selection may be performed in the editing module. Selection in this instance refers to selecting for cells that have been properly transformed with vectors that comprise selection markers, thus assuring that the cells are likely to have received vectors for both nucleic acid-guided nuclease editing and for reporting proper edits. After selection, the cells may optionally be diluted and transferred to an editing module 612. Conditions are then provided such that editing takes place. For example, if one or more of the editing components (e.g., one or more of the nucleic acid-guided nuclease, gRNA or donor DNA) is under control of an inducible promoter, conditions are provided to activate the inducible promoter(s). Once editing has taken place, cells are selected in an enrichment module 614 where the cells are selected, e.g., sorted using FACS or MACS™. Cells expressing the selection marker are separated in the enrichment module from cells that do not express the expression marker, and optionally prepared for another round of editing. The multi-module cell processing instrument is controlled by a processor 616 configured to operate the instrument based on user input, as directed by one or more scripts, or as a combination of user input or a script. The processor 616 may control the timing, duration, temperature, and operations of the various modules of the instrument 600 and the dispensing of reagents from the reagent cartridge. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached a target OD, been rendered competent and concentrated, and/or update the user as to the progress of the cells in the various modules in the multi-module instrument.

It should be apparent to one of ordinary skill in the art given the present disclosure that the process described may be recursive and multiplexed; that is, cells may go through the workflow described in relation to FIG. 6, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries. In any recursive process, it is advantageous to "cure" the previous engine and editing vectors (or single engine+editing vector in a single vector system). "Curing" is a process in which one or more vectors used in the prior round of editing is eliminated from the transformed cells.

Curing can be accomplished by, e.g., cleaving the vector(s) using a curing plasmid thereby rendering the editing and/or engine vector (or single, combined engine/editing vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine vector.

Editing and Selection Workflows for Higher Editing Efficiencies

The combination of nucleic acid-directed nuclease editing methods with selection procedures—either computational or physical, as described further herein—results in a significant increase in editing efficiency in comparison to the editing methods without such selection methods.

In a first set of workflows, shown in FIGS. 7 and 8, the editing workflow consists of the use of a nuclease (e.g., an RNA-directed nuclease such as cas-9, cpf-1, MAD7, and the like) with one or more selection events to increase editing rates in cells, including increasing the editing rates in mammalian cells.

FIG. 7 shows an exemplary workflow in which editing machinery and the coding sequences for an RNA-directed nuclease are delivered to cells in two separate vectors. The workflow includes design of gRNAs targeting the region of a genome to be edited, covalently attached to a homology arm containing one or more intended edits 702. In specific aspects, the edits include an edit to render the target site resistant to further nuclease cleavage, e.g., a mutation in a PAM site and/or spacer region. These gRNA-HA constructs are introduced to editing vectors 704 that includes a promoter for expression of the nucleic acids and optionally includes a barcode or other mechanism to track a specific edit. Optionally, the promoter used to drive the editing machinery is inducible.

The coding sequences for an RNA-directed nuclease (e.g., cas-9, cpf-1, MAD7) are introduced into a second set of vectors 708 to create engine vectors. The engine vectors have the coding sequences of the nuclease under a separate promoter from the editing vectors. The separate promoter of the engine vectors may be the same or different than the promoter used for the editing vector, and optionally is inducible.

The engine vectors and editing vectors are introduced to cells 710, e.g., using transformation, transfection, or other mechanisms that will be apparent to one of skill in the art upon reading the present disclosure. The cells are then provided with conditions for editing the cells 712, and allowed to edit.

Following editing, the cells are selected 714 for the cells enriched for editing using techniques such as those described herein. Such techniques could use computational means of selection for further analysis of the edited cell population as well as physical selection using negative selection and/or positive selection, such as selection of a selection marker e.g., a cell-surface marker that can serve as a handle for physical enrichment of the putatively edited cells.

The steps 710-714 (or in some cases, 712-714 if sufficient editing and/or engine vectors are present in the cell population and do not need to be added again) can optionally be repeated 716 to increase editing efficiency of the cell population.

FIG. 8 shows an exemplary workflow using a single vector system to introduce both the editing nucleic acids and the coding sequences for a nuclease to a cell population to be edited. The workflow includes design of gRNAs targeting the region of a genome to be edited, covalently attached to a homology arm containing one or more intended edits 802. In specific aspects, the edits include an edit to render the target site resistant to further nuclease cleavage, e.g., a mutation in a PAM site and/or spacer region.

These gRNA-HA constructs and coding sequences for a nuclease (e.g., an RNA-directed nuclease) are introduced 804 to the same vectors to create a single vector that includes one or more promoters for expression of the nucleic acids and the nuclease. The single vector optionally includes a barcode or other mechanism to track a specific edit. The vector may contain a single promoter for expression of both the gRNA-HA constructs and coding sequences for a nuclease, or the gRNA-HA constructs and coding sequences for a nuclease may be under the control of different promoters in the same vector. Optionally, the promoter or promoters used to drive the editing machinery and/or the coding for the nuclease are inducible.

The vectors are introduced to cells 810, e.g., using transformation, transfection, or other mechanisms that will be apparent to one of skill in the art upon reading the present disclosure. The cells are then provided with conditions for editing the cells 812, and allowed to edit.

Following editing, the cells are selected 814 for the cells enriched for editing using techniques such as those described herein. Such techniques could use computational means of selection for further analysis of the edited cell population as well as physical selection using negative selection and/or positive selection, such as selection of a selection marker e.g., a cell-surface marker that can serve as a handle for physical enrichment of the putatively edited cells.

The steps 810-814 (or in some cases, 812-814 if sufficient editing and/or engine vectors are present in the cell population and do not need to be added again) can optionally be repeated 816 to increase editing efficiency of the cell population.

FIG. 9 shows an exemplary workflow in which editing machinery and the coding sequences for an RNA-directed nuclease are delivered to cells in two separate vectors. The workflow includes design of gRNAs targeting the region of a genome to be edited, covalently attached to a homology arm containing one or more intended edits 902. In specific aspects, the edits include an edit to render the target site resistant to further nuclease cleavage, e.g., a mutation in a PAM site and/or spacer region. These gRNA-HA constructs are introduced to editing vectors 904 that includes a promoter for expression of the nucleic acids and optionally includes a barcode or other mechanism to track a specific edit. Optionally, the promoter used to drive the editing machinery is inducible.

The coding sequences for a fusion vector of an RNA-directed nuclease (e.g., cas-9, cpf-1, MAD7) and an enzyme region with desired functionality (e.g., reverse transcriptase activity) are introduced into a second set of vectors 908 to create engine vectors. The engine vectors have the coding sequences of the nuclease under a separate promoter from the editing vectors. The separate promoter of the engine vectors may be the same or different that the promoter used for the editing vector, and optionally is inducible.

The engine vectors and editing vectors are introduced to cells 910, e.g., using transformation, transfection, or other mechanisms that will be apparent to one of skill in the art upon reading the present disclosure. The cells are then provided with conditions for editing the cells 912, and allowed to edit.

Following editing, the cells are selected 914 for the cells enriched for editing using techniques such as those described herein. Such techniques could use computational means of selection for further analysis of the edited cell population as well as physical selection using negative selection and/or positive selection, such as selection of a selection marker e.g., a cell-surface marker that can serve as a handle for physical enrichment of the putatively edited cells.

The steps 910-914 (or in some cases, 912-914 if sufficient editing and/or engine vectors are present in the cell population and do not need to be added again) can optionally be repeated 916 to increase editing efficiency of the cell population.

Figure 10:
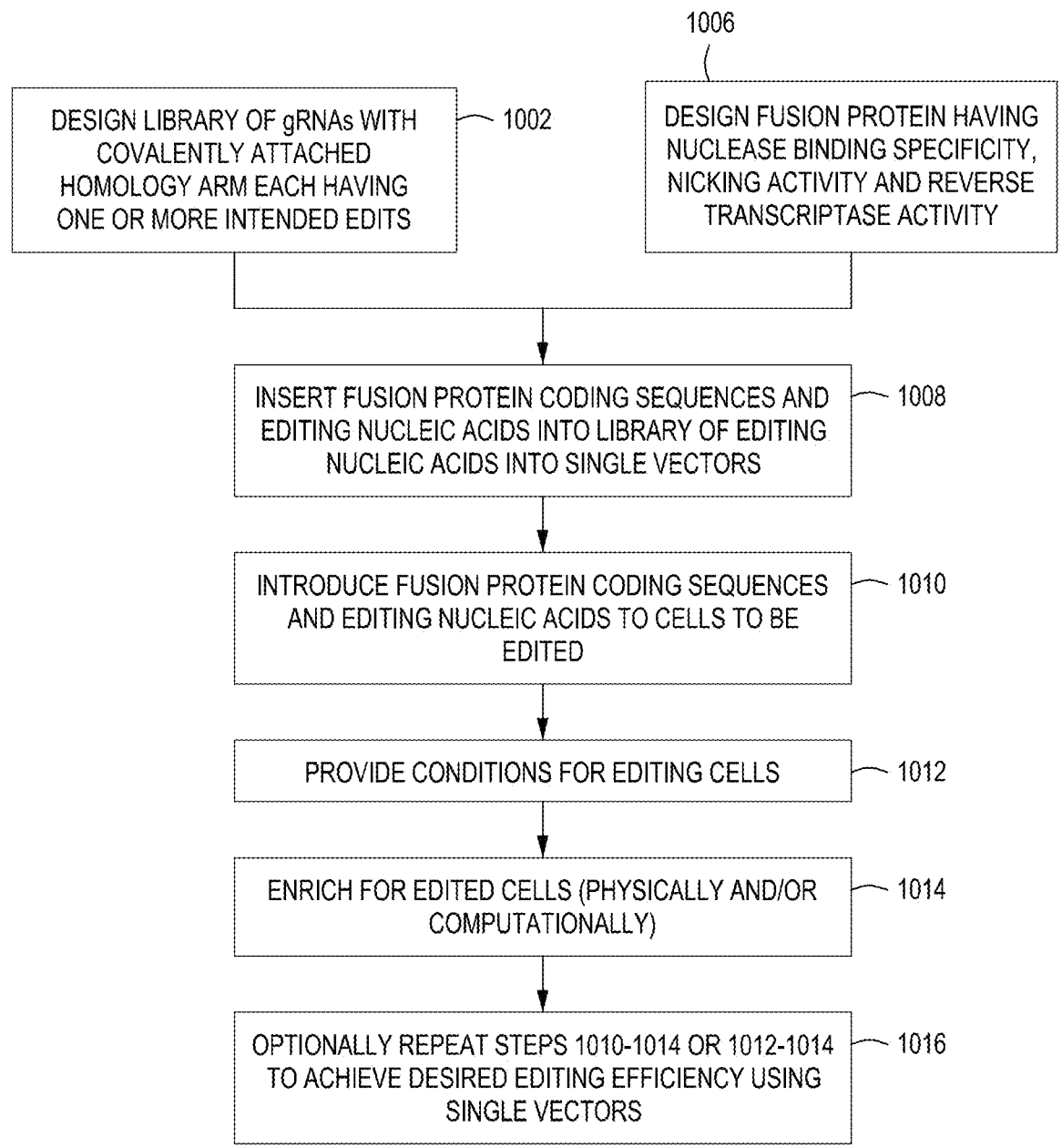
FIG. 10 is a diagram showing a second set of exemplary workflows for carrying out CREATE Fusion protocols of the disclosure.
Figure 11:
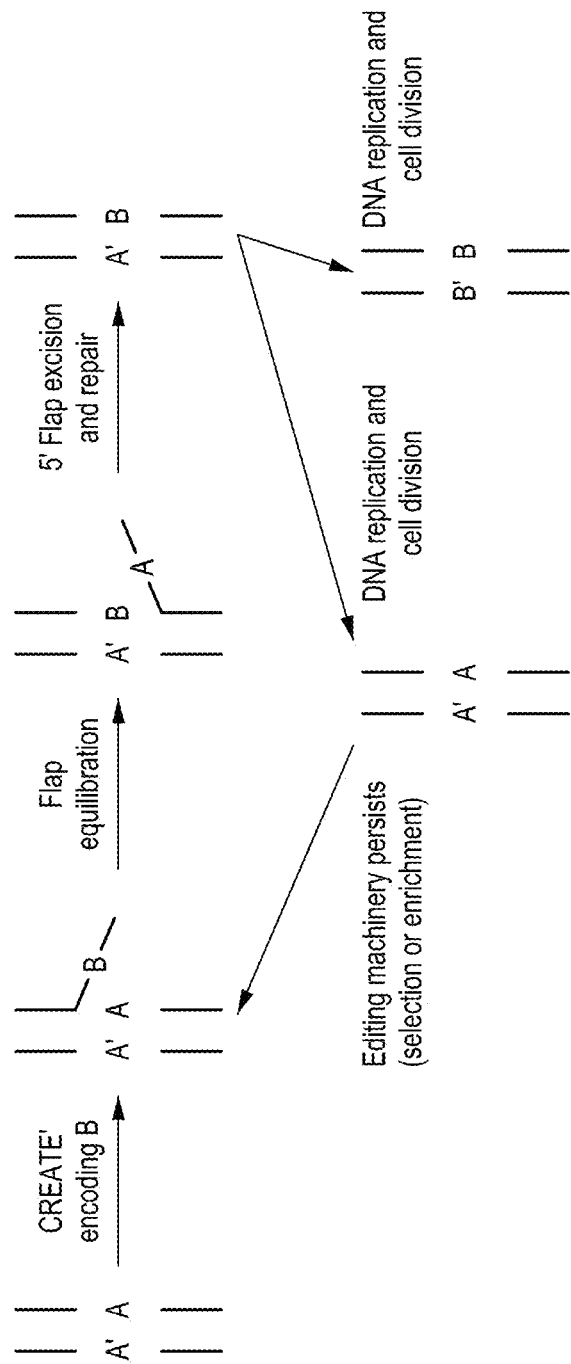
FIG. 11 is a diagram showing potential mechanism for editing using a fusion protein with reverse transcriptase activity over multiple cell cycles.
Figure 12:
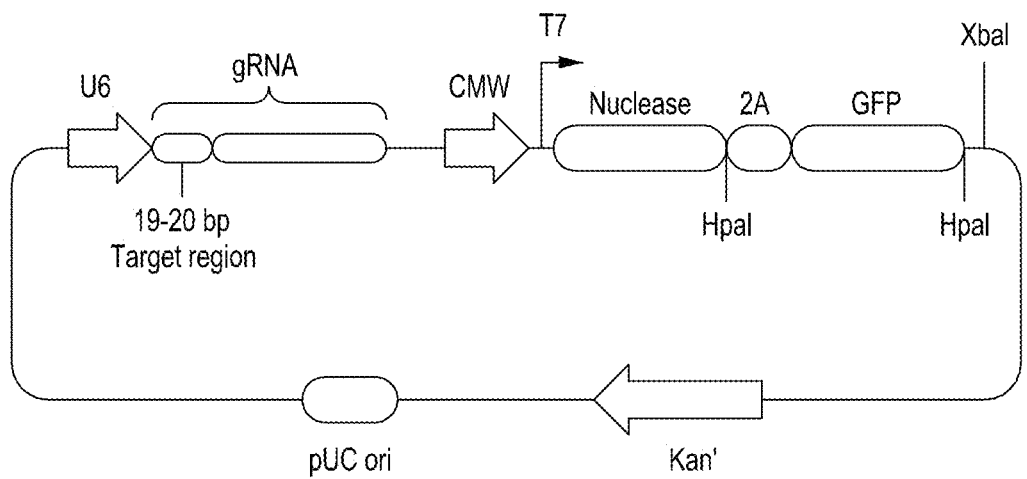
FIG. 12 is a diagram illustrating exemplary elements in a plasmid structure used for the GFP expression assay.

FIG. 10 shows an exemplary workflow using a single vector system to introduce both the editing nucleic acids and the coding sequences for a nuclease to a cell population to be edited. The workflow includes design of gRNAs targeting the region of a genome to be edited, covalently attached to a homology arm containing one or more intended edits 1002. In specific aspects, the edits include an edit to render the target site resistant to further nuclease cleavage, e.g., a mutation in a PAM site and/or spacer region.

These gRNA-HA constructs and coding sequences for a fusion vector of an RNA-directed nuclease (e.g., cas-9, cpf-1, MAD7) and an enzyme region with desired functionality (e.g., reverse transcriptase activity) are introduced into the vectors 1008 to create a single vector that includes one or more promoters for expression of the nucleic acids and the fusion protein. The single vector optionally includes a barcode or other mechanism to track a specific edit. The vector may contain a single promoter for expression of both the gRNA-HA constructs and coding sequences for the fusion protein, or the gRNA-HA constructs and coding sequences for the fusion protein may be under the control of different promoters in the same vector. Optionally, the promoter or promoters used to drive the editing machinery and/or the coding for the fusion protein are inducible.

The vectors are introduced to cells 1010, e.g., using transformation, transfection, or other mechanisms that will be apparent to one of skill in the art upon reading the present disclosure. The cells are then provided with conditions for editing the cells 812, and allowed to edit.

Following editing, the cells are selected 1014 for the cells enriched for editing using techniques such as those described herein. Such techniques could use computational means of selection for further analysis of the edited cell population as well as physical selection using negative selection and/or positive selection, such as selection of a selection marker e.g., a cell-surface marker that can serve as a handle for physical enrichment of the putatively edited cells.

The steps 1010-1014 (or in some cases, 1012-1014 if sufficient editing and/or engine vectors are present in the cell population and do not need to be added again) can optionally be repeated 1016 to increase editing efficiency of the cell population.

Cell Libraries Created Using Automated Editing Methods, Modules, Instruments and Systems In one aspect, the present disclosure provides editing methods, modules, instruments, and automated multi-module cell editing instruments for creating a library of cells that vary the expression, levels and/or activity of RNAs and/or proteins of interest in various cell types using various nickase-based editing strategies, including CREATE fusion, as described herein in more detail. Accordingly, the disclosure is intended to cover edited cell libraries created by the automated editing methods, automated multi-module cell editing instruments of the disclosure. These cell libraries may have different targeted edits, including but not limited to gene knockouts, gene knock-ins, insertions, deletions, single nucleotide edits, short tandem repeat edits, frameshifts, triplet codon expansion, and the like in cells of various organisms. These edits can be directed to coding or non-coding regions of the genome, and are preferably rationally designed.

In some aspects, the present disclosure provides automated editing methods, automated multi-module cell editing instruments for creating a library of cells that vary DNA-linked processes. For example, the cell library may include individual cells having edits in DNA binding sites to interfere with DNA binding of regulatory elements that modulate expression of selected genes. In addition, cell libraries may include edits in genomic DNA that impact on cellular processes such as heterochromatin formation, switch-class recombination and VDJ recombination.

In specific aspects, the cell libraries are created using multiplexed, nickase-directed editing of individual cells within a cell population, with multiple cells within a cell population are edited in a single round of editing, i.e., multiple changes within the cells of the cell library are in a single automated operation. The libraries that can be created in a single multiplexed automated operation can comprise as many as 500 cells with intended edits, which may be the same introduced edit in the cells or two or more discrete edits in different cells. The libraries can also include one or more intended edits (the same or different) in 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

In other specific aspects, the cell libraries are created using nickase-directed recursive editing of individual cells within a cell population, with edits being added to the individual cells in two or more rounds of editing. The use of recursive editing results in the amalgamation of two or more edits targeting two or more sites in the genome in individual cells of the library. The libraries that can be created in a single multiplexed automated operation can comprise as many as 500 cells with intended edits, which may be the same introduced edit in the cells or two or more discrete edits in different cells. The libraries can also include one or more intended edits (the same or different) in 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

Examples of non-automated editing strategies that can be modified based on the present specification to utilize the automated systems can be found, e.g., in Liu et al., supra.

In specific aspects, recursive editing can be used to first create a cell phenotype, and then later rounds of editing used to reverse the phenotype and/or accelerate other cell properties.

In some aspects, the cell library comprises edits for the creation of unnatural amino acids in a cell.

In specific aspects, the disclosure provides edited cell libraries having edits in one or more regulatory elements created using the disclosed editing methods, automated multi-module cell editing instruments of the disclosure. The term "regulatory element" refers to nucleic acid molecules that can influence the transcription and/or translation of an operably linked coding sequence in a particular environment and/or context. This term is intended to include all elements that promote or regulate transcription, and RNA stability including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include, but are not limited to, promoters, operator sequences and a ribosome binding sites. Regulatory elements that are used in eukaryotic cells may include, but are not limited to, promoters, enhancers, insulators, splicing signals and polyadenylation signals.

Preferably, the edited cell library includes rationally designed edits that are designed based on predictions of protein structure, expression and/or activity in a particular cell type. For example, rational design may be based on a system-wide biophysical model of genome editing with a particular nuclease and gene regulation to predict how different editing parameters including nuclease expression and/or binding, growth conditions, and other experimental conditions collectively control the dynamics of nuclease editing. See, e.g., Farasat and Salis, PLoS Comput Biol., 29:12(1):e1004724 (2016).

In one aspect, the present disclosure provides the creation of a library of edited cells with various rationally designed regulatory sequences created using the nickase methods of the disclosure, including automated methods using the disclosed instrument. For example, the edited cell library can include prokaryotic cell populations created using set of constitutive and/or inducible promoters, enhancer sequences, operator sequences and/or ribosome binding sites. In another example, the edited cell library can include eukaryotic sequences created using a set of constitutive and/or inducible promoters, enhancer sequences, operator sequences, and/or different Kozak sequences for expression of proteins of interest.

In some aspects, the disclosure provides cell libraries including cells with rationally designed edits comprising one or more classes of edits in sequences of interest across the genome of an organism. In specific aspects, the disclosure provides cell libraries including cells with rationally designed edits comprising one or more classes of edits in sequences of interest across a subset of the genome. For example, the cell library may include cells with rationally designed edits comprising one or more classes of edits in sequences of interest across the exome, e.g., every or most open reading frames of the genome. For example, the cell library may include cells with rationally designed edits comprising one or more classes of edits in sequences of interest across the kinome. In yet another example, the cell library may include cells with rationally designed edits comprising one or more classes of edits in sequences of interest across the secretome. In yet other aspects, the cell library may include cells with rationally designed edits created to analyze various isoforms of proteins encoded within the exome, and the cell libraries can be designed to control expression of one or more specific isoforms, e.g., for transcriptome analysis.

Importantly, in certain aspects the cell libraries may comprise edits using randomized sequences, e.g., randomized promoter sequences, to reduce similarity between expression of one or more proteins in individual cells within the library. Additionally, the promoters in the cell library can be constitutive, inducible or both to enable strong and/or titratable expression.

In other aspects, the present disclosure provides nickase-based editing methods, modules, instruments and systems employing automated editing methods, and/or automated multi-module cell editing instruments for creating a library of cells comprising edits to identify optimum expression of a selected gene target. For example, production of biochemicals through metabolic engineering often requires the expression of pathway enzymes, and the best production yields are not always achieved by the highest amount of the target pathway enzymes in the cell, but rather by fine-tuning of the expression levels of the individual enzymes and related regulatory proteins and/or pathways. Similarly, expression levels of heterologous proteins sometimes can be experimentally adjusted for optimal yields.

The most obvious way that transcription impacts on gene expression levels is through the rate of Pol II initiation, which can be modulated by combinations of promoter or enhancer strength and trans-activating factors (Kadonaga, et al., Cell, 116(2):247-57 (2004). In eukaryotes, elongation rate may also determine gene expression patterns by influencing alternative splicing (Cramer et al., PNAS USA, 94(21):11456-60 (1997). Failed termination on a gene can impair the expression of downstream genes by reducing the accessibility of the promoter to Pol II (Greger, et al., 2000 PNAS USA, 97(15):8415-20 (2000). This process, known as transcriptional interference, is particularly relevant in lower eukaryotes, as they often have closely spaced genes. In some embodiments, the present disclosure provides methods for optimizing cellular gene transcription. Gene transcription is the result of several distinct biological phenomena, including transcriptional initiation (RNAp recruitment and transcriptional complex formation), elongation (strand synthesis/extension), and transcriptional termination (RNAp detachment and termination).

Site Directed Mutagenesis

Cell libraries can be created using the nickase-based editing methods, modules, instruments and systems employing site-directed mutagenesis, i.e., when the amino acid sequence of a protein or other genomic feature may be altered by deliberately and precisely by mutating the protein or genomic feature. These cell lines can be useful for various purposes, e.g., for determining protein function within cells, the identification of enzymatic active sites within cells, and the design of novel proteins. For example, site-directed mutagenesis can be used in a multiplexed fashion to exchange a single amino acid in the sequence of a protein for another amino acid with different chemical properties. This allows one to determine the effect of a rationally designed or randomly generated mutation genes in individual cells within a cell population. See, e.g., Berg, et al. Biochemistry, Sixth Ed. (New York: W.H. Freeman and Company) (2007).

In another example, edits can be made to individual cells within a cell library to substitute amino acids in binding sites, such as substitution of one or more amino acids in a protein binding site for interaction within a protein complex or substitution of one or more amino acids in enzymatic pockets that can accommodate a cofactor or ligand. This class of edits allows the creation of specific manipulations to a protein to measure certain properties of one or more proteins, including interaction with other cofactors, ligands, etc. within a protein complex.

In yet another examples, various edit types can be made to individual cells within a cell library using site specific mutagenesis for studying expression quantitative trait loci (eQTLs). An eQTL is a locus that explains a fraction of the genetic variance of a gene expression phenotype. The libraries of the invention would be useful to evaluate and link eQTLs to actual diseased states.

In specific aspects, the edits introduced into the cell libraries of the disclosure may be created using rational design based on known or predicted structures of proteins. See, e.g., Chronopoulou E G and Labrou, Curr Protoc Protein Sci.; Chapter 26:Unit 26.6 (2011). Such site-directed mutagenesis can provide individual cells within a library with one or more site-directed edits, and preferably two or more site-directed edits (e.g., combinatorial edits) within a cell population.

In other aspects, cell libraries of the disclosure are created using site-directed codon mutation "scanning" of all or substantially all of the codons in the coding region of a gene. In this fashion, individual edits of specific codons can be examined for loss-of-function or gain-of-function based on specific polymorphisms in one or more codons of the gene. These libraries can be a powerful tool for determining which genetic changes are silent or causal of a specific phenotype in a cell or cell population. The edits of the codons may be randomly generated or may be rationally designed based on known polymorphisms and/or mutations that have been identified in the gene to be analyzed. Moreover, using these techniques on two or more genes in a single in a pathway in a cell, may determine potential protein:protein interactions or redundancies in cell functions or pathways.

For example, alanine scanning can be used to determine the contribution of a specific residue to the stability or function of given protein. See, e.g., Lefèvre, et al., Nucleic Acids Research, Volume 25(2):447-448 (1997). Alanine is often used in this codon scanning technique because of its non-bulky, chemically inert, methyl functional group that can mimic the secondary structure preferences that many of the other amino acids possess. Codon scanning can also be used to determine whether the side chain of a specific residue plays a significant role in cell function and/or activity. Sometimes other amino acids such as valine or leucine can be used in the creation of codon scanning cell libraries if conservation of the size of mutated residues is needed.

In other specific aspects, cell libraries can be created using the nickase-based editing methods, modules, instruments and systems employing automated editing methods, and/or automated multi-module cell editing instruments of the disclosure to determine the active site of a protein such as an enzyme or hormone, and to elucidate the mechanism of action of one or more of these proteins in a cell library. Site-directed mutagenesis associated with molecular modeling studies can be used to discover the active site structure of an enzyme and consequently its mechanism of action. Analysis of these cell libraries can provide an understanding of the role exerted by specific amino acid residues at the active sites of proteins, in the contacts between subunits of protein complexes, on intracellular trafficking and protein stability/half-life in various genetic backgrounds.

Saturation Mutagenesis

In some aspects, the cell libraries created using nickase-based editing methods, modules, instruments and systems employing automated editing methods, and/or automated multi-module cell editing instruments are saturation mutagenesis libraries, in which a single codon or set of codons is randomized to produce all possible amino acids at the position of a particular gene or genes of interest. These cell libraries can be particularly useful to generate variants, e.g., for directed evolution. See, e.g., Chica, et al., Current Opinion in Biotechnology 16 (4): 378-384 (2005); and Shivange, Current Opinion in Chemical Biology, 13 (1): 19-25.

In some aspects, edits comprising different degenerate codons can be used to encode sets of amino acids in the individual cells in the libraries. Because some amino acids are encoded by more codons than others, the exact ratio of amino acids cannot be equal. In certain aspects, more restricted degenerate codons are used. 'NNK' and 'NNS' have the benefit of encoding all 20 amino acids, but still encode a stop codon 3% of the time. Alternative codons such as 'NDT', 'DBK' avoid stop codons entirely, and encode a minimal set of amino acids that still encompass all the main biophysical types (anionic, cationic, aliphatic hydrophobic, aromatic hydrophobic, hydrophilic, small).

In specific aspects, the non-redundant saturation mutagenesis, in which the most commonly used codon for a particular organism, is used in the saturation mutagenesis editing process.

Promoter Swaps and Ladders

One mechanism for analyzing and/or optimizing expression of one or more genes of interest is through the creation of a "promoter swap" cell library, in which the cells comprise genetic edits that have specific promoters linked to one or more genes of interest. Accordingly, the cell libraries created nickase-based editing methods, modules, instruments and systems employing automated editing methods, and/or automated multi-module cell editing instruments may be promoter swap cell libraries, which can be used, e.g., to increase or decrease expression of a gene of interest to optimize a metabolic or genetic pathway. In some aspects, the promoter swap cell library can be used to identify an increase or reduction in the expression of a gene that affects cell vitality or viability, e.g., a gene encoding a protein that impacts on the growth rate or overall health of the cells. In some aspects, the promoter swap cell library can be used to create cells having dependencies and logic between the promoters to create synthetic gene networks. In some aspects, the promoter swaps can be used to control cell to cell communication between cells of both homogeneous and heterogeneous (complex tissues) populations in nature.

The cell libraries can utilize any given number of promoters that have been grouped together based upon exhibition of a range of expression strengths and any given number of target genes. The ladder of promoter sequences vary expression of at least one locus under at least one condition. This ladder is then systematically applied to a group of genes in the organism using the automated editing methods, automated multi-module cell editing instruments of the disclosure.

In specific aspects, the cell library formed using nickase-based editing methods include individual cells that are representative of a given promoter operably linked to one or more target genes of interest in an otherwise identical genetic background. Examples of non-automated editing strategies that can be modified to utilize the automated systems can be found, e.g., in U.S. Pat. No. 9,988,624.

In specific aspects, the promoter swap cell library is produced by editing a set of target genes to be operably linked to a pre-selected set of promoters that act as a "promoter ladder" for expression of the genes of interest. For example, the cells are edited so that one or more individual genes of interest are edited to be operably linked with the different promoters in the promoter ladder. When an endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context. The promoters are generally selected to result in variable expression across different loci, and may include inducible promoters, constitutive promoters, or both.

The set of target genes edited using the promoter ladder can include all or most open reading frames (ORFs) in a genome, or a selected subset of the genome, e.g., the ORFs of the kinome or a secretome. In some aspects, the target genes can include coding regions for various isoforms of the genes, and the cell libraries can be designed to expression of one or more specific isoforms, e.g., for transcriptome analysis using various promoters.

The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

Editing of other functional genetic elements, including insulator elements and other genomic organization elements, can also be used to systematically vary the expression level of a set of target genes, and can be introduced using the methods, automated multi-module cell editing instruments of the disclosure. In one aspect, a population of cells is edited using a ladder of enhancer sequences, either alone or in combination with selected promoters or a promoter ladder, to create a cell library having various edits in these enhancer elements. In another aspect, a population of cells is edited using a ladder of ribosome binding sequences, either alone or in combination with selected promoters or a promoter ladder, to create a cell library having various edits in these ribosome binding sequences.

In another aspect, a population of cells is edited to allow the attachment of various mRNA and/or protein stabilizing or destabilizing sequences to the 5' or 3' end, or at any other location, of a transcript or protein.

In certain aspects, a population of cells of a previously established cell line may be edited using the automated editing methods, modules, instruments, and systems of the disclosure to create a cell library to improve the function, health and/or viability of the cells. For example, many industrial strains currently used for large scale manufacturing have been developed using random mutagenesis processes iteratively over a period of many years, sometimes decades. Unwanted neutral and detrimental mutations were introduced into strains along with beneficial changes, and over time this resulted in strains with deficiencies in overall robustness and key traits such as growth rates. In another example, mammalian cell lines continue to mutate through the passage of the cells over periods of time, and likewise these cell lines can become unstable and acquire traits that are undesirable. The automated editing methods, automated multi-module cell editing instruments of the disclosure can use editing strategies such as SNP and/or STR swapping, indel creation, or other techniques to remove or change the undesirable genome sequences and/or introducing new genome sequences to address the deficiencies while retaining the desirable properties of the cells.

When recursive editing is used, the editing in the individual cells in the edited cell library can incorporate the inclusion of "landing pads" in an ectopic site in the enome (e.g., a CarT locus) to optimize expression, stability and/or control.

In some embodiments, each library produced having individual cells comprising one or more edits (either introducing or removing) is cultured and analyzed under one or more criteria (e.g., production of a chemical or product of interest). The cells possessing the specific criteria are then associated, or correlated, with one or more particular edits in the cell. In this manner, the effect of a given edit on any number of genetic or phenotypic traits of interest can be determined. The identification of multiple edits associated with particular criteria or enhanced functionality/robustness may lead to cells with highly desirable characteristics.

Knock-Out or Knock-in Libraries

In certain aspects, the cell libraries created using nickase-based editing methods, modules, instruments and systems employing automated editing methods, and/or automated multi-module cell editing instruments may be "knock-out" (KO) or "knock-in" (KI) edits of various genes of interest. Thus, the disclosure is intended to cover edited cell libraries created by the nickase-based editing methods, modules, instruments and systems employing automated editing methods, and/or automated multi-module cell editing instruments that have one or more mutations that remove or reduce the expression of selected genes of interest to interrogate the effect of these edits on gene function in individual cells within the cell library.

The cell libraries can be created using targeted gene KO (e.g., via insertion/deletion) or KOs (e.g., via homologous directed repair). For example, double strand breaks are often repaired via the non-homologous end joining DNA repair pathway. The repair is known to be error prone, and thus insertions and deletions may be introduced that can disrupt gene function. Preferably the edits are rationally designed to specifically affect the genes of interest, and individual cells can be created having a KI or KI of one or more locus of interest. Cells having a KO or KI of two or more loci of interest can be created using automated recursive editing of the disclosure.

In specific aspects, the KO or KI cell libraries are created using simultaneous multiplexed editing of cells within a cell population, and multiple cells within a cell population are edited in a single round of editing, i.e., multiple changes within the cells of the cell library are in a single automated operation. In other specific aspects, the cell libraries are created using recursive editing of individual cells within a cell population, and results in the amalgamation of multiple edits of two or more sites in the genome into single cells.

SNP or Short Tandem Repeat Swaps

In one aspect, cell libraries created using nickase-based editing methods, modules, instruments and systems employing automated editing methods, and/or automated multi-module cell editing instruments may be produced for systematically introducing or substituting single nucleotide polymorphisms ("SNPs") into the genomes of the individual cells to create a "SNP swap" cell library. In some embodiments, the SNP swapping methods of the present disclosure include both the addition of beneficial SNPs, and removing detrimental and/or neutral SNPs. The SNP swaps may target coding sequences, non-coding sequences, or both.

In another aspect, a cell library is created using nickase-based editing methods, modules, instruments and systems employing automated editing methods, and/or automated multi-module cell editing instruments for systematically introducing or substituting short tandem repeats ("STR") into the genomes of the individual cells to create an "STR swap" cell library. In some embodiments, the STR swapping methods of the present disclosure include both the addition of beneficial STRs, and removing detrimental and/or neutral STRs. The STR swaps may target coding sequences, non-coding sequences, or both.

In some embodiments, the SNP and/or STR swapping used to create the cell library is multiplexed, and multiple cells within a cell population are edited in a single round of editing, i.e., multiple changes within the cells of the cell library are in a single automated operation. In other embodiments, the SNP and/or STR swapping used to create the cell library is recursive, and results in the amalgamation of multiple beneficial sequences and/or the removal of detrimental sequences into single cells. Multiple changes can be either a specific set of defined changes or a partly randomized, combinatorial library of mutations. Removal of detrimental mutations and consolidation of beneficial mutations can provide immediate improvements in various cellular processes. Removal of genetic burden or consolidation of beneficial changes into a strain with no genetic burden also provides a new, robust starting point for additional random mutagenesis that may enable further improvements.

SNP swapping overcomes fundamental limitations of random mutagenesis approaches as it is not a random approach, but rather the systematic introduction or removal of individual mutations across cells.

Splice Site Editing

RNA splicing is the process during which introns are excised and exons are spliced together to create the mRNA that is translated into a protein. The precise recognition of splicing signals by cellular machinery is critical to this process. Accordingly, cell libraries of the disclosure include a cell library created using nickase-based editing methods, modules, instruments and systems employing automated editing methods, and/or automated multi-module cell editing instruments for systematically introducing changes to known and/or predicted splice donor and/or acceptor sites in various loci to create a library of splice site variants of various genes. Such editing can help to elucidate the biological relevance of various isoforms of genes in a cellular context. Sequences for rational design of splicing sites of various coding regions, including actual or predicted mutations associated with various mammalian disorders, can be predicted using analysis techniques such as those found in Nalla and Rogan, Hum Mutat, 25:334-342 (2005); Divina, et al., Eur J Hum Genet, 17:759-765 (2009); Desmet, et el., Nucleic Acids Res, 37:e67 (2009); Faber, et al., BMC Bioinformatics, 12(suppl 4):S2 (2011).

Start/Stop Codon Exchanges and Incorporation of Nucleic Acid Analogs

In some aspects, the present disclosure provides for the creation of cell libraries created using nickase-based editing methods, modules, instruments and systems employing automated editing methods, and/or automated multi-module cell editing instruments for swapping start and stop codon variants throughout the genome of an organism or for a selected subset of coding regions in the genome, e.g., the kinome or secretome. In the cell library, individual cells will have one or more start or stop codons replacing the native start or stop codon for one or more gene of interest.

For example, typical start codons used by eukaryotes are ATG (AUG) and prokaryotes use ATG (AUG) the most, followed by GTG (GUG) and TTG (UUG). The cell library may include individual cells having substitutions for the native start codons for one or more genes of interest.

In some aspects, the present disclosure provides for creation of a cell library by replacing ATG start codons with TTG in front of selected genes of interest. In other aspects, the present disclosure provides for automated creation of a cell library by replacing ATG start codons with GTG. In other aspects, the present disclosure provides for automated creation of a cell library by replacing GTG start codons with ATG. In other aspects, the present disclosure provides for automated creation of a cell library by replacing GTG start codons with TTG. In other aspects, the present disclosure provides for automated creation of a cell library by replacing TTG start codons with ATG. In other aspects, the present disclosure provides for automated creation of a cell library by replacing TTG start codons with GTG.

In other examples, typical stop codons for *S. cerevisiae* and mammals are TAA (UAA) and TGA (UGA), respectively. The typical stop codon for monocotyledonous plants is TGA (UGA), whereas insects and *E. coli* commonly use TAA (UAA) as the stop codon (Dalphin. et al., Nucl. Acids Res., 24: 216-218 (1996)). The cell library may include individual cells having substitutions for the native stop codons for one or more genes of interest.

In some aspects, the present disclosure provides for automated creation of a cell library by replacing TAA stop codons with TAG. In other aspects, the present disclosure provides for automated creation of a cell library by replacing TAA stop codons with TGA. In other aspects, the present disclosure provides for automated creation of a cell library by replacing TGA stop codons with TAA. In other aspects, the present disclosure provides for automated creation of a cell library by replacing TGA stop codons with TAG. In other aspects, the present disclosure provides for automated creation of a cell library by replacing TAG stop codons with TAA. In other aspects, the present invention teaches automated creation of a cell library by replacing TAG stop codons with TGA.

Terminator Swaps and Ladders

One mechanism for identifying optimum termination of a pre-spliced mRNA of one or more genes of interest is through the creation of a "terminator swap" cell library, in which the cells comprise genetic edits that have specific terminator sequences linked to one or more genes of interest. Accordingly, cell libraries of the disclosure include a terminator swap cell library created using nickase-based editing methods, modules, instruments and systems employing automated editing methods, and/or automated multi-module cell editing instruments. Terminator swap cell libraries can be used, e.g., to affect mRNA stability by releasing transcripts from sites of synthesis. In other embodiments, the terminator swap cell library can be used to identify an increase or reduction in the efficiency of transcriptional termination and thus accumulation of unspliced pre-mRNA (e.g., West and Proudfoot, Mol Cell.; 33(3-9); 354-364 (2009) and/or 3' end processing (e.g., West, et al., Mol Cell. 29(5):600-10 (2008)). In the case where a gene is linked to multiple termination sites, the edits may edit a combination of edits to multiple terminators that are associated with a gene. Additional amino acids may also be added to the ends of proteins to determine the effect on the protein length on terminators.

The cell libraries can utilize any given number of edits of terminators that have been selected for the terminator ladder based upon exhibition of a range of activity and any given number of target genes. The ladder of terminator sequences vary expression of at least one locus under at least one condition. This ladder is then systematically applied to a group of genes in the organism using the automated editing methods, modules, instruments and systems of the disclosure. In some aspects, the present disclosure provides for the creation of cell libraries using the automated editing methods, modules, instruments and systems of disclosure, where the libraries are created to edit terminator signals in one or more regions in the genome in the individual cells of the library. Transcriptional termination in eukaryotes operates through terminator signals that are recognized by protein factors associated with the RNA polymerase II. For example, the cell library may contain individual eukaryotic cells with edits in genes encoding polyadenylation specificity factor (CPSF) and cleavage stimulation factor (CstF) and or gene encoding proteins recruited by CPSF and CstF factors to termination sites. In prokaryotes, two principal mechanisms, termed Rho-independent and Rho-dependent termination, mediate transcriptional termination. For example, the cell library may contain individual prokaryotic cells with edits in genes encoding proteins that affect the binding, efficiency and/or activity of these termination pathways.

In certain aspects, the present disclosure provides methods of selecting termination sequences ("terminators") with optimal properties. For example, in some embodiments, the present disclosure teaches provides methods for introducing and/or editing one or more terminators and/or generating variants of one or more terminators within a host cell, which exhibit a range of activity. A particular combination of terminators can be grouped together as a terminator ladder, and cell libraries of the disclosure include individual cells that are representative of terminators operably linked to one or more target genes of interest in an otherwise identical genetic background. Examples of non-automated editing strategies that can be modified to utilize the automated instruments can be found, e.g., in U.S. Pat. No. 9,988,624 to Serber et al., entitled "Microbial strain improvement by a HTP genomic engineering platform."

In specific aspects, the terminator swap cell library is produced by editing a set of target genes to be operably linked to a pre-selected set of terminators that act as a "terminator ladder" for expression of the genes of interest. For example, the cells are edited so that the endogenous promoter is operably linked to the individual genes of interest are edited with the different promoters in the promoter ladder. When the endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context. The terminator ladder in question is then associated with a given gene of interest.

The terminator ladder can be used to more generally affect termination of all or most ORFs in a genome, or a selected subset of the genome, e.g., the ORFs of a kinome or a secretome. The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Fully-Automated Singleplex RGN-Directed Editing Run

Singleplex automated genomic editing using MAD7 nuclease was successfully performed with an automated multi-module instrument as described in, e.g., U.S. Pat. No. 9,982,279; and U.S. Ser. No. 16/024,831 filed 30 Jun. 2018; Ser. No. 16/024,816 filed 30 Jun. 2018; Ser. No. 16/147,353 filed 28 Sep. 2018; Ser. No. 16/147,865 filed 30 Sep. 2018; and Ser. No. 16/147,871 filed 30 Jun. 2018.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent cells were transferred into a editing machinery introduction module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example II: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent *E. Coli* cells were transferred into a editing machinery introduction module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in an isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent cells (that were transformed with and selected for the first editing vector) were transferred into a editing machinery introduction module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

Cells are transfected with an editing cassette plasmid that mediates expression of a gene-specific gRNA with or without a DNA sequence to mediate precise genomic edits (HDR donor). This plasmid also expresses a handle to enable enrichment (cell surface receptor, fluorescent protein, antibiotic resistance gene) of cells that have been functionally transfected with the editing cassette plasmid. Cells are also co-transfected with nuclease (plasmid, mRNA, protein) that, when paired with the gene-specific gRNA can mediate DNA sequence specific endonuclease activity at genomic targets After delivery of an enrichment-competent editing cassette, the enrichment handle must be expressed to levels that support specific positive selection of transfected cells while allowing for depletion of cells that did not receive an enrichment-competent editing cassette. In certain instances, the expression level of the enrichment reporter may enable enrichment of sub-populations that have significantly higher or lower levels of the enrichment reporter.

Surface reporter-expressing cells can be specifically labeled using fluorophore-conjugated antibodies and then sorted into different populations (receptor-negative, high, or low) using a Fluorescence Activated Cell Sorter (FACS). By electronically gating on cells with different levels of fluorescence intensity one can specifically enrich for subpopulations that have taken up relatively more or fewer copies of the editing cassette. As observed in a GFP-to-BFP analysis performed on the enriched populations versus unenriched populations, certain subpopulations of enrichment of cells have demonstrated higher rates of editing as measured by the relative percentages, of GFP-positive, BFP-positive, and double-negative cells. Enrichment via cell-surface displayed receptors or affinity ligands has also been performed using antibody-coupled magnetic beads.

Example III: Development of GFP Expression Assay

An editing detection assay was developed using RNA-directed nuclease-GFP expression cassettes which expedites genome editing workflows from initial nuclease screening to the final stages of single cell cloning. This vector also included a U6-gRNA cassette creating a single vector system for CRISPR/nuclease delivery and expression (FIG. 10).

Two systems were developed to assist in enriching cell populations for desired genome edits, e.g., using cell sorting. The first system used a single-vector, with the co-expression of the RNA-directed nuclease (e.g., the Cas9 nuclease or the MAD7 nuclease) and GFP from the same mRNA, and a two-plasmid system in which the RNA-directed nuclease was expressed on a separate vector. The single vector system described here contained a T7 promoter for in vitro transcription of nuclease-GFP mRNA (FIG. 10).

The ability to detect and enrich via GFP expression significantly reduces labor and cost associated with single cell cloning and genotyping in genome editing applications. The following data set illustrates how our single vector system can be used for expression monitoring and FACS enrichment of low and high level cutting. In particular, the single plasmid GFP format ensured that all required CRISPR/nuclease components (e.g. MAD7 and gRNA coding sequences) are effectively delivered to GFP positive cells.

Figure 13B:
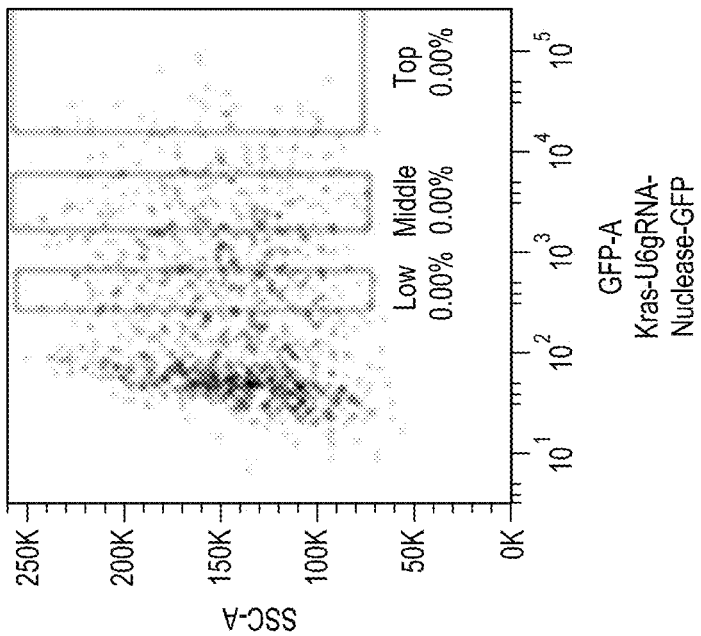
FIGS. 13A and 13B are plots showing the delivery of Nuclease-GFP expression cassettes as monitored by FACS.
Figure 13A:
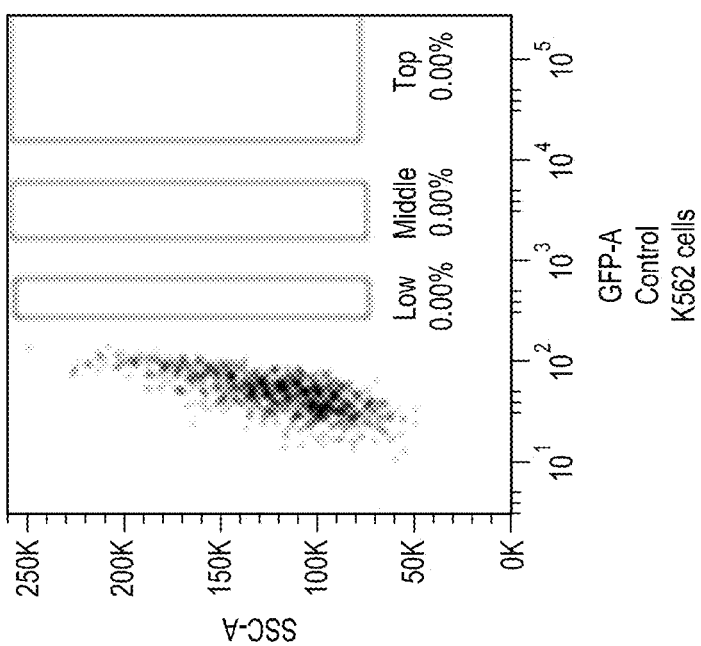

The cell fractions were divided into low, medium, and high pools based on GFP expression, and corresponding increases in indel activity were observed. For a gRNA targeting the KRAS locus, a 4-fold increase in indel activity was observed when comparing the unsorted population vs. the top 2% of cells with the highest GFP expression (See FIGS. 13A and 13B). Not all targeted gRNA designs produce detectable indel activity when initial nuclease screens are done against gene targets, and current gRNA design rules fail to predict activity based on sequence content or genomic context. A gRNA design for CCR5 which initially failed to produce detectable indels, when sorted it into low, medium, and high GFP fractions, indel activity could be detected in the medium and high GFP fractions.

The GFP reporter allowed for quick detection of transfection efficiency saving time and cost associated with downstream expression quantification assays. This assay also allowed for rapid troubleshooting of plasmid delivery and expression problems associated with particular cell types. If GFP expression and nuclease indel activity cannot be observed in a particular cell type despite repeated attempts, using the nuclease-GFP mRNA can circumvent promoter/cell-type incompatibilities.

Example IV: GFP to BFP Conversion Assay

Figure 14B:
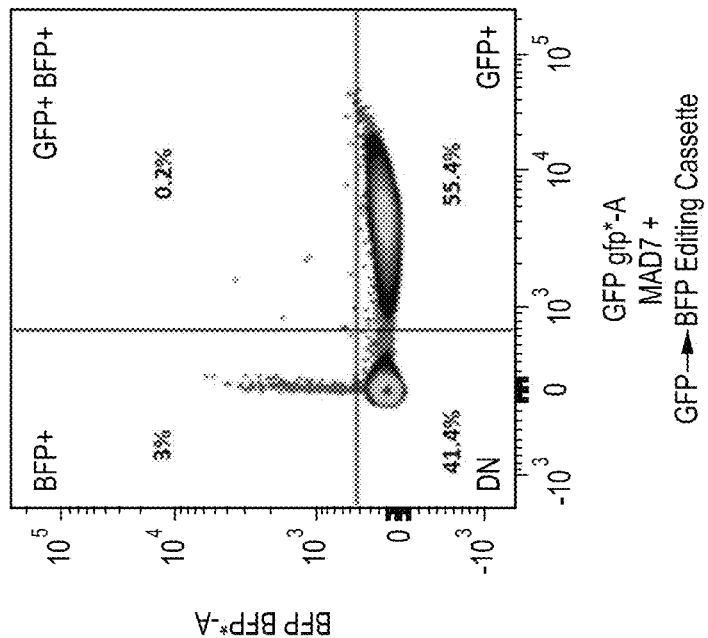
FIGS. 14A and 14B are plots showing GFP to BFP conversion for phenotypic assessment of NHEJ and HDR-mediated editing.
Figure 14A:
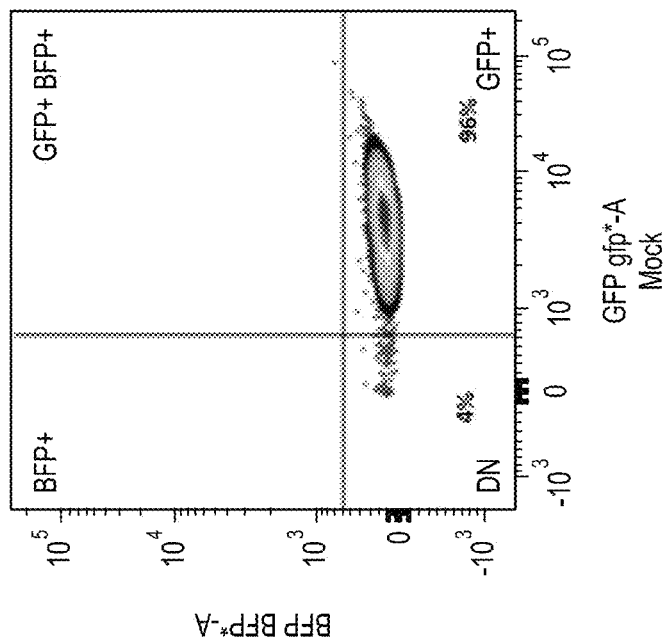

A GFP to BFP reporter cell line was created using mammalian cells with a stably integrated genomic copy of the GFP gene (HEK293T-GFP). These cell lines enabled phenotypic detection of genomic edits of different classes (NHEJ, HDR, no edit) by various different mechanisms, including flow cytometry, fluorescent cell imaging, and genotypic detection by sequencing of the genome-integrated GFP gene. Lack of editing, or perfect repair of cut events in the GFP gene, result in cells that remain GFP-positive. Cut events that are repaired by the Non-Homologous End-Joining (NHEJ) pathway often result in nucleotide insertion or deletion events (indels), resulting in frame-shift mutations in the coding sequence that cause loss of GFP gene expression and fluorescence. Cut events that are repaired by the Homology-Directed Repair (HDR) pathway, using the GFP to BFP HDR donor as a repair template, result in conversion of the cell fluorescence profile from that of GFP to that of BFP. An example of the GFP and BFP florescence before and after gene editing, measured by FACS, is shown in FIGS. 14A and 14B.

Example V: Thy1.2-Mediated Enrichment for Editing Cassette Uptake Using FACS

Cells with a stably integrated copy of the GFP gene (HEK293T-GFP) were co-nucleofected with a plasmid expressing MAD7 nuclease and a GFP-to-BFP editing cassette plasmid that also drives expression of the cell surface ligand Thy1.2. Thy 1.2 is a cell surface protein that is expressed on mouse thymocytes and not found on any human cells. Thy1.2 is thus a unique reporter for identifying human cells that have received the editing machinery necessary to provide Thy 1.2 expression.

Briefly, $2 \times 10^5$ cells were nucleofected with 200 ng of the MAD7 expression plasmid and 200 ng of the Thy1.2-expressing GFP-to-BFP editing cassette using program CM-130 on a 4D-Nucleofector X-unit (Lonza, Morristown, N.J.) in 20 µL nucleocuvettes.

Figure 15:
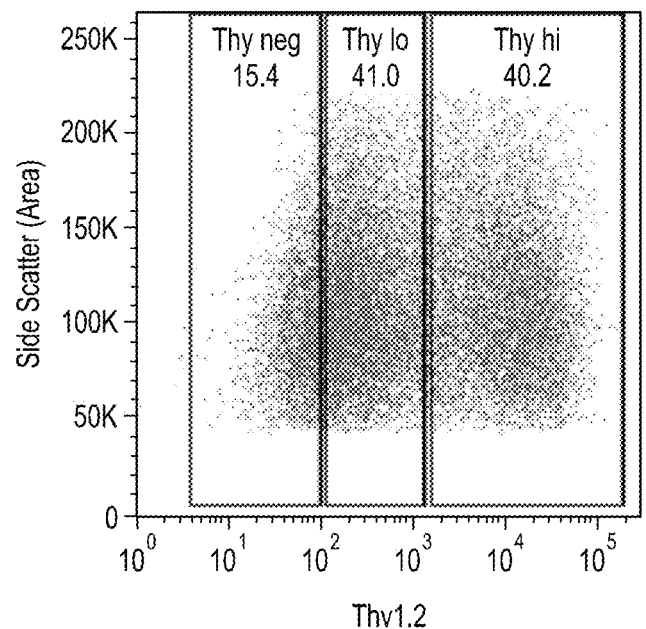
FIG. 15 is a plot showing differential expression levels of a Thy1.2 reporter expressed from a GFP to BFP editing cassette.
Figure 16A:
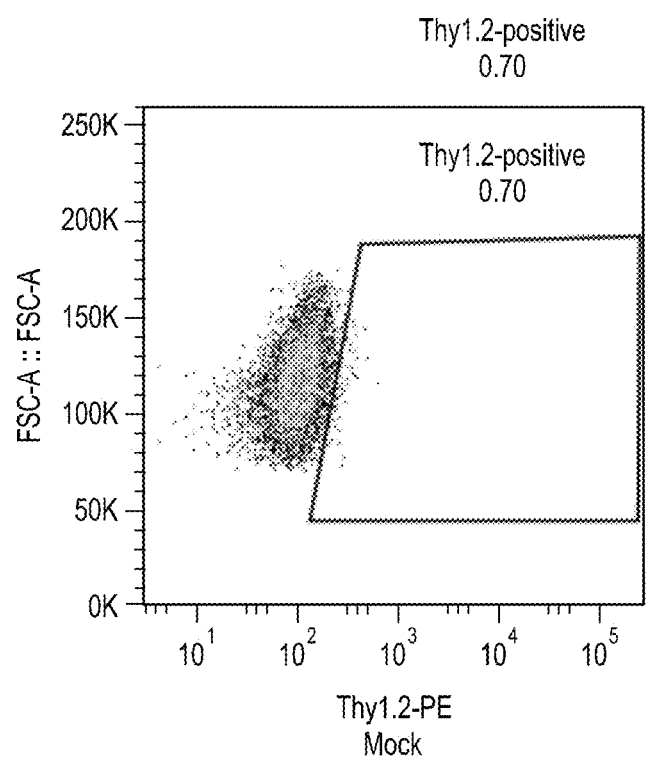
FIGS. 16A-16E are a series of plots showing the effects of the enrichment process on levels of Thy1.2$^{High}$ cells by MACS.
Figure 16B:
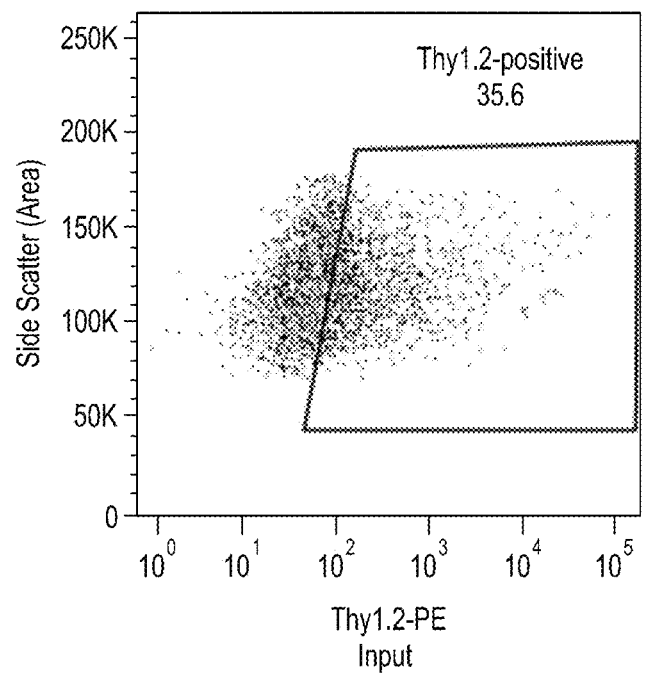
Figure 16C:
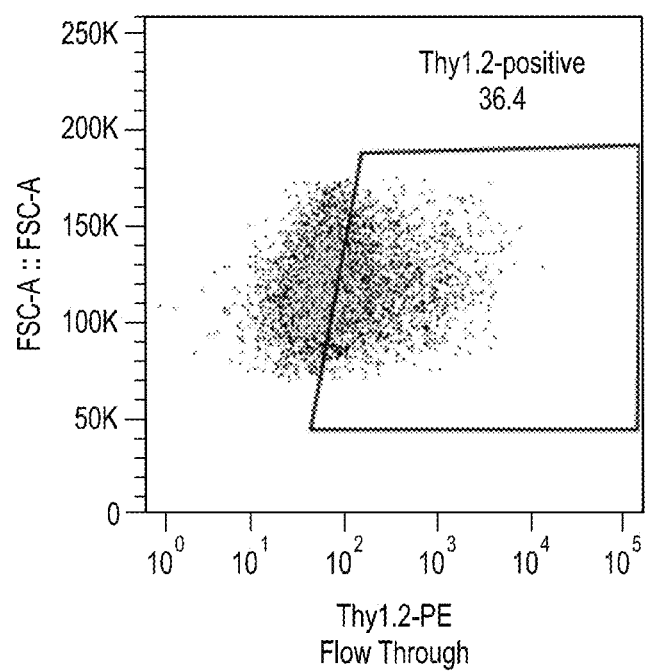
Figure 16D:
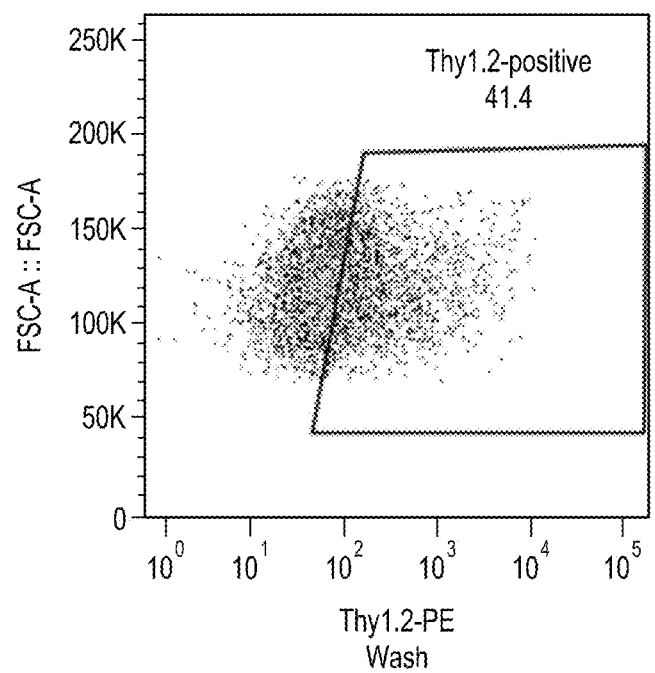
Figure 16E:
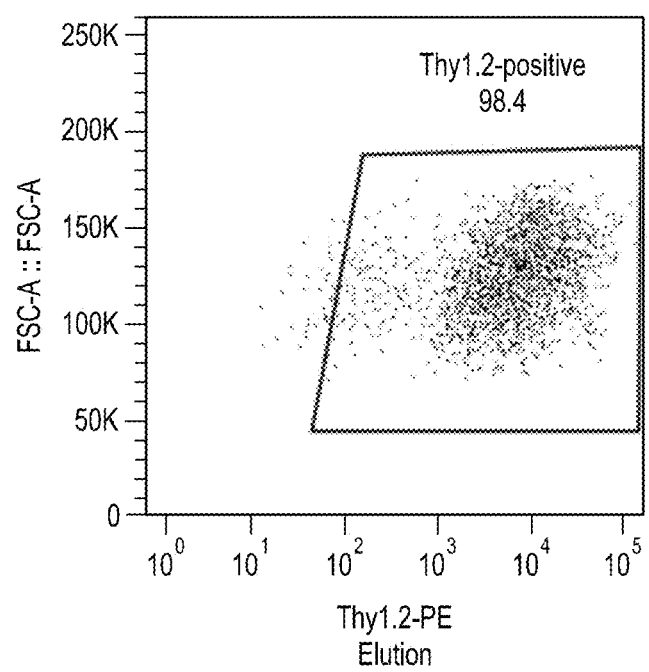

24 hours after nucleofection, cells were labeled with anti-Thy1.2 antibodies conjugated to the fluorophore phycoerythrin (PE). Antibody-labeled cells were then enriched using fluorescent-activated cell sorting (FACS) analysis on the FACS Melody (Becton Dickenson, Franklin Lakes, N.J.) to separate Thy1.2-negative cells from cells expressing low or high amounts of Thy1.2 (FIG. 15). The FACS-sorted subpopulations, as well as an unenriched control sample were plated in separate wells of a 24-well tissue culture dish and allowed to undergo gene-editing. The cells receiving a precise HDR-mediated two-base swap display a GFP-to-BFP conversion phenotype.

Figure 17:
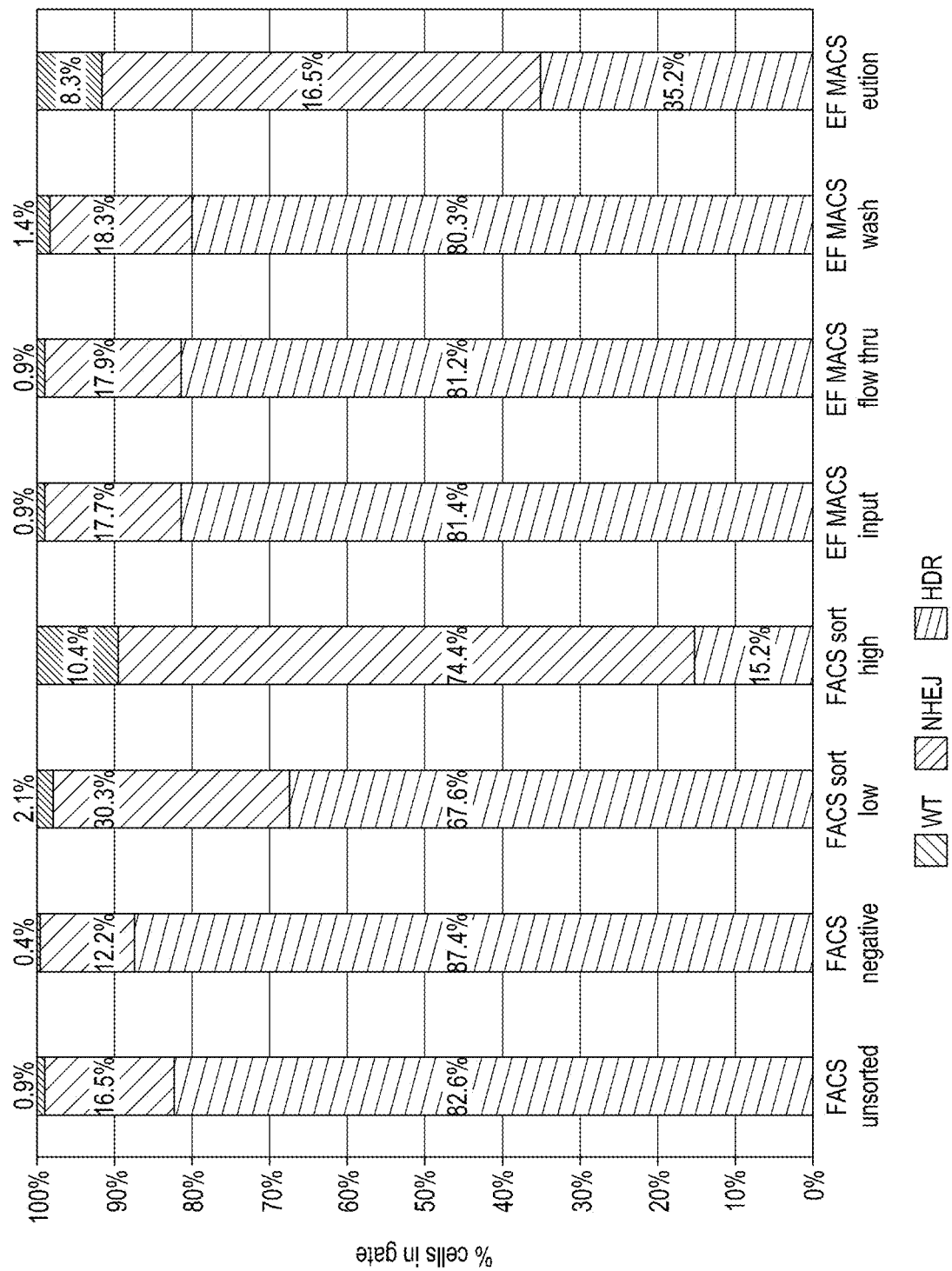
FIG. 17 is a bar graph showing comparable enrichment of cell populations with higher editing rates (NHEJ and HDR) by either FACS or MACS.

120 hours after transfection, subpopulations of cells enriched for Thy1.2 expression by FACS sorting were analyzed by FACS for levels of GFP or BFP expression. The percentage of cell counts in the GFP-positive (wild-type or no edit), GFP-negative (NHEJ-mediated insertion or deletion frameshift), or BFP-positive (HDR-mediated precise conversion of GFP to BFP sequence) quadrants of the FACS dot plot were quantified and compared across samples (FIG. 17). Unenriched populations were 83% GFP-positive (WT), 17% GFP and BFP-negative (NHEJ), and 1% BFP-positive (HDR). Cells that were enriched for editing cassette uptake and Thy1.2 expression by FACS were 15-68% GFP-positive (WT), 30-74% GFP and BFP-negative (NHEJ), and 2-10% BFP-positive (HDR), depending on whether the low-expressing or high-expressing population was specifically enriched.

Example VI: Thy1.2-Mediated Enrichment for Editing Cassette Uptake Using MACS

The enrichment methods as described above in Example V showed very similar efficiencies using magnetic-activated cell sorting (MACS) analysis. As above, cells with a stably integrated copy of the GFP gene (HEK293T-GFP) were co-nucleofected with a plasmid expressing MAD7 nuclease and a GFP-to-BFP editing cassette plasmid that also drives expression of the cell surface ligand Thy1.2. Briefly, $2 \times 10^5$ cells were nucleofected with 200 ng of the MAD7 expression plasmid and 200 ng of the Thy1.2-expressing GFP-to-BFP editing cassette using program CM-130 on a 4D-Nucleofector X-unit (Lonza, Morristown, N.J.) in 20 µL nucleocuvettes.

24 hours after nucleofection, cells were labeled with anti-Thy1.2 magnetic beads and purified on a MACS column according to the manufacturer's protocol (Miltenyi Biotec, Sunnyvale, Calif.). Samples of cells from the MACS column flow-through, column wash, and magnetic-purified elution fractions as well as a pre-enrichment control were labeled with anti-Thy1.2-PE fluorescent antibodies and analyzed for Thy1.2 expression levels by FACS. Under the conditions tested, the MACS purification specifically enriched the subpopulation of cells with the highest levels of Thy1.2 expression, as measured by Thy1.2-PE labeling (FIGS. 16A-16E). Cells from the flow-through, wash, and elution fractions from MACS purification, as well as an unenriched control were plated in separate wells of a 24 well tissue culture dish and allowed to undergo gene-editing and GFP-to-BFP conversion.

120 hours after transfection, subpopulations of cells enriched for Thy1.2 expression by MACS beads were further analyzed by FACS for levels of GFP or BFP expression. The percentage of cell counts in the GFP-positive (wild-type or no edit), GFP-negative (NHEJ-mediated insertion or deletion frameshift), or BFP-positive (HDR-mediated precise conversion of GFP to BFP sequence) quadrants of the FACS dot plot were quantified and compared across samples (FIG. 17). Unenriched populations were 80% GFP-positive (WT), 17% GFP and BFP-negative (NHEJ), and 1% BFP-positive (HDR). Cells that were enriched for editing cassette uptake and Thy1.2 expression by MACS were 15-35% GFP-positive (WT), 57-74% GFP and BFP-negative (NHEJ), and 8-10% BFP-positive (HDR).

The unique populations of cells with the highest level of Thy1.2 expression, whether enriched by FACS or MACS have significantly higher rates of overall editing as well has higher ratios of HDR to NHEJ. Additionally, the unedited GFP-positive population of cells has been drastically reduced. The methods described here in Examples IV and V enable the user to obtain a population of cells with a much higher proportion cells with intended edits and fewer unedited cells.

Example VII: ΔTetherin-HA-Mediated Enrichment for Editing Cassette Uptake Using FACS Cells with a stably integrated copy of the GFP gene (HEK293T-GFP) were co-nucleofected with a plasmid expressing MAD7 nuclease and a GFP-to-BFP editing cassette plasmid that also drives expression of the cell surface ligand Tetherin that has been engineered to contain an additional His-tag and a deletion rendering the protein non-functional. The ΔTetherin-HA used is a cell-surface surrogate handle that contains a deletion rendering the molecule non-functional.

Briefly, $2 \times 10^5$ cells were nucleofected with 200 ng of the MAD7 expression plasmid and 200 ng of the ΔTetherin-HA-expressing GFP-to-BFP editing cassette using program CM-130 on a 4D-Nucleofector X-unit (Lonza, Morristown, N.J.) in 20 µL nucleocuvettes.

24 hours after nucleofection, cells were labeled with anti-HA antibodies conjugated to the fluorophore phycoerythrin (PE). Antibody-labeled cells were then enriched using FACS Melody (Becton Dickenson, Franklin Lakes, N.J.) to separate ΔTetherin-HA-negative cells from cells expressing low or high amounts of ΔTetherin-HA. The FACS-sorted subpopulations, as well as an unenriched control sample were plated in separate wells of a 24-well tissue culture dish and allowed to undergo gene-editing. The cells receiving precise, HDR-mediated edits display a GFP-to-BFP conversion phenotype.

Figure 18:
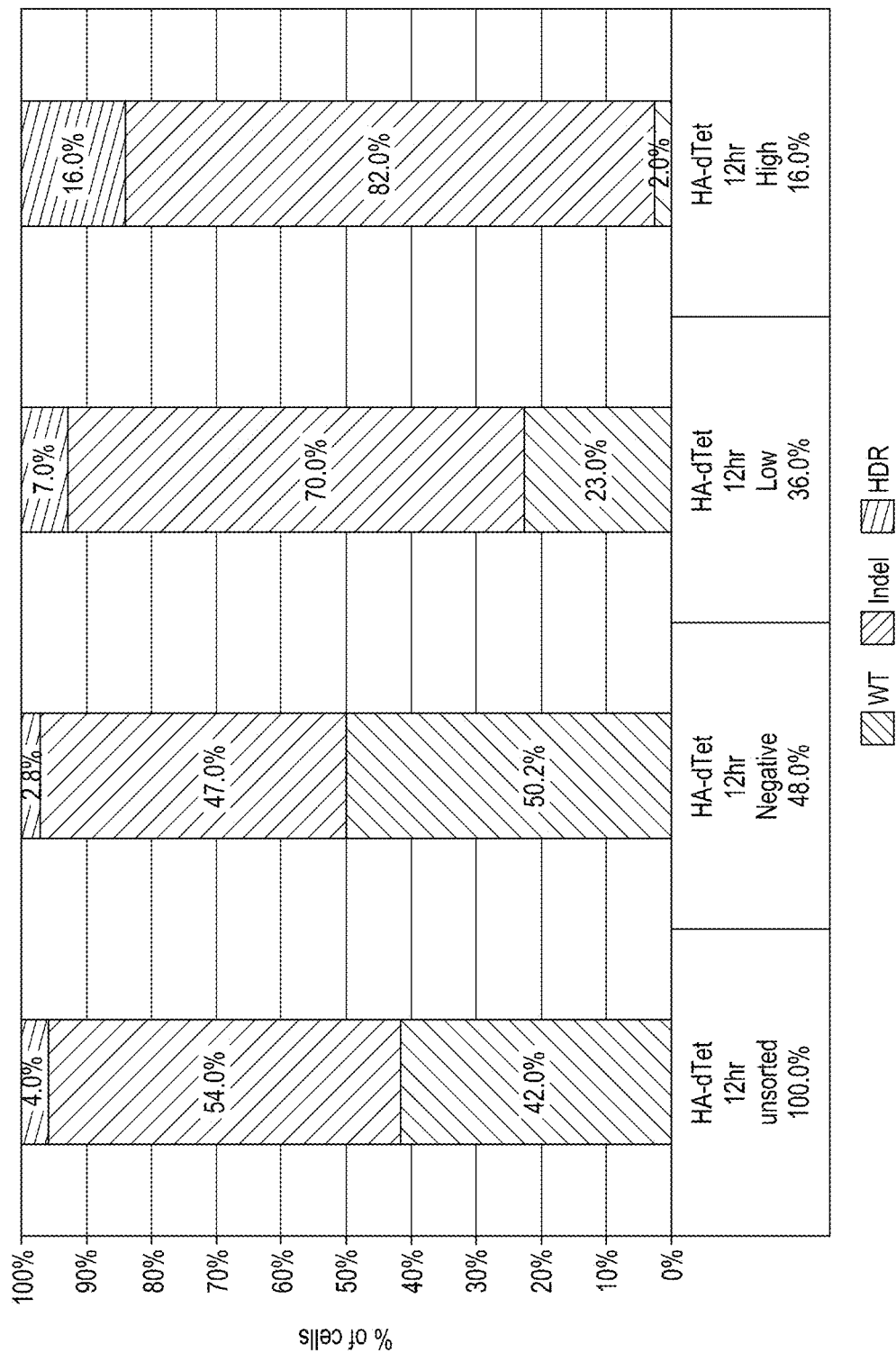
FIG. 18 is a bar graph showing ΔTetherin-HA Editing Cassette enriched editing demonstrated using FACS sorted cells.

120 hours after transfection, subpopulations of cells enriched for ΔTetherin-HA expression by either FACS sorting or MACS beads were analyzed by FACS for levels of GFP or BFP expression. The percentage of cell counts in the GFP-positive (wild-type or no edit), GFP-negative (NHEJ-mediated insertion or deletion frameshift), or BFP-positive (HDR-mediated precise conversion of GFP to BFP sequence) quadrants of the FACS dot plot were quantified and compared across samples (FIG. 18). Unenriched populations were 42% GFP-positive (WT), 54% GFP and BFP-negative (NHEJ), and 4% BFP-positive (HDR). Cells that were enriched for editing cassette uptake and ΔTetherin-HA expression by FACS or MACS were 2-23% GFP-positive (WT), 70-82% GFP and BFP-negative (NHEJ), and 7-16% BFP-positive (HDR) depending on whether the low-expressing or high-expressing population was specifically enriched. The unique populations of cells with the highest level of ΔTetherin-HA expression have significantly higher rates of overall editing as well has higher ratios of HDR to NHEJ. Additionally, the unedited GFP-positive population of cells has been drastically reduced. This method enables the user to obtain a population of cells with a much higher proportion cells with intended edits and fewer unedited cells.

Example VIII: Titration of Receptor-Specific Magnetic Beads to Enrich for Subpopulations of Cells with Higher Reporter Expression and Editing Rates Cells with a stably integrated copy of the GFP gene (HEK293T-GFP or HAP1-GFP) were co-nucleofected with a plasmid expressing MAD7 nuclease and a GFP-to-BFP editing cassette plasmid that also drives expression of the cell surface ligand ΔTetherin-HA or Thy1.2 Briefly, $2 \times 10^5$ cells were nucleofected with 200 ng of the MAD7 expression plasmid and 200 ng of the ΔTetherin-HA or Thy1.2-expressing GFP-to-BFP editing cassette using program CM-130 for HEK293T or DS-120 for HAP1-GFP on a 4D-Nucleofector X-unit (Lonza, Morristown, N.J.) in 20 µL nucleocuvettes.

Figures 19A, 19B:
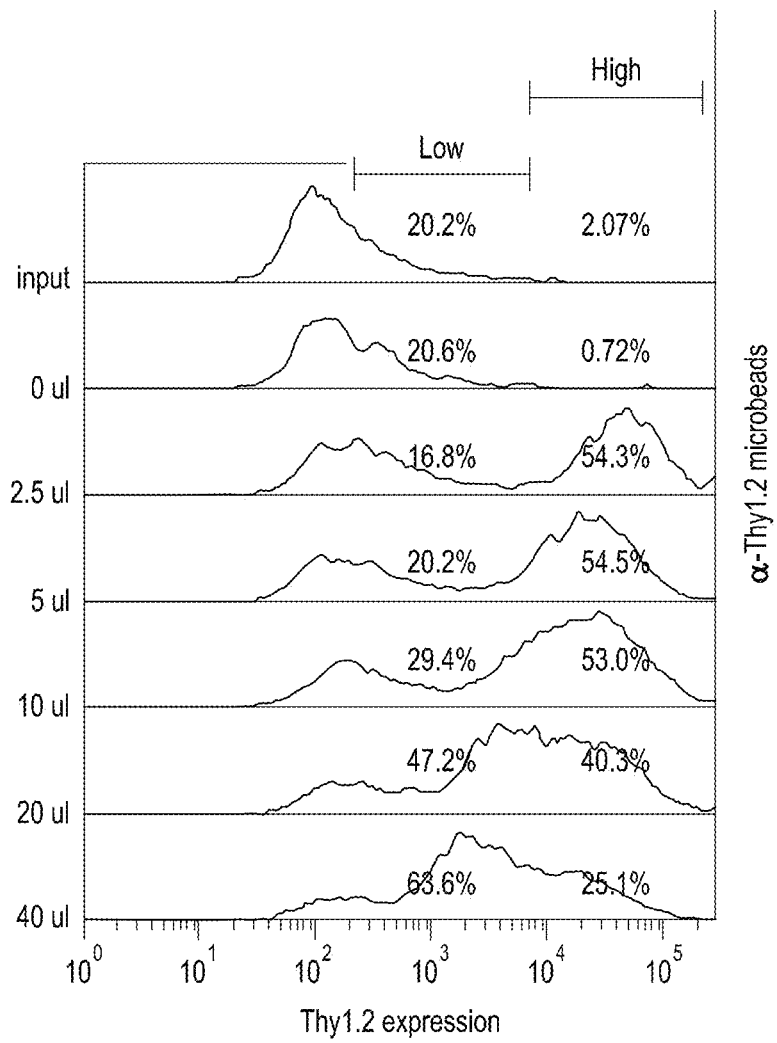
FIGS. 19A and 19B are a graph and table showing how MACS bead concentrations during enrichment affects the relative proportions of Thy1.2$^{High}$ and Thy1.2$^{Low}$ expressing cells isolated by enrichment.

24 hours after nucleofection, cells were labeled with increasing amounts of anti-Thy1.2 or anti-HA magnetic beads and purified on a magnetic-activated cell sorting (MACS) column according to the manufacturer's protocol (Miltenyi). As the amount of MACS beads was increased 9 µL of beads per 1000 total enrichment reaction volume), the relative amounts of purified cells with high and low receptor expression shifted. This was observed for enrichment of Thy1.2-expressing HEK293T-GFP cells (FIGS. 19A and 19B) and ΔTetherin-HA-expressing HAP1-GFP cells (FIGS. 20A and 20B).

Figure 21:
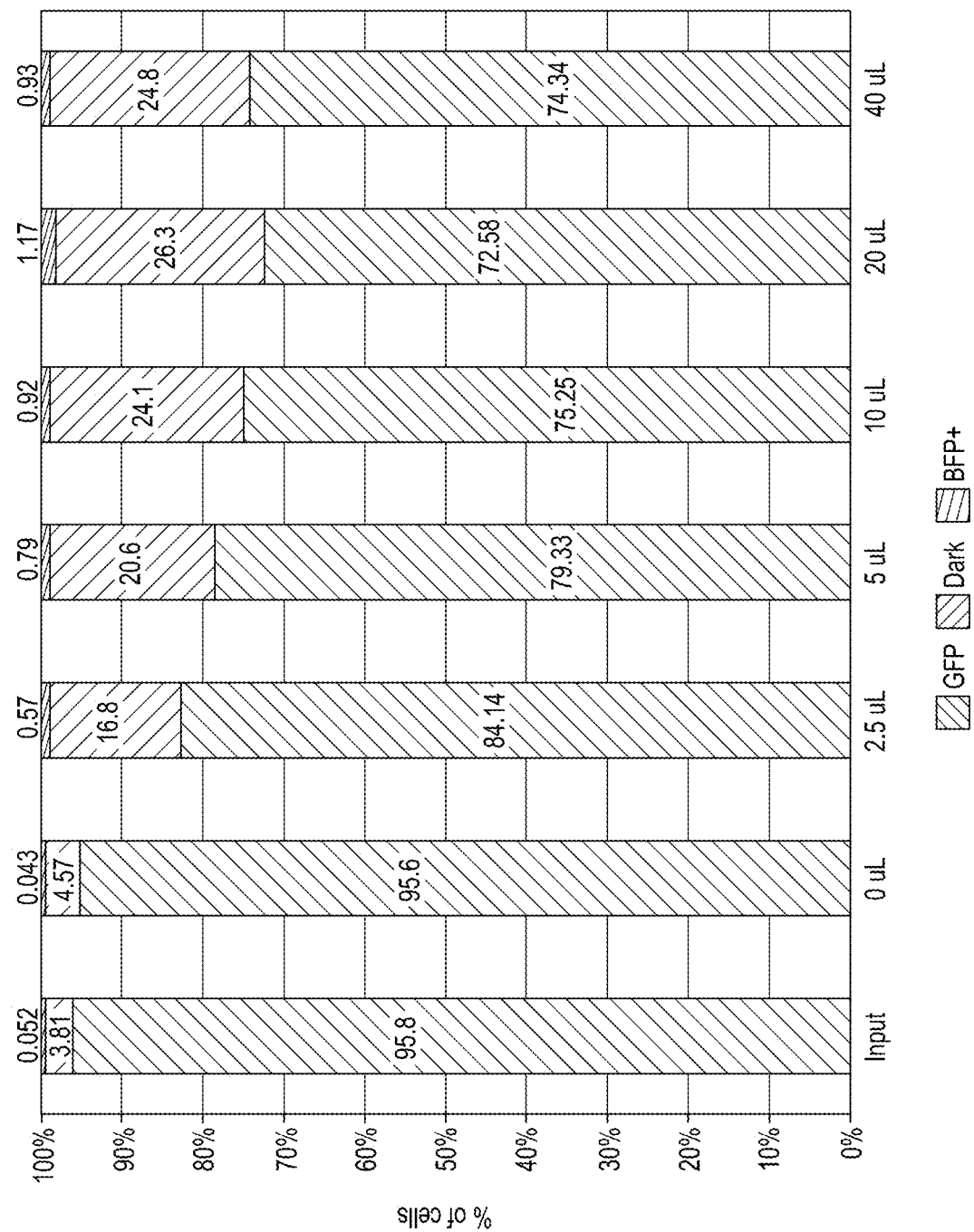
FIG. 21 is a bar graph showing edit rates for cells enriched using various amounts of Thy1.2-specific MACS beads.
Figure 22:
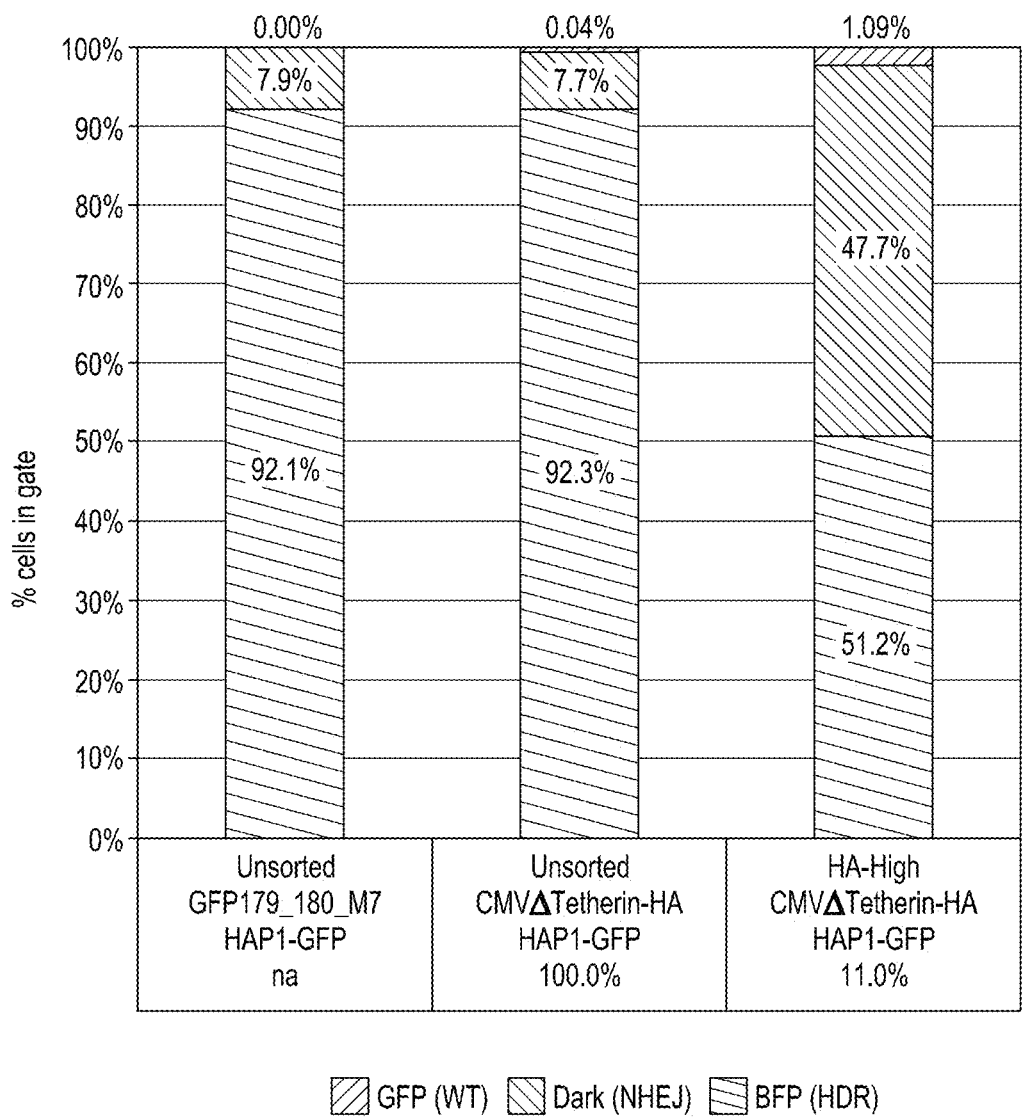
FIG. 22 is a bar graph showing analysis post enrichment for cells expressing high levels of the ΔTetherin-HA reporter in HAP1.

HEK293T-GFP cells enriched for editing machinery uptake using different amounts of Thy1.2-specific MACS beads were re-plated into 24 well tissue culture plates and allowed to undergo gene editing and GFP to BFP conversion. As the amount of beads was increased, the proportion of cells with imprecise edits (GFP- and BFP-negative) and precise edits (BFP-positive) increased accordingly (FIG. 21). We also used FACS to specifically enrich HAP1 cells expressing high levels of ΔTetherin-HA. Similar to the Thy1.2 reporter system, cells enriched for high levels of ΔTetherin-HA expression had relatively higher rates of NHEJ (48%) and HDR-mediated edits (1%) relative to unenriched controls, which exhibited 8% Indel and undetectable HDR (FIG. 22).

Example IX. Enrichment for HDR-Mediated Knock-in Edits

As above, cells with a stably integrated copy of the GFP gene (HEK293T-GFP) were co-nucleofected with one plasmid expressing MAD7 nuclease and an editing cassette that mediates a six base pair insertion into the DNMT3b gene and a second plasmid with a GFP-to-BFP editing cassette that also drives expression of the cell surface ligand Thy1.2.

Briefly, $2 \times 10^5$ cells were nucleofected with 200 ng of the MAD7 expression plasmid and 200 ng of the Thy1.2-expressing GFP-to-BFP editing cassette using program CM-130 on a 4D-Nucleofector X-unit (Lonza, Morristown, N.J.) in 20 µL nucleocuvettes.

24 hours after nucleofection, cells were labeled with anti-Thy1.2 magnetic beads and purified on a MACS column according to the manufacturer's protocol (Miltenyi Biotec, Sunnyvale, Calif.). Cells were also labeled with anti-Thy1.2-PE fluorescent antibodies and enriched for high-level Thy1.2 expression by FACS. Cells from the MACS or FACS enrichments or unenriched controls were plated in separate wells of a 24 well tissue culture dish and allowed to undergo gene-editing.

Figure 24:
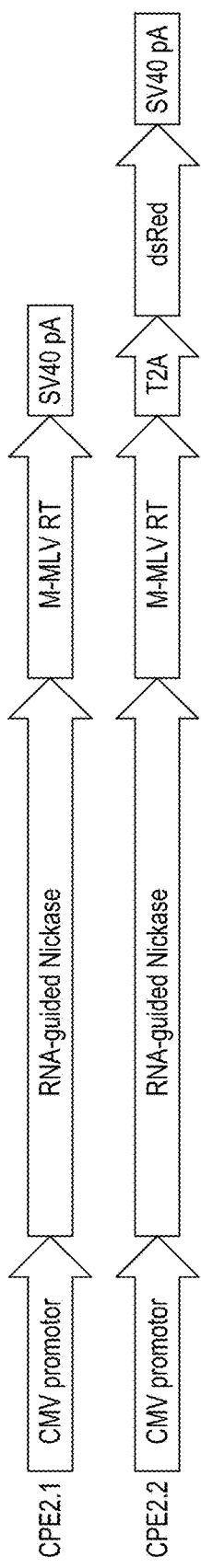
FIG. 24 shows the designs of the CFE editing constructs CFE2.1 and CFE 2.2.

120 hours after transfection, genomic DNA was purified from each subpopulation of enriched or unenriched cells using a Qiagen DNeasy blood and tissue kit (Velmo, Netherlands). First, a 613 base pair fragment of the DNMT3b gene was amplified by PCR with primers outside the region spanned by the 180 base pair homology arm regions on the editing cassette plasmid. A second PCR reaction was performed to amplify a 180 base pair region of DNMT3b gene containing the region targeted by the MAD7-gRNA complex and the 6 base insertion targeted by the HDR donor on the editing cassette. These PCR amplicons were prepared for NGS using an Illumina TruSeq DNA sample prep kit according to the manufacturer's directions. Samples were sequenced using an Illumina MiSeq using the 2×300 reagent kit (Illumina, San Diego, Calif.). NGS analysis was performed using a custom NGS analysis and sequencing read alignment pipeline to bin read counts according to sequence identity to DNMT3b (WT) DNMT3b with a complete or partial targeted 6 base insertion (HDR_complete or HDR_partial) or a DNMT3b sequence containing insertions or deletions (Indel or NHEJ). Cells that were enriched for editing cassette uptake by FACS had 9.8% complete intended HDR-mediated knock-in edits, 1.1% partial HDR edits, and 73.9% Indels (FIG. 24). Cells enriched for cassette uptake by MACS had insertions or deletions (Indel). Cells that were enriched for editing cassette uptake by MACS had 11.2% complete intended HDR-mediated knock-in edits, 1.3% partial HDR edits, and 78.4% Indels. In contrast, cells that did not undergo any enrichment exhibited 4.2% complete intended HDR-mediated knock-in edits, 0.5% partial HDR edits, and 51.8% Indels. (FIG. 24).

The unique populations of cells with the highest level of Thy1.2 uptake reporter expression, whether enriched by FACS or MACS have significantly higher rates of overall editing as well has higher ratios of HDR-mediated knock-in to NHEJ at the DNMT3b locus. Additionally, the unedited population of cells has been drastically reduced. (FIG. 24).

Example X: CREATE Fusion Editing

Figure 25:
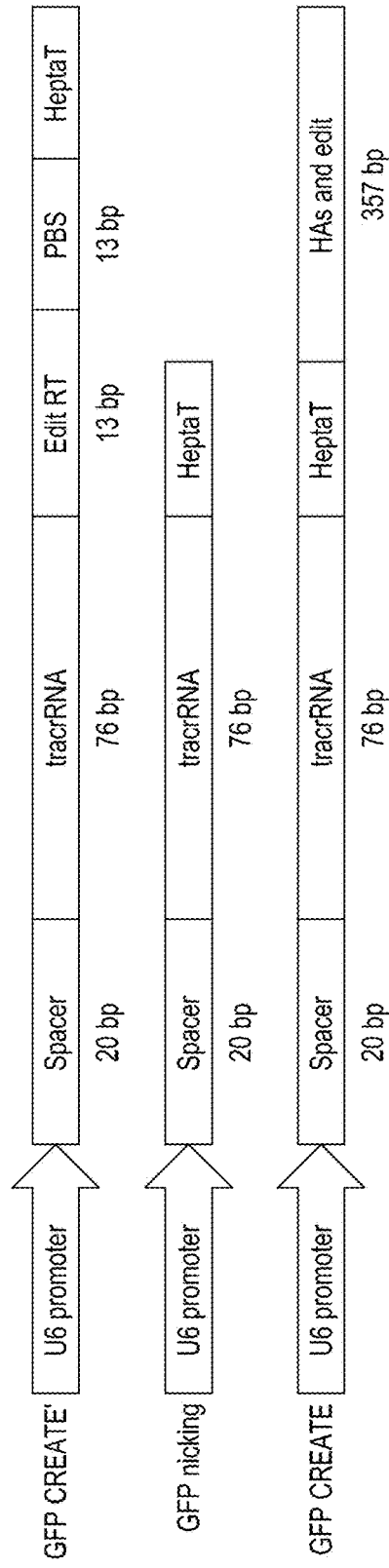
FIG. 25 shows the designs of various gRNAs that include the 13 bp TY-to-SH edit or a second region of 13 bp that is complementary to the nicked EGFP DNA sequence.

CREATE Fusion Editing is a novel technique that uses a nucleic acid nickase fusion protein having reverse transcriptase activity with a nucleic acid encoding a gRNA comprising a region complementary to a target region of a nucleic acid in one or more cells covalently linked to an editing cassette comprising a region homologous to the target region in the one or more cells with a mutation of at least one nucleotide relative to the target region in the one or more cells and a protospacer adjacent motif (PAM) mutation. To test the feasibility of CREATE Fusion Editing in HEK293T cells, two editing vectors were designed as shown in FIG. 25.

In a first design, a nickase enzyme derived from a Type II CRISPR enzyme was fused to an engineered reverse transcriptase (RT) on the C-terminus and cloned downstream of a CMV promoter. In this instance, the RT used was derived from Moloney Murine Leukemia Virus (M-MLV). This design was termed CREATE Fusion Editor 2.1 (CFE2.1) and allows for strong expression of nickase enzyme and M-MLV RT fusion protein. In CFE2.2, an enrichment handle (T2A-dsRed) was also added on the C-terminus of CFE2.1. The enrichment handle allowed selection of the cells that express the nickase enzyme and RT fusion protein.

Figure 26:
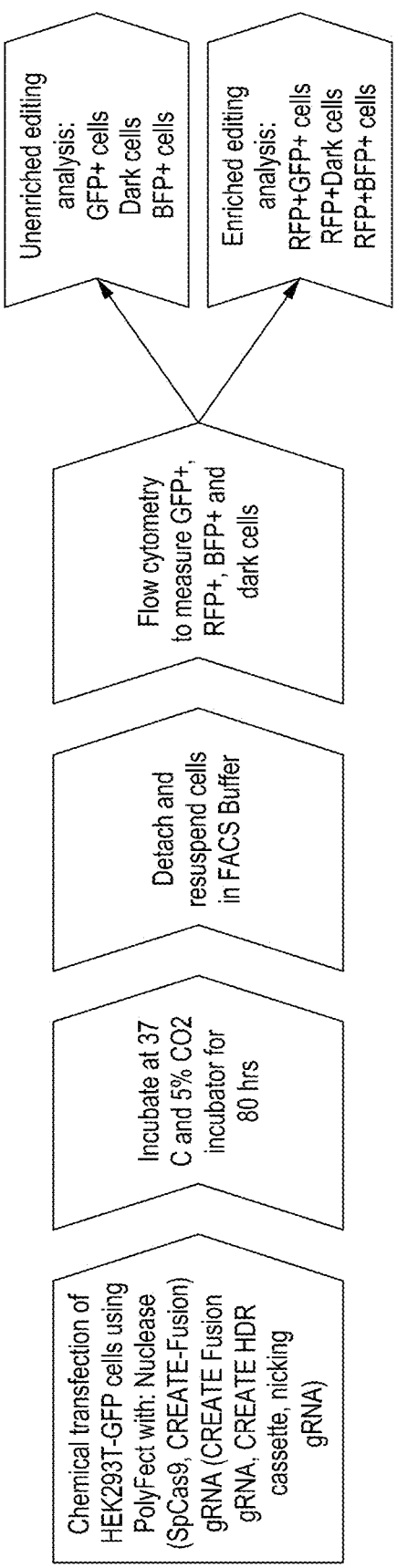
FIG. 26 is a diagram showing the basic protocol for editing using the CREATE Fusion Editing cassettes of FIG. 25 in comparison to direct nuclease editing.
Figure 27B:
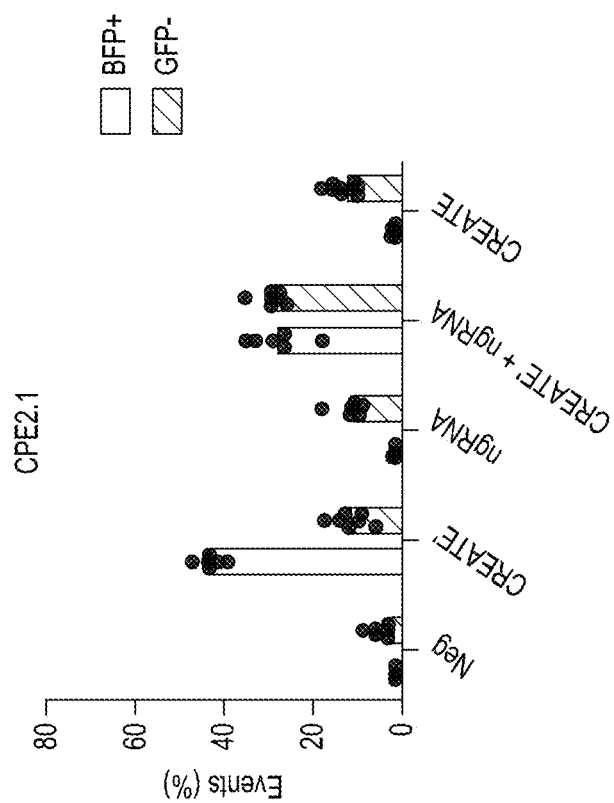
FIGS. 27A-27D are graphs showing the editing of GFP-to-BFP HEK293T cells using various protocols.
Figure 27A:
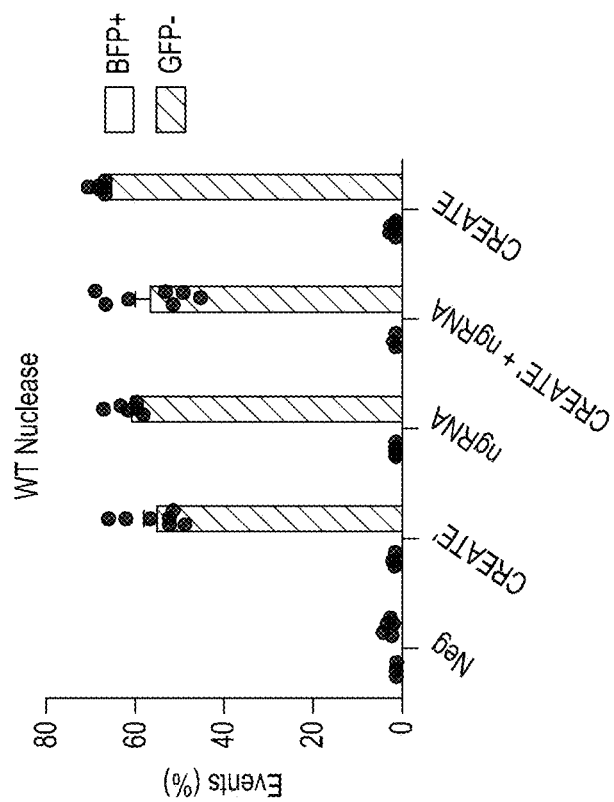
Figure 27D:
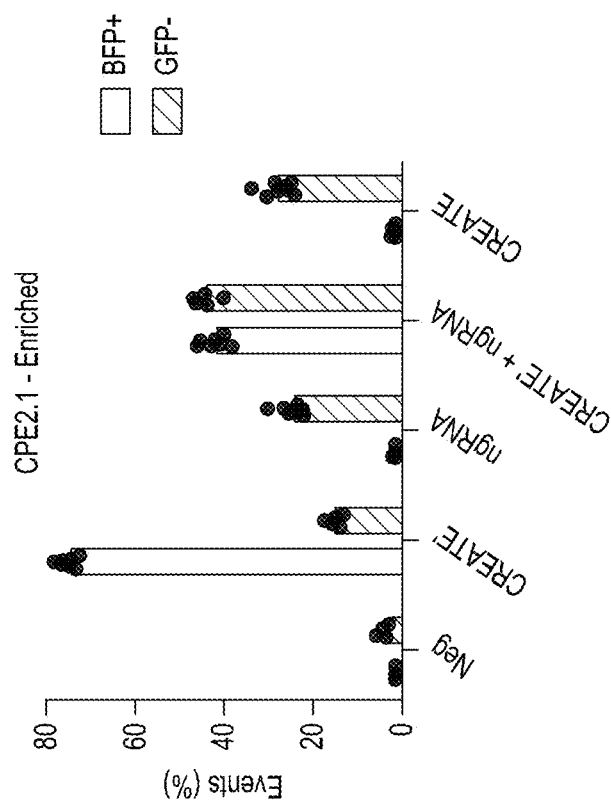
Figure 27C:
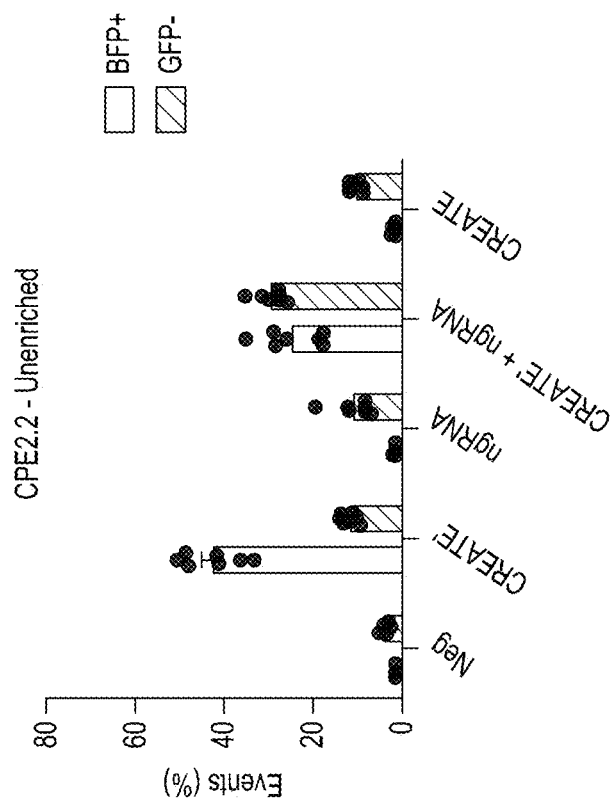
Figure 28:
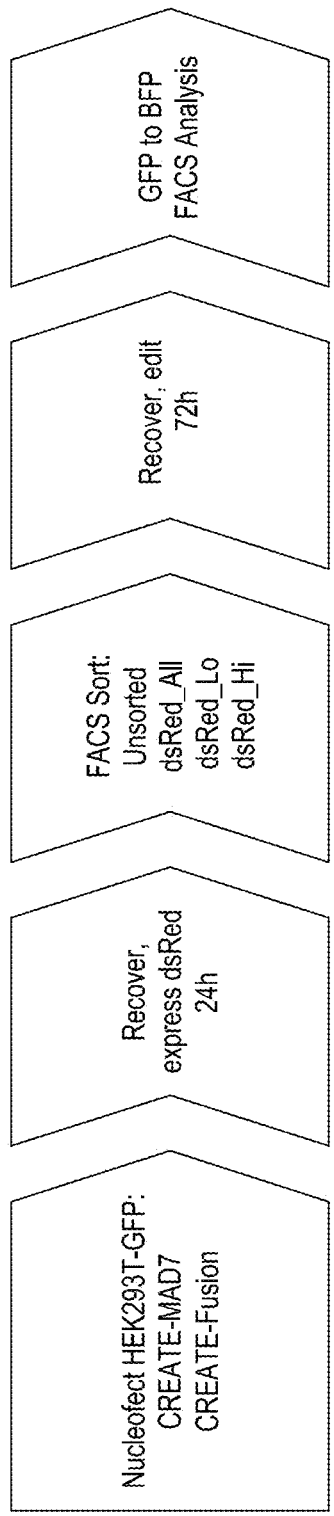
FIG. 28 is a diagram showing the basic protocol for CREATE Fusion Editing in conjunction with FACS selection.

RNA guides were designed that were complementary to a single region proximal to the EGFP-to-BFP editing site. The CREATE Fusion gRNA was extended on the 3' end to include a region of 13 bp that include the TY-to-SH edit and a second region of 13 bp that is complementary to the nicked EGFP DNA sequence (FIG. 26). This allows the nicked genomic DNA to anneal to the 3' end of the gRNA which can then be extended by the RT to incorporate the edit in the genome. The second gRNA targets a region in the EGFP DNA sequence that is 86 bp upstream of the edit site. This gRNA was designed such that it enables the nickase to cut the opposite strand relative to CREATE Fusion gRNA. Both of these gRNAs were cloned downstream of a U6 promoter. A poly T sequence was also included that terminates the transcription of the gRNA.

A flow chart of the exemplary experimental process carried out is shown in FIG. 27.

The plasmids were transformed into NEB Stable *E. coli* (Ipswich, N.Y.) and grown overnight in 25 mL LB cultures. The following day the plasmids were purified from *E. coli* using the Qiagen Midi Prep kit (Venlo, Netherlands). The purified plasmid was then RNase A (ThermoFisher, Waltham, Mass.) treated and re-purified using the DNA Clean and Concentrator kit (Zymo, Irvine, Calif.).

HEK293T cells were cultured in DMEM medium which was supplemented with 10% FBS and 1× Penicillin and Streptomycin. 100 ng of total DNA (50 ng of gRNA plasmid and 50 ng of CFE plasmids) was mixed with 1 μl of PolyFect (Qiagen, Venlo, Netherlands) in 25 μl of OptiMEM in a 96 well plate. The complex was incubated for 10 minutes and then 20,000 HEK293T cells resuspended in 100 μl of DMEM were added to the mixture. The resulting mixture was then incubated for 80 hours at 37 C and 5% $CO_2$.

The cells were harvested from flat bottom 96 well plates using TrypLE Express reagent (ThermoFisher, Waltham, Mass.) and transferred to v-bottom 96 well plate. The plate was then spun down at 500 g for 5 minutes. The TrypLE solution was then aspirated and the cell pellet was resuspended in FACS buffer (1×PBS, 1% FBS, 1 mM EDTA and 0.5% BSA). The GFP+, BFP+ and RFP+cells were then analyzed on the Attune NxT flow cytometer and the data was analyzed on FlowJo software.

The RFP+BFP+cells that were identified were indicative of the proportion of enriched cells that have undergone precise or imprecise editing process. BFP+ cells indicate cells that have undergone successful editing process and express BFP. The GFP-cells indicate cells that have been imprecisely edited, leading to disruption of the GFP open reading frame and loss of expression.

The CREATE Fusion Editing process utilized a gRNA covalently linked to a region of homology to the intended target site in the genome. In this exemplary experiment, the edit is immediately 3' of the gRNA, and 3' of the edit is a further region complementary to the nicked genome, although the intended edit could also be present further 5' within the region homologous to the nicked genome. A nickase RT fusion enzyme created a nick in the target site and the nicked DNA annealed to its complementary sequence on the 3' end of the gRNA. The RT then extended the DNA, thereby incorporating the intended edit directly in the genome.

The effectiveness of CREATE Fusion Editing in GFP+ HEK293T cells was then tested. In the assay system devised, a successful precise edit resulted in a BFP+ cell whereas an imprecisely edited cells turned the cell both BFP and GFP negative. As shown in FIGS. 28A-28D, CREATE Fusion gRNA in combination with CFE2.1 or CFE2.2 gives ~40-45% BFP+ cells indicating that almost half the cell population has undergone successful editing. The GFP-cells are ~10% of the population. The use of a second nicking gRNA, as described in Liu et al. (Nature, 2019 December; 576 (7785):149-157). did not increase the precision edit rate any further; in fact, it significantly increased the imprecisely edited, GFP-negative cell population and the editing rate was lower.

Previous literature has shown that double nicks on opposite strands (<90 bp away) do result in a double strand break which tend to be repaired via NHEJ resulting in imprecise insertions or deletions. Overall, the results indicated that CREATE Fusion Editing predominantly yielded precisely edited cells and the imprecisely edited cells proportion is much lower.

An enrichment handle, specifically a fluorescent reporter (RFP) linked to nuclease expression, (CFE2.2) was included in this experimentation as a proxy for cells receiving the editing machinery. When only the RFP-positive cells were analyzed (computational enrichment) after 3-4 cell divisions, up to 75% of the cells were BFP+ when tested with CREATE Fusion gRNA. This indicated uptake or expression-linked reporters can be used to enrich for a population of cells with higher rates of CREATE Fusion-mediated gene editing. In fact, the combined use of CREATE Fusion Editing and the described enrichment methods resulted in a significantly improved rate of intended edits.

Example XI: FACS Enrichment for CREATE-Fusion Mediated Precise Edits

Figure 29:
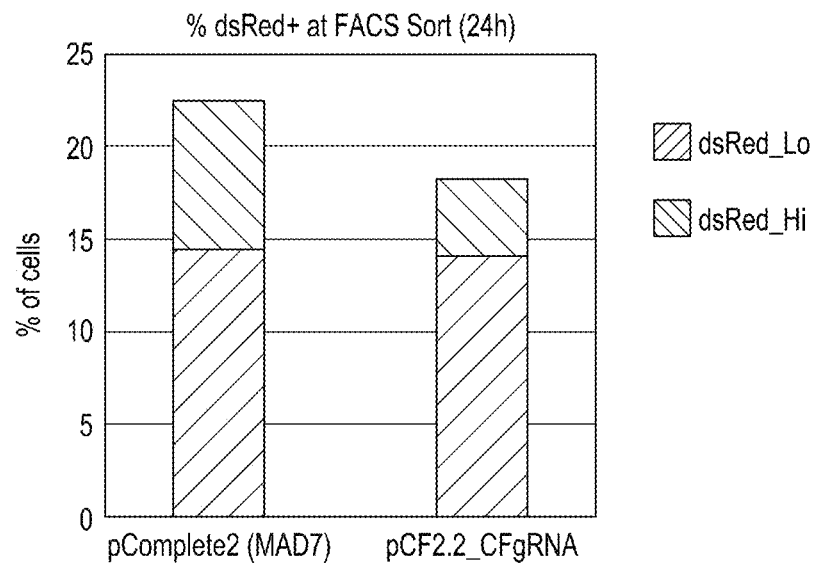
FIG. 29 is a graph showing the level of dsRed-Lo and dsRed-High cells resulting from editing with MAD7 nuclease editing versus CREATE Fusion Editing.

CREATE Fusion Editing was also carried out in mammalian cells in conjunction with physical selection using FACS. The basic protocol is set forth in FIG. 29.

Cells with a stably integrated copy of the GFP gene (HEK293T-GFP) were nucleofected with a plasmid expressing MAD7 nuclease and a GFP-to-BFP editing cassette plasmid that also drives expression of a fluorescent reporter molecule (dsRed) or a CREATE-Fusion enzyme plasmid with an RFP reporter (FIG. 25, CPE2.2) and a CREATE-Fusion gRNA expressing plasmid driving nick-based editing of GFP to BFP (FIG. 26, GFP CREATE'). Briefly, 1×10$^6$ cells were nucleofected with 4 ug of the MAD7 GFP to BFP editing plasmid or 2 ug the CREATE-Fusion enzyme plasmid and 2 ug of the CREATE-Fusion gRNA plasmid using program CM-130 on a 4D-Nucleofector X-unit (Lonza, Morristown, N.J.) in 100 μL nucleocuvettes.

Figure 30:
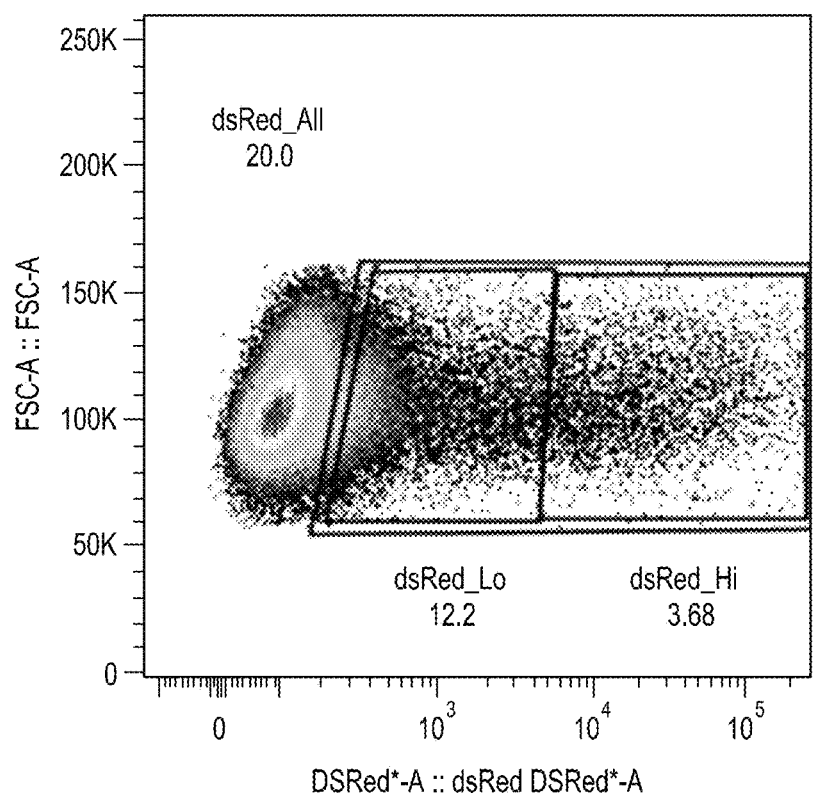
FIG. 30 is a plot showing the differential expression levels of dsRed in the edited cell populations.
Figure 31:
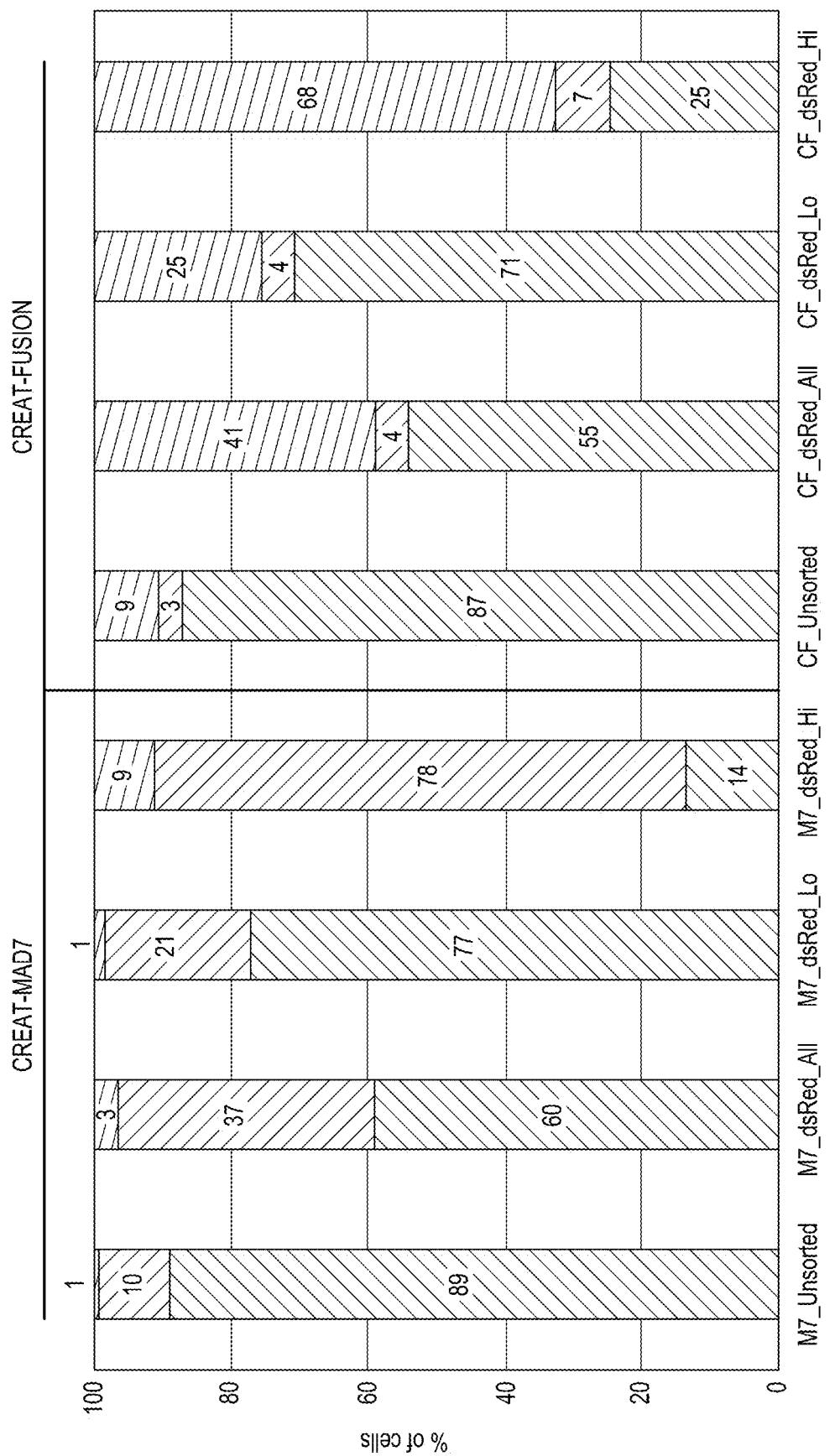
FIG. 31 is a bar graph showing dsRed editing for MAD7 or CREATE Fusion Editing using GFP to BFP time course of FACS sorted cells.

24 hours after nucleofection, cells were detached and for fluorescence-based sorting using a FACS Melody (Becton Dickenson, Franklin Lakes, N.J.) cells based on their dsRed reporter expression levels. Cells nucleofected with either the MAD7-based editing machinery or CREATE Fusion Editing machinery were transfected with similar efficiency as reported by percent dsRed-positive cells at 24 h post-transfection (FIG. 30). Cells were sorted into three populations, dsRed_all, dsRed_Lo, or dsRed_Hi using electronic gating based on dsRed fluorescence intensity (FIG. 31). The FACS-sorted subpopulations, as well as an unenriched control sample were plated in separate wells of a 24-well tissue culture dish and allowed to undergo gene-editing. The cells receiving a knock-in edit display a GFP-to-BFP conversion phenotype.

Figure 32:
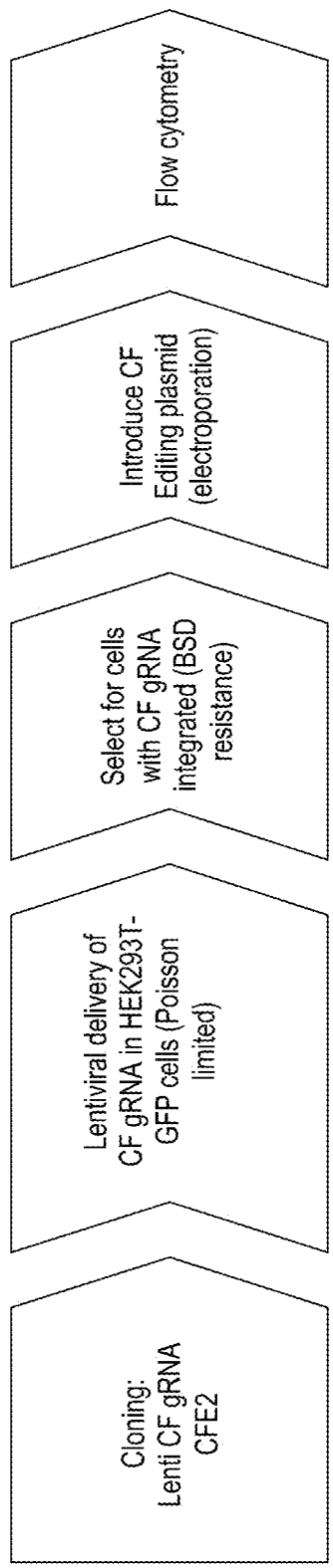
FIG. 32 is a diagram showing the basic protocol for CREATE Fusion Editing using a single gRNA.
Figure 33B:
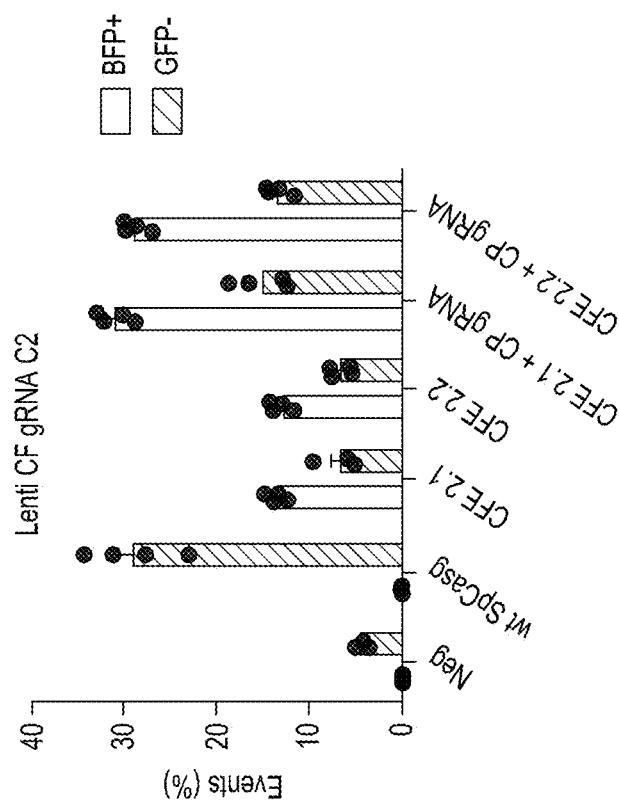
FIGS. 33A-33C are bar graphs showing the editing efficiencies of using the CREATE Fusion constructs CFE2.1 and CFE2.2 with Lentiviral delivery.
Figure 33A:
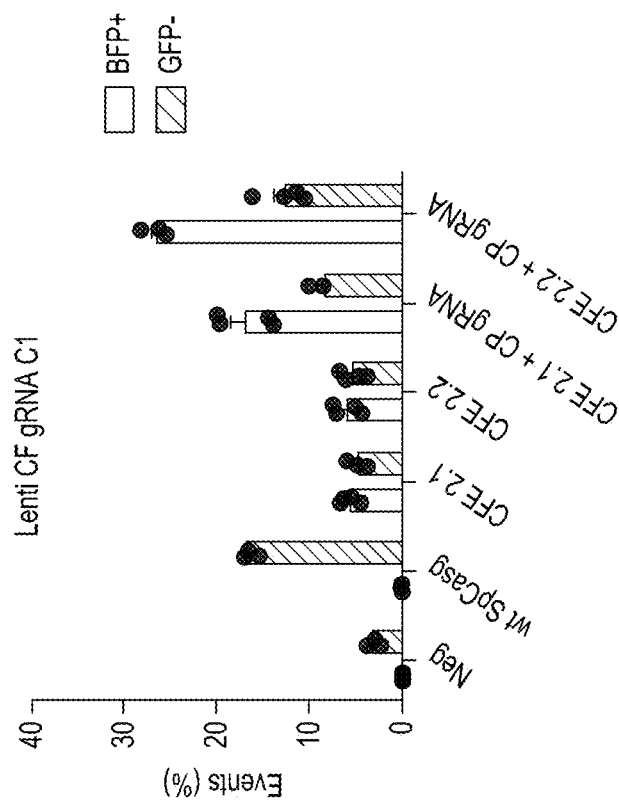
Figure 33C:
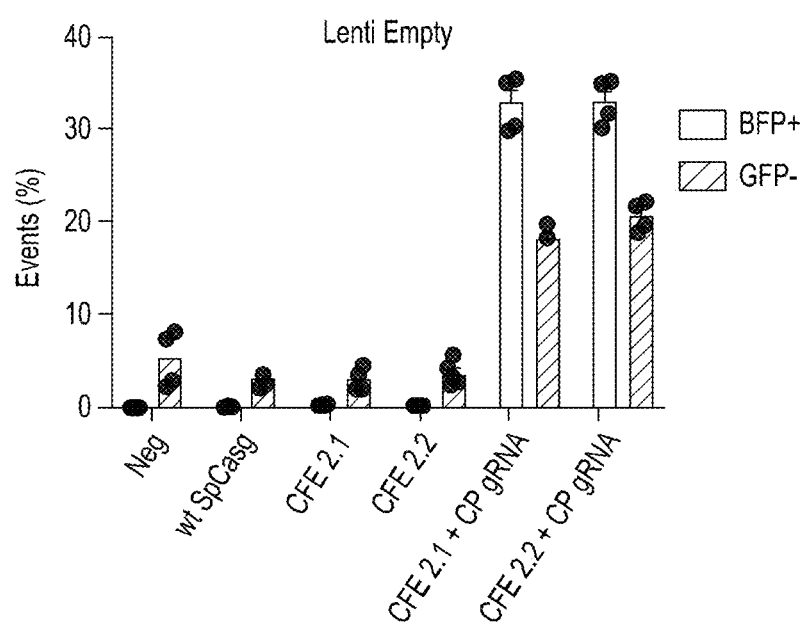

120 hours after nucleofection, subpopulations of cells enriched for dsRed expression by FACS sorting, which was indicative of enrichment for the presence of CREATE Fusion Editing machinery, were analyzed by FACS for levels of GFP or BFP expression. The percentage of cell counts in the GFP-positive (wild-type or no edit), GFP-negative (NHEJ-mediated insertion or deletion frameshift), or BFP-positive (HDR-mediated precise conversion of GFP to BFP sequence) quadrants of the FACS dot plot were quantified and compared across samples (FIG. 32). For MAD7-based editing, unenriched populations were 89% GFP-positive (WT), 10% GFP and BFP-negative (NHEJ), and 1% BFP-positive (HDR). Cells that were enriched for MAD7-linked dsRed expression were 14-16% GFP-positive (WT), 21-78% GFP and BFP-negative (NHEJ), and 3-9% BFP-positive (HDR), depending on the dsRed subpopulation selected for sorting (dsRed_All, dsRed-Lo, or dsRed_Hi). For CREATE-Fusion-based editing, unenriched populations were 87% GFP-positive (WT), 3% GFP and BFP-negative (NHEJ), and 9% BFP-positive (HDR). Cells that were enriched for MAD7-linked dsRed expression were 25-55% GFP-positive (WT), 4-7% GFP and BFP-negative (NHEJ), and 25-68% BFP-positive (HDR), depending on the dsRed subpopulation selected for sorting (dsRed_All, dsRed-Lo, or dsRed_Hi). These results demonstrate that enrichment for editing machinery uptake can yield a population of cells with higher proportions of cells with precise edits for both MAD7-CREATE and CREATE-Fusion editing systems.

Example XII: CREATE Fusion Editing with Single gRNA

CREATE Fusion Editing was carried out in mammalian cells using a single guide RNA covalently linked to a homology arm having an intended edit to the native sequence and an edit that disrupts nuclease cleavage at this site. The basic protocol is set forth in FIG. 32.

Figure 23:
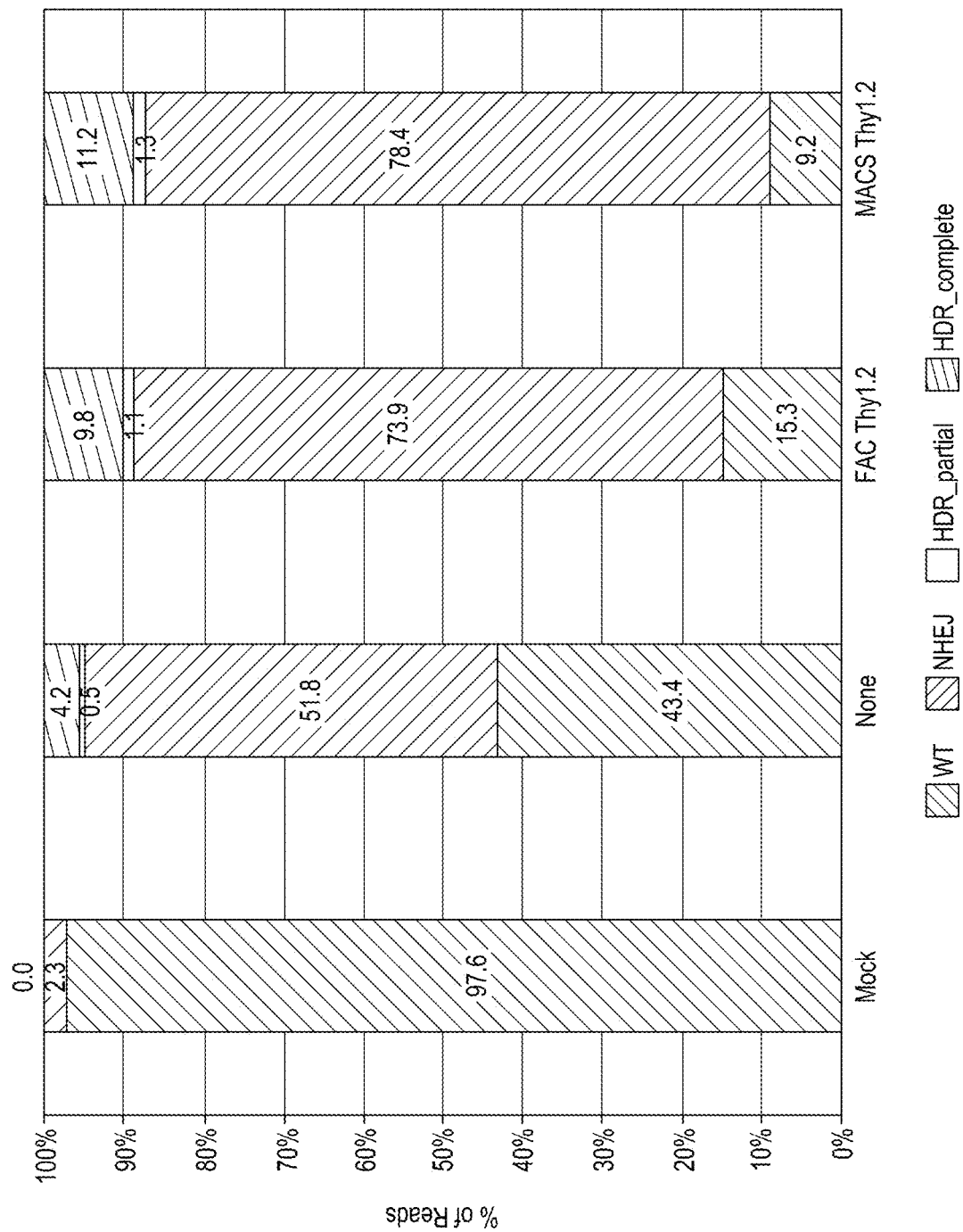
FIG. 23 is a bar graph showing enrichment of cells with higher knock-in editing rates at the DNMT3b gene using FACS enrichment techniques.

Briefly, lentiviral vectors were produced using the following protocol: 1000 ng of Lentiviral transfer plasmid containing the CREATE Fusion cassettes (FIGS. 23 and 24) along with 1500 ng of Lentiviral Packaging plasmids (ViraSafe Lentivirus Packaging System Cell BioLabs) were transfected into HEK293T cells using Lipofectamine LTX in 6-well plates. Media containing the lentivirus was collected 72 hrs post transfection. Two clones of a lentiviral CREATE Fusion gRNA-HA design were chosen, and an empty lentiviral backbone was included as negative control.

The day before the transduction, 200,000 HEK293T cells were seeded in six well plates. Different volumes of CREATE' lentivirus (10 to 1000 µl) was added to HEK293T cells in six well plates along with 10 µg/ml of Polybrene. 48 hours after transduction, media with 15 µg/ml of Blasticidin was added to the wells. Cells were maintained in selection for one week. Following selection, the well with lowest number of surviving cells was selected for future experiments (<5% cells)

The constructs CFE2.1, CFE2.2 (as shown in FIG. 25) or wild-type SpCas9 were electroporated into HEK293T cells using the Neon Transfection System (Thermo Fisher Scientific, Waltham, Mass.). Briefly, 400 ng of total plasmid DNA was mixed with 100,000 cells in Buffer R in a total of 150 volume. The 10 µl Neon tip was used to electroporate cells using 2 pulses of 20 ms and 1150 v. Cells were analyzed on the flow cytometer 80 hrs post electroporation.

Figure 34B:
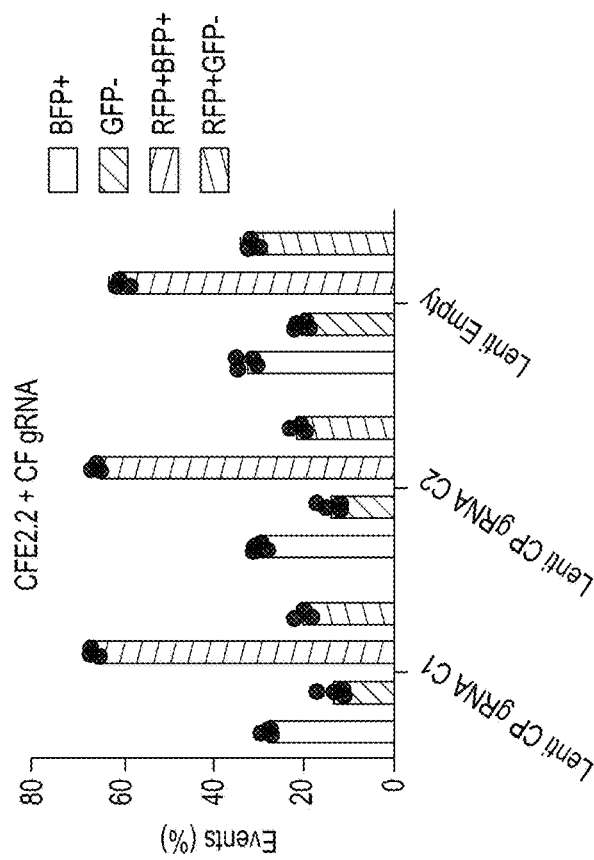
FIGS. 34A and 34B are bar graphs comparing the editing efficiencies of using the CREATE Fusion construct CFE2.2 versus MAD7 editing, both with lentiviral delivery.
Figure 34A:
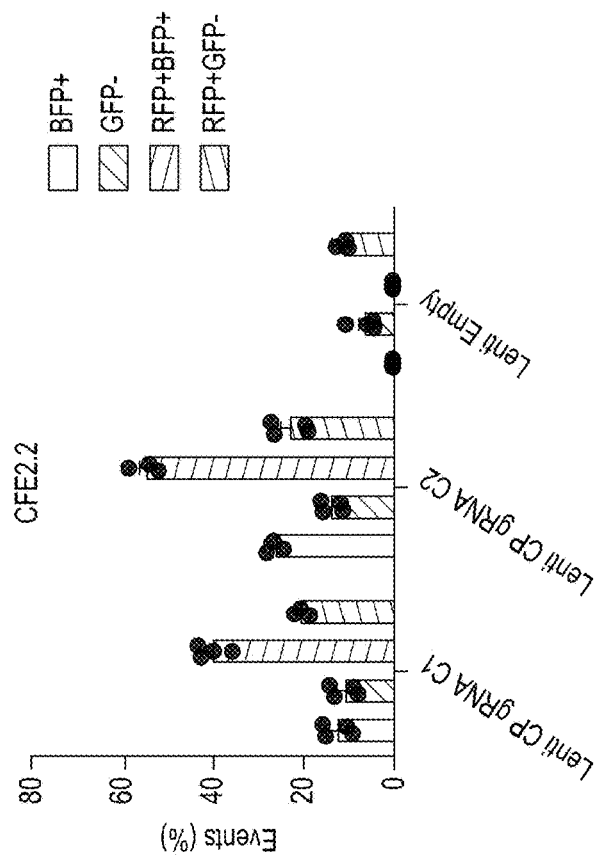

As shown in FIGS. 34A and 34B, unenriched editing rates of up to 15% were achieved from single copy delivery of gRNA When the editing was combined with computational selection of RFP+ cells, however, Enriched editing rates of up to 30% were achieved from a single copy delivery gRNA. This enrichment via selection of cells receiving the editing machinery was shown to result in a 2-fold increase in precise, complete intended edits (FIG. 35) Two or more enrichment/delivery steps can also be used to achieve higher editing rates of CREATE Fusion Editing in an automated instrument, e.g., use of a module for cell handle enrichment and identification of cells having BFP expression. When the method enriched for cells that have higher gRNA expression levels, the editing rate was even further increased, and thus a growth and/or enrichment module of the instrument may include gRNA enrichment.

Example XIII: Trackable CREATE Fusion Editing Dual Cassette Architecture

Combining the enhanced editing efficiency and decreased toxicity of the CREATE fusion system with a tracking or recording technology provides a novel way to implement tracking of large genomic libraries using CREATE fusion editing as carried out in massively parallel or combinatorial formats. Examples of such recording technologies useful with the methods of the present disclosure include those described in U.S. Pat. No. 10,017,760, 10,294,473 and 10,287,575, which are each incorporated by reference herein for all purposes.

Figure 35A:
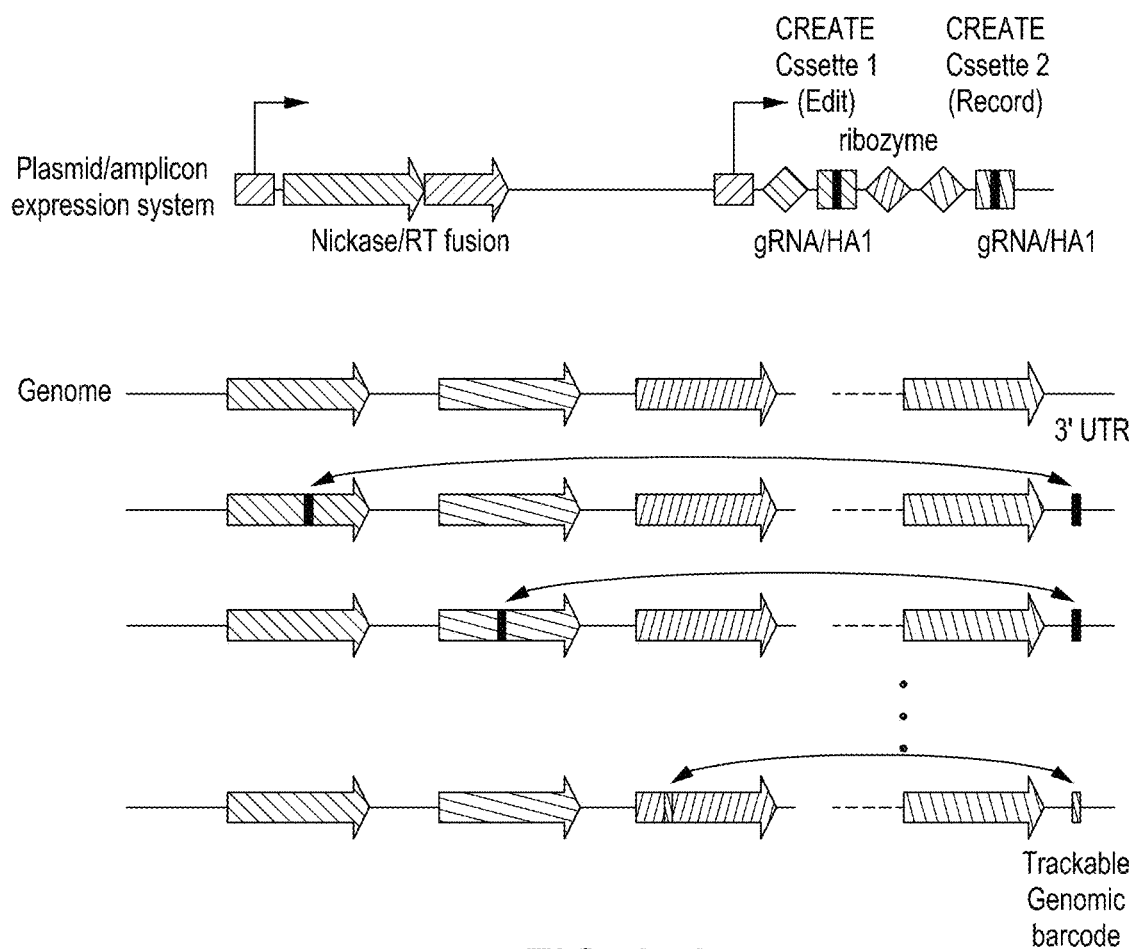
FIGS. 35A and 35B are figures showing exemplary strategies for using a CREATE fusion editing system with a tracking or recording technology.
Figure 35B:
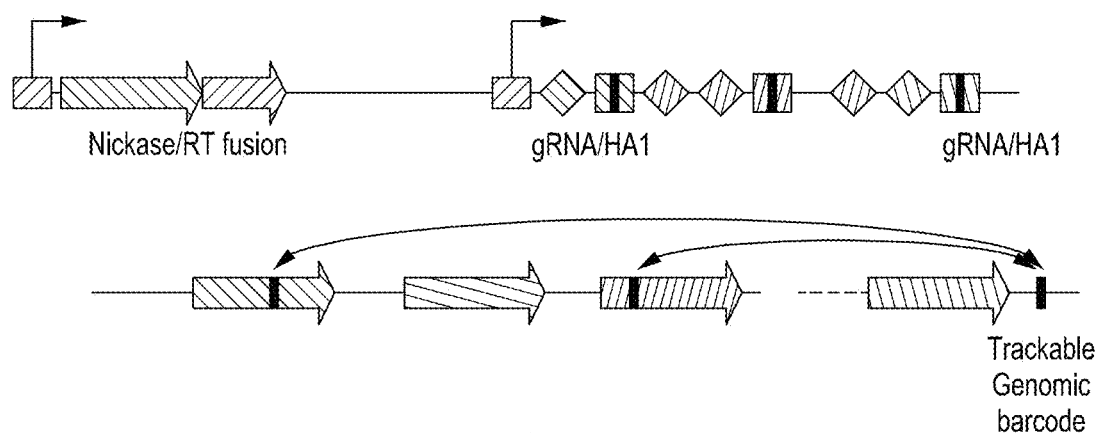

A simple example of how this can be implemented is shown in FIGS. 35A and 35B. A CREATE fusion enzyme comprising the nickase and RT activities is encoded on the same plasmid or amplicon as a dual CREATE cassette fusion system (FIG. 35A). CREATE cassette 1 encodes the gRNA-HA targeting sequences that once transcribed into RNA are necessary to guide nick-translation based editing at a functional site of interest in the chromosome. CREATE cassette 2 encodes a second gRNA-HA set that targets an inert secondary site, for example the 3' UTR of a pseudogene as one possible location to integrate a DNA barcode that is unique for each target site variant.

In this exemplary embodiment, the covalent coupling of the gRNA-HA elements within each editing cassette function to colocalize the RNA for efficient reverse transcription at each nick site to drive the editing process at each locus. Meanwhile the covalent coupling between cassettes ensures the two edits are highly correlated at the single cell level. The unique identity of the barcode sequence encoded in CREATE cassette 2, once integrated, thus serves as a trackable genomic barcode that can report the identity of edits across the genome based on sequencing or other molecular readouts of a fixed chromosomal position. This barcoding approach reduces the complexity of downstream population sequencing to simple PCR amplicon sequencing assays.

As an additional example this recording logic can be further expanded to cover combinatorial edits within a single cell by the inclusion of additional CREATE cassettes (FIG. 35B). Here the recording site and unique barcode are maintained, but the editing sites encompass ≥2 targets within the same cell. In this case the barcode now provides a report of combinatorial editing events on a single cell level and allows fitness tracking and computational de-convolution of combinatorial edited cell populations using the trackable barcode feature.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. An automated multi-module cell editing instrument comprising:
   a housing configured to house all of some of the modules;
   a receptacle configured to receive cells;
   one or more receptacles configured to receive nucleic acids and/or proteins, wherein the nucleic acids and/or proteins comprise editing machinery;
   an editing machinery introduction module configured to introduce the nucleic acids and/or proteins into the cells;
   an editing module configured to allow the introduced nucleic acids to edit nucleic acids in the cells;
   an enrichment module to enrich for cells receiving the editing machinery;
   a processor configured to operate the automated multi-module cell editing instrument based on user input and/or selection of a pre-programmed script; and
   an automated liquid handling system to move cells from the receptacle configured to receive cells to the editing machinery introduction module, from the editing machinery introduction module to the editing module, and from the editing module to the enrichment module; and to move nucleic acids and/or proteins to the editing machinery introduction module, all without user intervention.

2. The automated multi-module cell editing instrument of claim 1, wherein the nucleic acids in the one or more receptacles comprise a backbone and an editing cassette, the automated multi-module cell editing instrument further comprises a nucleic acid assembly module.

3. The automated multi-module cell editing instrument of claim 1, wherein the enrichment module uses FACS to enrich for cells receiving the editing machinery.

4. The automated multi-module cell editing instrument of claim 1, wherein the enrichment module uses MACS to enrich for cells receiving the editing machinery.

5. The automated multi-module cell editing instrument of claim 1, wherein the editing module further comprises a recovery module following introduction of the editing machinery.

6. The automated multi-module cell editing instrument of claim 1, further comprising a growth module configured to grow the cells.

7. The automated multi-module cell editing instrument of claim 6, wherein the growth module measures optical density of the growing cells.

8. The automated multi-module cell editing instrument of claim 7, wherein optical density is measured continuously.

9. The automated multi-module cell editing instrument of claim 6, wherein the processor is configured to adjust growth conditions in the growth module such that the cells reach a target optical density at a time requested by a user.

10. The automated multi-module cell editing instrument of claim 1, wherein the receptacle configured to receive cells and the one or more receptacles configured to receive nucleic acids are contained within a reagent cartridge.

11. The automated multi-module cell editing instrument of claim 10, wherein some or all reagents required for cell editing are contained within the reagent cartridge.

12. The automated multi-module cell editing instrument of claim 11, wherein the reagents contained within the reagent cartridge are locatable by a script read by the processor.

13. The automated multi-module cell editing instrument of claim 12, wherein the reagent cartridge includes reagents and is provided in a kit.

14. The automated multi-module cell editing instrument of claim 1, wherein the editing machinery introduction module comprises an electroporation device.

15. The automated multi-module cell editing instrument of claim 14, wherein the electroporation device is a flow-through electroporation device.

16. The automated multi-module cell editing instrument of claim 1, further comprising a filtration module configured to concentrate the cells and render the cells electrocompetent.

17. An automated multi-module cell editing instrument comprising:
   a housing configured to house all of some of the modules;
   a receptacle configured to receive cells, nucleic acids and/or proteins, wherein the nucleic acids and/or proteins comprise editing machinery;
   an editing machinery introduction module configured to introduce the nucleic acids and/or proteins into the cells;
   an editing module configured to allow the introduced nucleic acids and/or proteins to edit nucleic acids in the cells;
   an enrichment module to enrich for cells receiving the editing machinery;
   a processor configured to operate the automated multi-module cell editing instrument based on user input and/or selection of a pre-programmed script; and
   an automated liquid handling system to move cells from the receptacle configured to receive cells to the editing machinery introduction module, from the editing machinery introduction module to the editing module, and from the editing module to the enrichment module; and to move nucleic acids and/or proteins to the editing machinery introduction module, all without user intervention.

18. The automated multi-module cell editing instrument of claim 17, further comprising at least one reagent cartridge containing reagents to perform cell editing in the automated multi-module cell editing instrument.

19. The automated multi-module cell editing instrument of claim 18, wherein the receptacles for the cells and nucleic acids are disposed within the reagent cartridge.

20. An automated multi-module cell editing instrument comprising:
   a housing configured to house some or all of the modules;
   a receptacle configured to receive cells;
   at least one receptacle configured to receive nucleic acids, wherein the nucleic acids comprise editing machinery;
   a growth module configured to grow the cells;
   a filtration module configured to concentrate the cells and render the cells electrocompetent;
   a transformation module comprising a flow-through electroporator to introduce the nucleic acids into the cells;
   a combination recovery and editing module configured to allow the cells to recover after electroporation in the transformation module and to allow the nucleic acids to edit the cells;

an enrichment module to enrich for cells receiving the editing machinery;

a processor configured to operate the automated multi-module cell editing instrument based on user input and/or selection of a pre-programmed script; and an automated liquid handling system to move cells from the receptacle configured to receive cells to the growth module; from the growth module to the filtration module, from the filtration module to the transformation module, from the transformation module to the combination recovery and editing module, and from the combination recovery and editing module to the enrichment module; and to move nucleic acids from the receptacle configured to receive nucleic acids to the transformation module, all without user intervention.

* * * * *

UNITED STATES PATENT AND TRADEMARK OFFICE
CERTIFICATE OF CORRECTION

PATENT NO. : 10,689,669 B1
APPLICATION NO. : 16/740418
DATED : June 23, 2020
INVENTOR(S) : Emily Feldman et al.

It is certified that error appears in the above-identified patent and that said Letters Patent is hereby corrected as shown below:

In the Claims

Column 63 Line 11, Claim 1 should read:
An automated multi-module cell editing instrument comprising:
    a housing configured to house all or some of the modules;
    a receptacle configured to receive cells;
one or more receptacles configured to receive nucleic acids and/or proteins, wherein the nucleic acids and/or proteins comprise editing machinery;
an editing machinery introduction module configured to introduce the nucleic acids and/or proteins into the cells;
an editing module configured to allow the introduced nucleic acids to edit nucleic acids in the cells;
an enrichment module to enrich for cells receiving the editing machinery;
    a processor configured to operate the automated multi-module cell editing instrument based on user input and/or selection of a pre-programmed script; and
an automated liquid handling system to move cells from the receptacle configured to receive cells to the editing machinery introduction module, from the editing machinery introduction module to the editing module, and from the editing module to the enrichment module; and to move nucleic acids and/or proteins to the editing machinery introduction module, all without user intervention.

Column 64 Line 21, Claim 17 should read:
An automated multi-module cell editing instrument comprising:
    a housing configured to house all or some of the modules;
    a receptacle configured to receive cells, nucleic acids and/or proteins, wherein the nucleic acids and/or proteins comprise editing machinery;
an editing machinery introduction module configured to introduce the nucleic acids and/or proteins into the cells;
an editing module configured to allow the introduced nucleic acids and/or proteins to edit nucleic acids in the cells;
an enrichment module to enrich for cells receiving the editing machinery;

Signed and Sealed this
Twelfth Day of April, 2022

Drew Hirshfeld
*Performing the Functions and Duties of the
Under Secretary of Commerce for Intellectual Property and
Director of the United States Patent and Trademark Office* a processor configured to operate the automated multi-module cell editing instrument based on user input and/or selection of a pre-programmed script; and an automated liquid handling system to move cells from the receptacle configured to receive cells to the editing machinery introduction module, from the editing machinery introduction module to the editing module, and from the editing module to the enrichment module; and to move nucleic acids and/or proteins to the editing machinery introduction module, all without user intervention.